(12) United States Patent
Longley et al.

(10) Patent No.: US 7,846,909 B2
(45) Date of Patent: Dec. 7, 2010

(54) METHOD AND COMPOSITIONS FOR INHIBITING MAGE PROTEIN INTERACTION WITH KAP-1

(75) Inventors: B. Jack Longley, Madison, WI (US);
Bing Yang, Madison, WI (US);
Jianqiang Wu, Madison, WI (US);
Yongsheng Ma, Hamden, CT (US)

(73) Assignee: Wisconsin Alumni Research Foundation, Madison, WI (US)

( * ) Notice: Subject to any disclaimer, the term of this patent is extended or adjusted under 35 U.S.C. 154(b) by 49 days.

(21) Appl. No.: 11/956,177

(22) Filed: Dec. 13, 2007

(65) Prior Publication Data

US 2009/0062226 A1 Mar. 5, 2009

Related U.S. Application Data

(60) Provisional application No. 60/870,043, filed on Dec. 14, 2006.

(51) Int. Cl.
*A61K 48/00* (2006.01)
*C07H 21/02* (2006.01)
*C07H 21/04* (2006.01)

(52) U.S. Cl. .......... 514/44; 536/23.1; 536/24.5
(58) Field of Classification Search .............. None
See application file for complete search history.

(56) References Cited

PUBLICATIONS

Monte et al., MAGE-A tumor antigens target p53 transactivation function through histone deacetylase recruitment and confer resistance to chemotherapeutic agents, Jul. 2006, PNAS, vol. 103, No. 30, pp. 11160-11165.*

* cited by examiner

*Primary Examiner*—Amy Bowman
(74) *Attorney, Agent, or Firm*—Kening Li; Pinsent Masons LLP

(57) ABSTRACT

Method for inhibiting tumor cell formation or tumor cell growth, and method for inducing apoptosis in sperms, the method comprising administering to a patient in need thereof an antagonist that inhibits the binding of MAGE protein to KAP-1, thereby inhibiting MAGE gene function. Also disclosed are pharmaceutical compositions comprising the same, and method for screening a substance that inhibits MAGE protein binding to KAP-1.

10 Claims, 31 Drawing Sheets

FIGURE 8  1 OF 7
A. Hs-294T cells
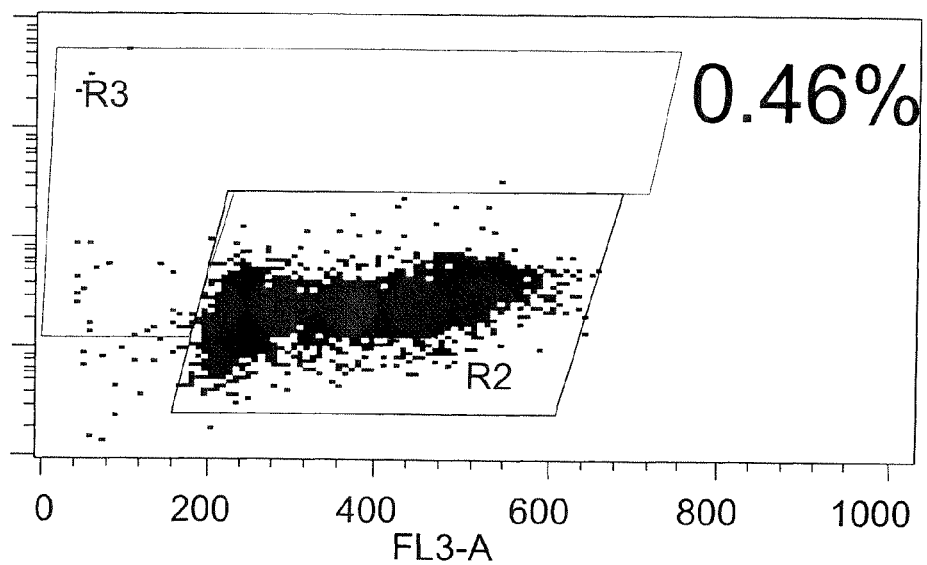
Mock-transfection
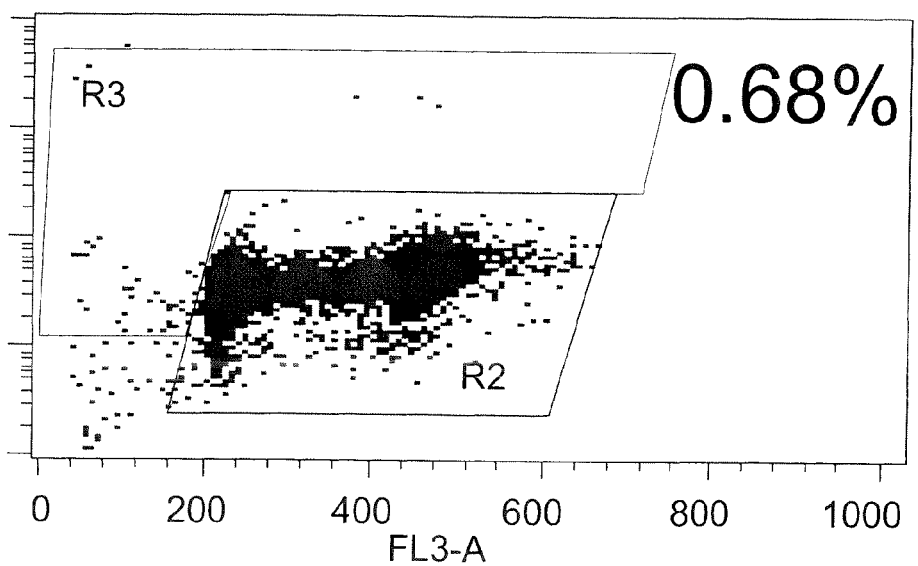
FMK Non-specific siRNA FMK+Nonpan MAGE-A siRNA FMK+ pan MAGE-A siRNA FIGURE 8       4 OF 7
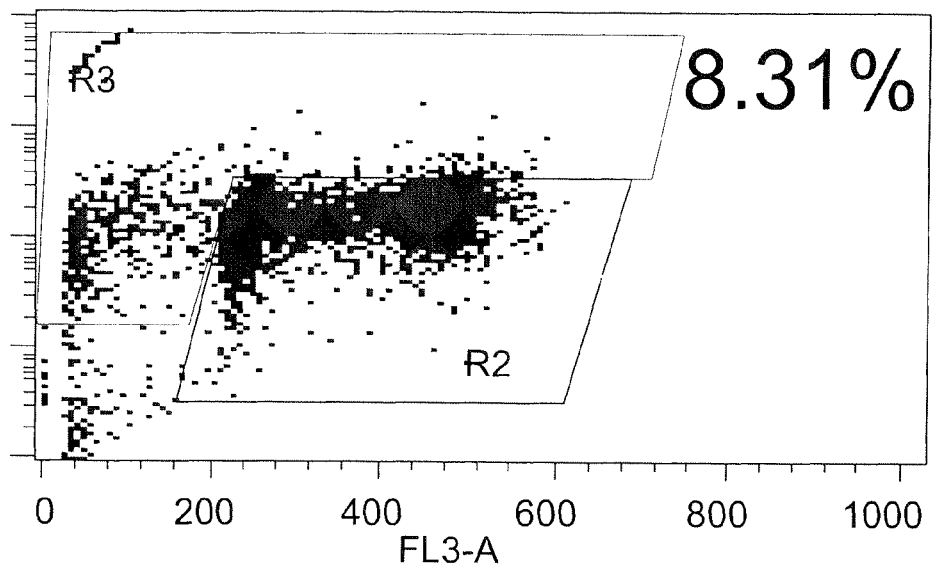
C2 siRNA
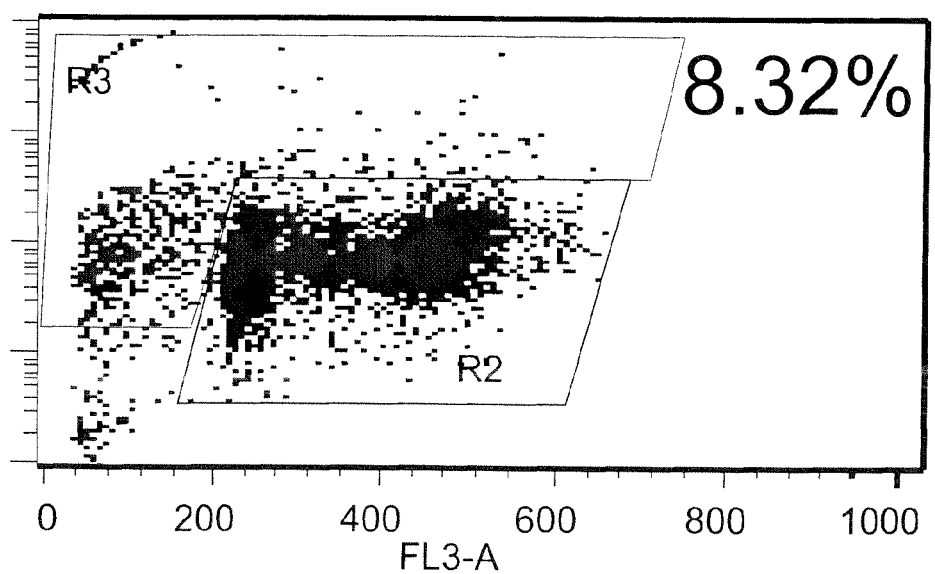
FMK+C2 siRNA

B. S91 cells

Mock-transfection

FMK

FIGURE 8     6 OF 7
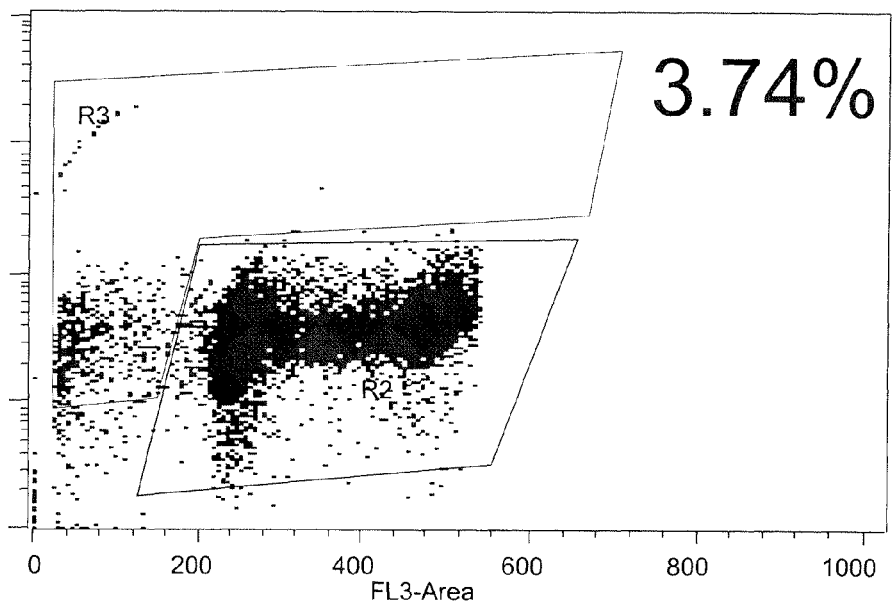
Non-specific siRNA
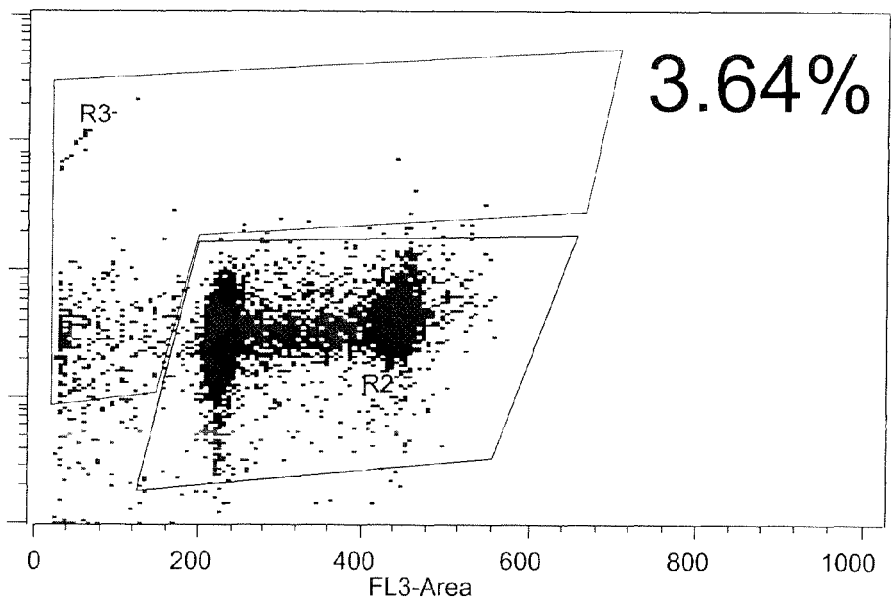
FMK+Non-specific siRNA Blot: pan MAGE-A MAGE-A protein expressed in all three HCT 116 cell variants.

1 OF 3

2 OF 3

3 OF 3

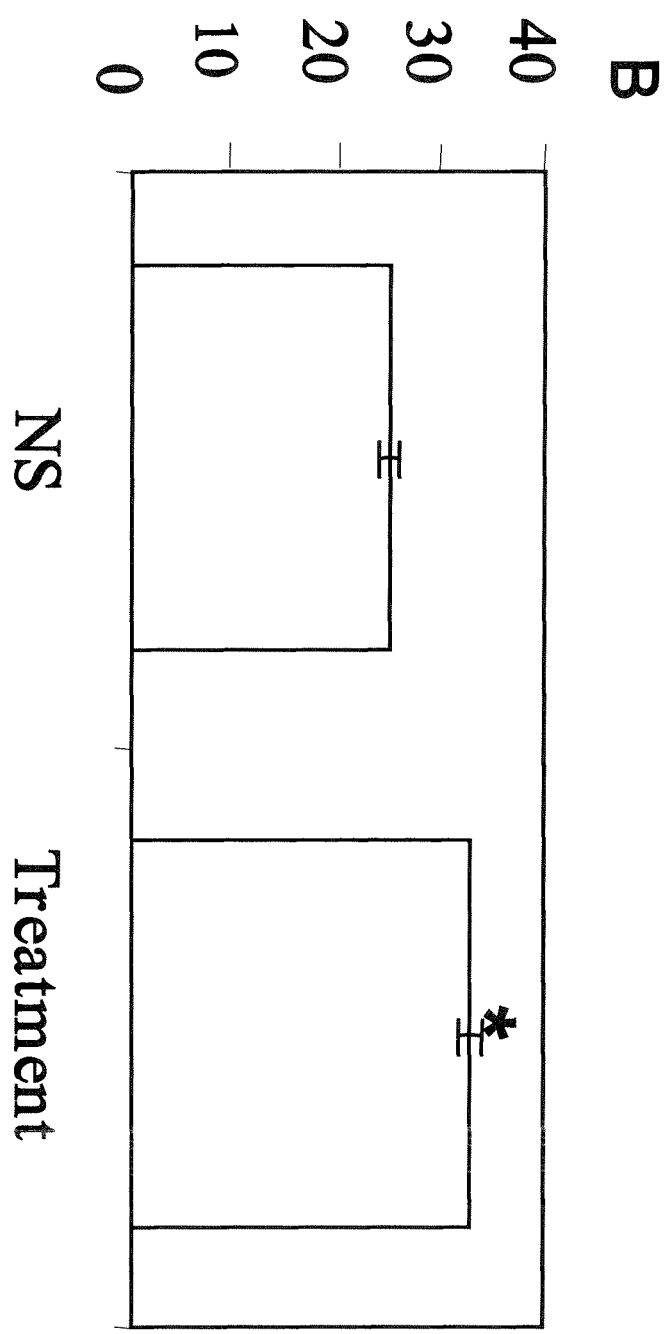
FIGURE 13   2 OF 3

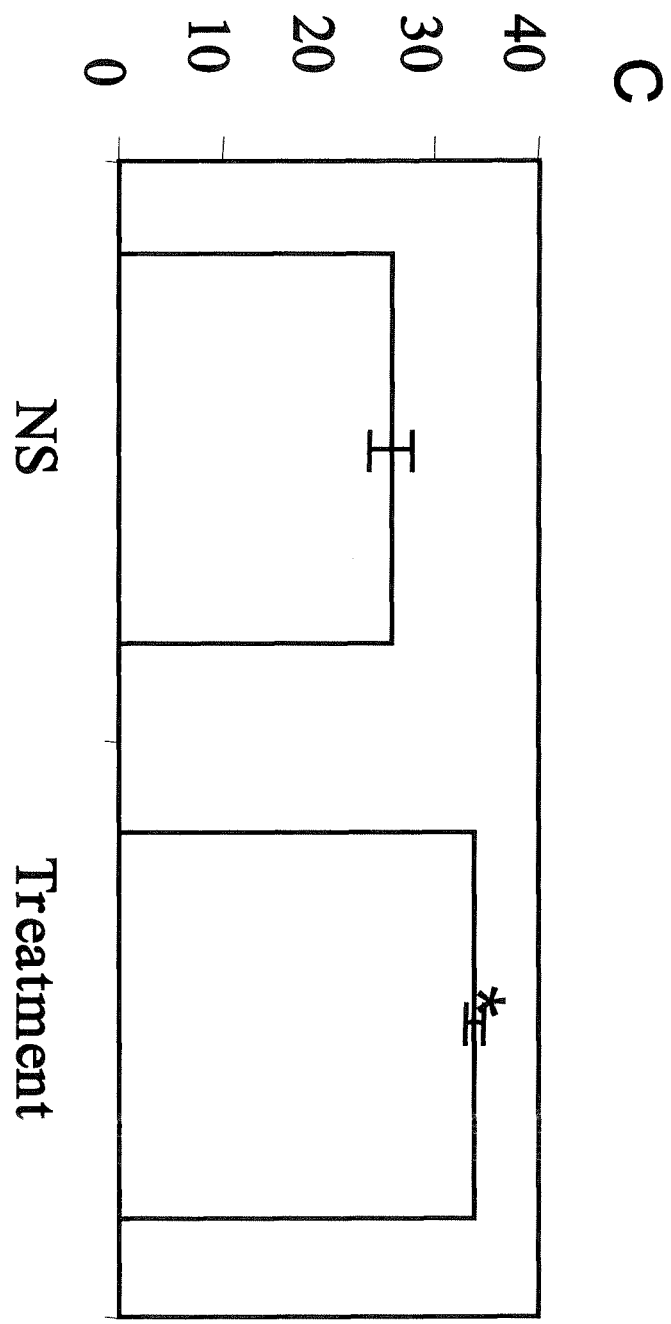
FIGURE 13  3 OF 3
Days to Reach 13mm Mean Tumor Dimension

Figure 15 siRNA Sequences

| Human Pan MAGE-A siRNA SmartPool Duplex 1 | sense 5'-GAAACCAGCUAUGUGAAAG-3' (SEQ ID NO: 1)<br>antisense 5'-CUUUCACAUAGCUGGUUUC-3' (SEQ ID NO: 2) |
|---|---|
| Duplex 2 | sense 5'-UGAAACCAGCUAUGUGAAA-3' (SEQ ID NO: 3)<br>antisense 5'-UUUCACAUAGCUGGUUUCA-3' (SEQ ID NO: 4) |
| Duplex 3 | sense 5'-UGAAACCAGCUAUGUGAAA-3' (SEQ ID NO: 5)<br>antisense 5'-UUUCACAUAGCUGGUUUCA-3' (SEQ ID NO: 6) |
| Duplex 4 | sense 5'-GGUCACAAAGGCAGAAAUG-3' (SEQ ID NO: 7)<br>antisense 5'-CAUUUCUGCCUUUGUGACC-3' (SEQ ID NO: 8) |
| Human MAGE-A1 siRNA SmartPool Duplex 1 | sense 5'-CUAAGAAGGUGGCUGAUUU-3' (SEQ ID NO: 9)<br>antisense 5'-AAAUCAGCCACCUUCUUAG-3' (SEQ ID NO: 10) |
| Duplex 2 | sense 5'-UGAAAGUCCUUGAGUAUGU-3' (SEQ ID NO: 11)<br>antisense 5'-ACAUACUCAAGGACUUUCA-3' (SEQ ID NO: 12) |
| Duplex 3 | sense 5'-UGGCUGAUUUGGUUGGUUU-3' (SEQ ID NO: 13)<br>antisense 5'-AAACCAACCAAAUCAGCCA-3' (SEQ ID NO: 14) |
| Duplex 4 | sense 5'-CAAGGUCAGUGCAAGAGUU-3' (SEQ ID NO: 15)<br>antisense 5'-AACUCUUGCACUGACCUUG- 3' (SEQ ID NO: 16) |
| Human MAGE-A2 siRNA SmartPool Duplex 1 | sense 5'- GAGAGUGUCCUCAGAAAUU-3' (SEQ ID NO: 17)<br>antisense 5'-AAUUUCUGAGGACACUCUC-3' (SEQ ID NO: 18) |
| Duplex 2 | sense 5'- GAGAACCUCACAUUCCUA-3' (SEQ ID NO: 19)<br>antisense 5'-UAGGAAAUGUGAGGUUCUC-3' (SEQ ID NO: 20) |
| Duplex 3 | sense 5'- GCACUGCAAGCCUGAAGAA-3' (SEQ ID NO: 21)<br>antisense 5'-UUCUUCAGGCUUGCAGUGC-3' (SEQ ID NO: 22) |
| Duplex 4 | sense 5'- UGAAACCAGCUAUGUGAAA-3' (SEQ ID NO: 23)<br>antisense 5'-UUUCACAUAGCUGGUUUCA-3' (SEQ ID NO: 24) |
| Human MAGE-A3 siRNA SmartPool Duplex1 | sense 5'-GAAACCAGCUAUGUGAAAG-3' (SEQ ID NO: 25)<br>antisense 5'-CUUUCACAUAGCUGGUUUC-3' (SEQ ID NO: 26) |
| Duplex 2 | sense 5'- UGAAACCAGCUAUGUGAAA-3' (SEQ ID NO: 27)<br>antisense 5'-UUUCACAUAGCUGGUUUCA-3' (SEQ ID NO: 28) |
| Duplex 3 | sense 5'- UGAAACCAGCUAUGUGAAA-3' (SEQ ID NO: 29)<br>antisense 5'-UUUCACAUAGCUGGUUUCA-3' (SEQ ID NO: 30) |
| Duplex 4 | sense 5'-GGUCACAAAGGCAGAAAUG-3' (SEQ ID NO: 31)<br>antisense 5'-CAUUUCUGCCUUUGUGACC-3' (SEQ ID NO: 32) |
| Human MAGE-A5 siRNA SmartPool Duplex 1 | sense 5'- CCAUUAAGGGCUCCAGCAA-3' (SEQ ID NO: 33)<br>antisense 5'-UUGCUGGAGCCCUUAAUGG-3' (SEQ ID NO: 34) |
| Duplex 2 | sense 5'-CGAGCAGCACUCAGUAAGA-3' (SEQ ID NO: 35)<br>antisense 5'-UCUUACUGAGUGCUGCUCG-3' (SEQ ID NO: 36) |
| Duplex 3 | sense 5'- GAGCAGCACUCAGUAAGAA-3' (SEQ ID NO: 37)<br>antisense 5'-UUCUUACUGAGUGCUGCUC-3' (SEQ ID NO: 38) |
| Duplex 4 | sense 5'-GAAGGUGGCUGACUUGAUU-3' (SEQ ID NO: 39)<br>antisense 5'-AAUCAAGUCAGCCACCUUC-3' (SEQ ID NO: 40) |
| Human MAGE-A6 siRNA SmartPool Duplex 1 | sense 5'-GAGAAGAUCUGUAAGUAAG-3'(SEQ ID NO: 41)<br>antisense 5'-CUUACUUACAGAUCUUCUC-3' (SEQ ID NO: 42) |
| Duplex 2 | sense 5'-GCACGUGAGUCCUGAGGUU-3' (SEQ ID NO: 43)<br>antisense 5'-AACCUCAGGACUCACGUGC-3' (SEQ ID NO: 44) |
| Duplex 3 | sense 5'-GGACUUCAAUAAAUUUGGA-3' (SEQ ID NO: 45)<br>antisense 5'-UCCAAAUUUAUUGAAGUCC-3' (SEQ ID NO: 46) |
| Duplex 4 | sense 5'-GGGCAGGGCUGGUUAGAAG-3' (SEQ ID NO: 47)<br>antisense 5'-CUUCUAACCAGCCCUGCCC-3' (SEQ ID NO: 48) |
| Human MAGE-A12 siRNA SmartPool Duplex 1 | sense 5'-GGACAGUGUCUUUGCGCAU-3' (SEQ ID NO: 49)<br>antisense 5'-AUGCGCAAAGACACUGUCC-3' (SEQ ID NO: 50) |
| Duplex 2 | sense 5'-CAACUAUACUCUCUGGAGU-3' (SEQ ID NO: 51)<br>antisense 5'-ACUCCAGAGAGUAUAGUUG-3' (SEQ ID NO: 52) |

Figure 15 (continued) siRNA Sequences

| | |
|---|---|
| Duplex 3 | sense 5'- GAGACGAGCUUCCAAGUAG-3' (SEQ ID NO: 53)<br>antisense 5'-CUACUUGGAAGCUCGUCUC-3' (SEQ ID NO: 54) |
| Duplex 4 | sense 5'- CCACUACCAUCAACUAUAC-3' (SEQ ID NO: 55)<br>antisense 5'-GUAUAGUUGAUGGUAGUGG-3' (SEQ ID NO: 56) |
| Human MAGE-B2 siRNA SmartPool Duplex 1 | sense 5'- AGAGAAAGCCGGAGUCUGA-3' (SEQ ID NO: 57)<br>antisense 5'-UCAGACUCCGGCUUUCUCU-3' (SEQ ID NO: 58) |
| Duplex 2 | sense 5'- GAGGAGCACUCAGUCUUUG-3' (SEQ ID NO: 59)<br>antisense 5'-CAAAGACUGAGUGCUCCUC-3' (SEQ ID NO: 60) |
| Duplex 3 | sense 5'-GCCUUGAGCUGAAUAAAGU-3' (SEQ ID NO: 61)<br>antisense 5'-ACUUUAUUCAGCUCAAGGC-3' (SEQ ID NO: 62) |
| Duplex 4 | sense 5'-AGGAAUCCCUGCUCAGUUC-3' (SEQ ID NO: 63)<br>antisense 5'-GAACUGAGCAGGGAUUCCU-3' (SEQ ID NO: 64) |
| Human MAGE-C2 siRNA SmartPool Duplex 1 | sense 5'-GAGAACAGCCUCCUGAUUA-3' (SEQ ID NO: 65)<br>antisense 5'-UAAUCAGGAGGCUGUUCUC-3' (SEQ ID NO: 66) |
| Duplex 2 | sense 5'-CAAGAGAGCCCGUGAGUUC-3' (SEQ ID NO: 67)<br>antisense 5'-GAACUCACGGGCUCUCUUG-3'(SEQ ID NO: 68) |
| Duplex 3 | sense 5'-GGUGUGAUACCAAAUCUUA-3' (SEQ ID NO: 69)<br>antisense 5'-UAAGAUUUGGUAUCACACC-3' (SEQ ID NO: 70) |
| Duplex 4 | sense 5'- ACAGUUCUCCUCCAUAUUA-3' (SEQ ID NO: 71)<br>antisense 5'-UAAUAUGGAGGAGAACUGU (SEQ ID NO: 72) |
| Mouse MAGE-A Complex siRNA SmartPool Duplex 1 | sense 5'- CCAGGAAGCUCAUCUCUGA-3' (SEQ ID NO: 73)<br>antisense 5'-UCAGAGAUGAGCUUCCUGG-3' (SEQ ID NO: 74) |
| Duplex 2 | sense 5'- GAAGGGAAACUAUGUCAGU-3' (SEQ ID NO: 75)<br>antisense 5'-ACUGACAUAGUUUCCCUUC-3' (SEQ ID NO: 76) |
| Duplex 3 | sense 5'- UACCAAAGCAGAAAUGUUG-3' (SEQ ID NO: 77)<br>antisense 5'-CAACAUUUCUGCUUUGGUA-3'(SEQ ID NO: 78) |
| Duplex 4 | sense 5'- GUAGAGAGUAUGAGGAGUA-3' (SEQ ID NO: 79)<br>antisense 5'-UACUCCUCAUACUCUCUAC-3' (SEQ ID NO: 80) |
| Mouse MAGE-B complex siRNA SmartPool Duplex 1 | sense 5'-UGGCAGUAGUUAACAAGAA-3' (SEQ ID NO: 81)<br>antisense 5'-UUCUUGUUAACUACUGCCA-3' (SEQ ID NO: 82) |
| Duplex 2 | sense 5'-CAGCACUCAUUCCUAUUUG-3' (SEQ ID NO: 83)<br>antisense 5'-CAAAUAGGAAUGAGUGCUG-3' (SEQ ID NO: 84) |
| Duplex 3 | sense 5'-CAAGAGGUCUGGCAAUUUC-3' (SEQ ID NO: 85)<br>antisense 5'-GAAAUUGCCAGACCUCUUG-3' (SEQ ID NO: 86) |
| Duplex 4 | sense 5'- GCAAGGGUGUUCAUUCCAA-3' (SEQ ID NO: 87)<br>antisense 5'-UUGGAAUGAACACCCUUGC (SEQ ID NO: 88) |
| MAGE-B siSTABLE Plus siRNA Sequence | sense 5'-GCAAGGGUGUUCAUUCCAAUU-3' (SEQ ID NO: 89)<br>antisense 5'-PUUGGAAUGAACACCCUUGCUU-3' (SEQ ID NO: 90) |

Figure 15A siRNA Sequences

| Human Pan MAGE-A siRNA SmartPool Duplex 1 | sense 5'-GAAACCAGCUAUGUGAAAG-3' (SEQ ID NO: 1)<br>antisense 5'-CUUUCACAUAGCUGGUUUC-3' (SEQ ID NO: 2) |
|---|---|
| Duplex 2 | sense 5'-UGAAACCAGCUAUGUGAAA-3' (SEQ ID NO: 3)<br>antisense 5'-UUUCACAUAGCUGGUUUCA-3' (SEQ ID NO: 4) |
| Duplex 3 | sense 5'-UGAAACCAGCUAUGUGAAA-3' (SEQ ID NO: 5)<br>antisense 5'-UUUCACAUAGCUGGUUUCA-3' (SEQ ID NO: 6) |
| Duplex 4 | sense 5'-GGUCACAAAGGCAGAAAUG-3' (SEQ ID NO: 7)<br>antisense 5'-CAUUUCUGCCUUUGUGACC-3' (SEQ ID NO: 8) |
| Human MAGE-A1 siRNA SmartPool Duplex 1 | sense 5'-CUAAGAAGGUGGCUGAUUU-3' (SEQ ID NO: 9)<br>antisense 5'-AAAUCAGCCACCUUCUUAG-3' (SEQ ID NO: 10) |
| Duplex 2 | sense 5'-UGAAAGUCCUUGAGUAUGU-3' (SEQ ID NO: 11)<br>antisense 5'-ACAUACUCAAGGACUUUCA-3' (SEQ ID NO: 12) |
| Duplex 3 | sense 5'-UGGCUGAUUUGGUUGGUUU-3' (SEQ ID NO: 13)<br>antisense 5'-AAACCAACCAAAUCAGCCA-3' (SEQ ID NO: 14) |
| Duplex 4 | sense 5'-CAAGGUCAGUGCAAGAGUU-3' (SEQ ID NO: 15)<br>antisense 5'-AACUCUUGCACUGACCUUG-3' (SEQ ID NO: 16) |
| Human MAGE-A2 siRNA SmartPool Duplex 1 | sense 5'-GAGAGUGUCCUCAGAAAUU-3' (SEQ ID NO: 17)<br>antisense 5'-AAUUUCUGAGGACACUCUC-3' (SEQ ID NO: 18) |
| Duplex 2 | sense 5'-GAGAACCUCACAUUUCCUA-3' (SEQ ID NO: 19)<br>antisense 5'-UAGGAAAUGUGAGGUUCUC-3' (SEQ ID NO: 20) |
| Duplex 3 | sense 5'-GCACUGCAAGCCUGAAGAA-3' (SEQ ID NO: 21)<br>antisense 5'-UUCUUCAGGCUUGCAGUGC-3' (SEQ ID NO: 22) |
| Duplex 4 | sense 5'-UGAAACCAGCUAUGUGAAA-3' (SEQ ID NO: 23)<br>antisense 5'-UUUCACAUAGCUGGUUUCA-3' (SEQ ID NO: 24) |
| Human MAGE-A3/A6 siRNA SmartPool Duplex 1 | sense 5'-GAACUACCCUCUCUGGAGC-3' (SEQ ID NO: 25)<br>antisense 5'-CUUGAUGGGAGAGACCUCG-3' (SEQ ID NO: 26) |
| Duplex 2 | sense 5'-GGAGUGUCGUCGGAAAUUG-3' (SEQ ID NO: 27)<br>antisense 5'-CCUCACAGCAGCCUUUAAC-3' (SEQ ID NO: 28) |
| Duplex 3 | sense 5'-UCAGCAAAGCUUCCGAUUC-3' (SEQ ID NO: 29)<br>antisense 5'-AGUCGUUUCGAAGGCUAAG-3' (SEQ ID NO: 30) |
| Duplex 4 | sense 5'-GGUAAAGAUCAGUGGAGGA-3' (SEQ ID NO: 31)<br>antisense 5'-CCAUUUCUAGUCACCUCCU-3' (SEQ ID NO: 32) |
| Human MAGE-A5 siRNA SmartPool Duplex 1 | sense 5'-CCAUUAAGGGCUCCAGCAA-3' (SEQ ID NO: 33)<br>antisense 5'-UUGCUGGAGCCCUUAAUGG-3' (SEQ ID NO: 34) |
| Duplex 2 | sense 5'-CGAGCAGCACUCAGUAAGA-3' (SEQ ID NO: 35)<br>antisense 5'-UCUUACUGAGUGCUGCUCG-3' (SEQ ID NO: 36) |
| Duplex 3 | sense 5'-GAGCAGCACUCAGUAAGAA-3' (SEQ ID NO: 37)<br>antisense 5'-UUCUUACUGAGUGCUGCUC-3' (SEQ ID NO: 38) |
| Duplex 4 | sense 5'-GAAGGUGGCUGACUUGAUU-3' (SEQ ID NO: 39)<br>antisense 5'-AAUCAAGUCAGCCACCUUC-3' (SEQ ID NO: 40) |

Figure 15B (continued) siRNA Sequences

| | |
|---|---|
| Human MAGE-A12 siRNA SmartPool Duplex 1 | sense 5'-GGACAGUGUCUUUGCGCAU-3' (SEQ ID NO: 41)<br>antisense 5'-AUGCGCAAAGACACUGUCC-3' (SEQ ID NO: 42) |
| Duplex 2 | sense 5'-CAACUAUACUCUCUGGAGU-3' (SEQ ID NO: 43)<br>antisense 5'-ACUCCAGAGAGUAUAGUUG-3' (SEQ ID NO: 44) |
| Duplex 3 | sense 5'- GAGACGAGCUUCCAAGUAG-3' (SEQ ID NO: 45)<br>antisense 5'-CUACUUGGAAGCUCGUCUC-3' (SEQ ID NO: 46) |
| Duplex 4 | sense 5'- CCACUACCAUCAACUAUAC-3' (SEQ ID NO: 47)<br>antisense 5'-GUAUAGUUGAUGGUAGUGG-3' (SEQ ID NO: 48) |
| Human MAGE-B2 siRNA SmartPool Duplex 1 | sense 5'- AGAGAAAGCCGGAGUCUGA-3' (SEQ ID NO: 49)<br>antisense 5'-UCAGACUCCGGCUUUCUCU-3' (SEQ ID NO: 50) |
| Duplex 2 | sense 5'- GAGGAGCACUCAGUCUUUG-3' (SEQ ID NO: 51)<br>antisense 5'-CAAAGACUGAGUGCUCCUC-3' (SEQ ID NO: 52) |
| Duplex 3 | sense 5'-GCCUUGAGCUGAAUAAAGU-3' (SEQ ID NO: 53)<br>antisense 5'-ACUUUAUUCAGCUCAAGGC-3' (SEQ ID NO: 54) |
| Duplex 4 | sense 5'-AGGAAUCCCUGCUCAGUUC-3' (SEQ ID NO: 55)<br>antisense 5'-GAACUGAGCAGGGAUUCCU-3' (SEQ ID NO: 56) |
| Human MAGE-C2 siRNA SmartPool Duplex 1 | sense 5'-GAGAACAGCCUCCUGAUUA-3' (SEQ ID NO: 57)<br>antisense 5'-UAAUCAGGAGGCUGUUCUC-3' (SEQ ID NO: 58) |
| Duplex 2 | sense 5'-CAAGAGAGCCCGUGAGUUC-3' (SEQ ID NO: 59)<br>antisense 5'-GAACUCACGGGCUCUCUUG-3'(SEQ ID NO: 60) |
| Duplex 3 | sense 5'-GGUGUGAUACCAAAUCUUA-3' (SEQ ID NO: 61)<br>antisense 5'-UAAGAUUUGGUAUCACACC-3' (SEQ ID NO: 62) |
| Duplex 4 | sense 5'- ACAGUUCUCCUCCAUAUUA-3' (SEQ ID NO: 63)<br>antisense 5'-UAAUAUGGAGGAGAACUGU (SEQ ID NO: 64) |
| Mouse mMage-a Complex siRNA SmartPool Duplex 1 | sense 5'- CCAGGAAGCUCAUCUCUGA-3' (SEQ ID NO: 65)<br>antisense 5'-UCAGAGAUGAGCUUCCUGG-3' (SEQ ID NO: 66) |
| Duplex 2 | sense 5'- GAAGGGAAACUAUGUCAGU-3' (SEQ ID NO: 67)<br>antisense 5'-ACUGACAUAGUUUCCCUUC-3' (SEQ ID NO: 68) |
| Duplex 3 | sense 5'- UACCAAAGCAGAAAUGUUG-3' (SEQ ID NO: 69)<br>antisense 5'-CAACAUUUCUGCUUUGGUA-3'(SEQ ID NO: 70) |
| Duplex 4 | sense 5'- GUAGAGAGUAUGAGGAGUA-3' (SEQ ID NO: 71)<br>antisense 5'-UACUCCUCAUACUCUCUAC-3' (SEQ ID NO: 72) |
| Mouse mMage-b complex siRNA SmartPool Duplex 1 | sense 5'-UGGCAGUAGUUAACAAGAA-3' (SEQ ID NO: 73)<br>antisense 5'-UUCUUGUUAACUACUGCCA-3' (SEQ ID NO: 74) |
| Duplex 2 | sense 5'-CAGCACUCAUUCCUAUUUG-3' (SEQ ID NO: 75)<br>antisense 5'-CAAAUAGGAAUGAGUGCUG-3' (SEQ ID NO: 76) |
| Duplex 3 | sense 5'-CAAGAGGUCUGGCAAUUUC-3' (SEQ ID NO: 77)<br>antisense 5'-GAAAUUGCCAGACCUCUUG-3' (SEQ ID NO: 78) |
| Duplex 4 | sense 5'- GCAAGGGUGUUCAUUCCAA-3' (SEQ ID NO: 79)<br>antisense 5'-UUGGAAUGAACACCCUUGC (SEQ ID NO: 80) |
| Mouse mMage-b siSTABLE Plus siRNA | sense 5'-GCAAGGGUGUUCAUUCCAAUU-3' (SEQ ID NO: 81)<br>antisense 5'-PUUGGAAUGAACACCCUUGCUU-3' (SEQ ID NO: 82) |

SEQUENCE LISTING

<160> NUMBER OF SEQ ID NOS: 82

<210> SEQ ID NO 1
<211> LENGTH: 19
<212> TYPE: RNA
<213> ORGANISM: Artificial Sequence
<220> FEATURE:
<223> OTHER INFORMATION: Human Pan MAGE-A siRNA

<400> SEQUENCE: 1
gaaaccagcu augugaaag                                                    19

<210> SEQ ID NO 2
<211> LENGTH: 19
<212> TYPE: RNA
<213> ORGANISM: Artificial Sequence
<220> FEATURE:
<223> OTHER INFORMATION: Human Pan MAGE-A siRNA

<400> SEQUENCE: 2
cuuucacaua gcugguuuc                                                    19

<210> SEQ ID NO 3
<211> LENGTH: 19
<212> TYPE: RNA

-continued

```
<213> ORGANISM: Artificial Sequence
<220> FEATURE:
<223> OTHER INFORMATION: Human Pan MAGE-A siRNA

<400> SEQUENCE: 3
ugaaaccagc uaugugaaa                                               19

<210> SEQ ID NO 4
<211> LENGTH: 19
<212> TYPE: RNA
<213> ORGANISM: Artificial Sequence
<220> FEATURE:
<223> OTHER INFORMATION: Human Pan MAGE-A siRNA

<400> SEQUENCE: 4
uuucacauag cugguuuca                                               19

<210> SEQ ID NO 5
<211> LENGTH: 19
<212> TYPE: RNA
<213> ORGANISM: Artificial Sequence
<220> FEATURE:
<223> OTHER INFORMATION: Human Pan MAGE-A siRNA

<400> SEQUENCE: 5
ugaaaccagc uaugugaaa                                               19

<210> SEQ ID NO 6
<211> LENGTH: 19
<212> TYPE: RNA
<213> ORGANISM: Artificial Sequence
<220> FEATURE:
<223> OTHER INFORMATION: Human Pan MAGE-A siRNA

<400> SEQUENCE: 6
uuucacauag cugguuuca                                               19

<210> SEQ ID NO 7
<211> LENGTH: 19
<212> TYPE: RNA
<213> ORGANISM: Artificial Sequence
<220> FEATURE:
<223> OTHER INFORMATION: Human Pan MAGE-A siRNA

<400> SEQUENCE: 7
ggucacaaag gcagaaaug                                               19

<210> SEQ ID NO 8
<211> LENGTH: 19
<212> TYPE: RNA
<213> ORGANISM: Artificial Sequence
<220> FEATURE:
<223> OTHER INFORMATION: Human Pan MAGE-A siRNA

<400> SEQUENCE: 8
cauuucugcc uuugugacc                                               19

<210> SEQ ID NO 9
<211> LENGTH: 19
<212> TYPE: RNA
<213> ORGANISM: Artificial Sequence
<220> FEATURE:
<223> OTHER INFORMATION: Human Pan MAGE-A1 siRNA

<400> SEQUENCE: 9
cuaagaaggu ggcugauuu                                               19
```

```
<210> SEQ ID NO 10
<211> LENGTH: 19
<212> TYPE: RNA
<213> ORGANISM: Artificial Sequence
<220> FEATURE:
<223> OTHER INFORMATION: Human Pan MAGE-A1 siRNA

<400> SEQUENCE: 10
aaaucagcca ccuucuuag                                                  19

<210> SEQ ID NO 11
<211> LENGTH: 19
<212> TYPE: RNA
<213> ORGANISM: Artificial Sequence
<220> FEATURE:
<223> OTHER INFORMATION: Human Pan MAGE-A1 siRNA

<400> SEQUENCE: 11
ugaaaguccu ugaguaugu                                                  19

<210> SEQ ID NO 12
<211> LENGTH: 19
<212> TYPE: RNA
<213> ORGANISM: Artificial Sequence
<220> FEATURE:
<223> OTHER INFORMATION: Human Pan MAGE-A1 siRNA

<400> SEQUENCE: 12
acauacucaa ggacuuuca                                                  19

<210> SEQ ID NO 13
<211> LENGTH: 19
<212> TYPE: RNA
<213> ORGANISM: Artificial Sequence
<220> FEATURE:
<223> OTHER INFORMATION: Human Pan MAGE-A1 siRNA

<400> SEQUENCE: 13
uggcugauuu gguugguuu                                                  19

<210> SEQ ID NO 14
<211> LENGTH: 19
<212> TYPE: RNA
<213> ORGANISM: Artificial Sequence
<220> FEATURE:
<223> OTHER INFORMATION: Human Pan MAGE-A1 siRNA

<400> SEQUENCE: 14
aaaccaacca aaucagcca                                                  19

<210> SEQ ID NO 15
<211> LENGTH: 19
<212> TYPE: RNA
<213> ORGANISM: Artificial Sequence
<220> FEATURE:
<223> OTHER INFORMATION: Human Pan MAGE-A1 siRNA

<400> SEQUENCE: 15
caaggucagu gcaagaguu                                                  19

<210> SEQ ID NO 16
<211> LENGTH: 19
<212> TYPE: RNA
<213> ORGANISM: Artificial Sequence
<220> FEATURE:
```

```
<223> OTHER INFORMATION: Human Pan MAGE-A1 siRNA

<400> SEQUENCE: 16
aacucuugca cugaccuug                                                19

<210> SEQ ID NO 17
<211> LENGTH: 19
<212> TYPE: RNA
<213> ORGANISM: Artificial Sequence
<220> FEATURE:
<223> OTHER INFORMATION: Human Pan MAGE-A2 siRNA

<400> SEQUENCE: 17
gagagugucc ucagaaauu                                                19

<210> SEQ ID NO 18
<211> LENGTH: 19
<212> TYPE: RNA
<213> ORGANISM: Artificial Sequence
<220> FEATURE:
<223> OTHER INFORMATION: Human Pan MAGE-A2 siRNA

<400> SEQUENCE: 18
aauuucugag gacacucuc                                                19

<210> SEQ ID NO 19
<211> LENGTH: 19
<212> TYPE: RNA
<213> ORGANISM: Artificial Sequence
<220> FEATURE:
<223> OTHER INFORMATION: Human Pan MAGE-A2 siRNA

<400> SEQUENCE: 19
gagaaccuca cauuuccua                                                19

<210> SEQ ID NO 20
<211> LENGTH: 19
<212> TYPE: RNA
<213> ORGANISM: Artificial Sequence
<220> FEATURE:
<223> OTHER INFORMATION: Human Pan MAGE-A2 siRNA

<400> SEQUENCE: 20
uaggaaaugu gagguucuc                                                19

<210> SEQ ID NO 21
<211> LENGTH: 19
<212> TYPE: RNA
<213> ORGANISM: Artificial Sequence
<220> FEATURE:
<223> OTHER INFORMATION: Human Pan MAGE-A2 siRNA

<400> SEQUENCE: 21
gcacugcaag ccugaagaa                                                19

<210> SEQ ID NO 22
<211> LENGTH: 19
<212> TYPE: RNA
<213> ORGANISM: Artificial Sequence
<220> FEATURE:
<223> OTHER INFORMATION: Human Pan MAGE-A2 siRNA

<400> SEQUENCE: 22
uucuucaggc uugcagugc                                                19
```

```
<210> SEQ ID NO 23
<211> LENGTH: 19
<212> TYPE: RNA
<213> ORGANISM: Artificial Sequence
<220> FEATURE:
<223> OTHER INFORMATION: Human Pan MAGE-A2 siRNA

<400> SEQUENCE: 23
ugaaaccagc uaugugaaa                                               19

<210> SEQ ID NO 24
<211> LENGTH: 19
<212> TYPE: RNA
<213> ORGANISM: Artificial Sequence
<220> FEATURE:
<223> OTHER INFORMATION: Human Pan MAGE-A2 siRNA

<400> SEQUENCE: 24
uuucacauag cugguuuca                                               19

<210> SEQ ID NO 25
<211> LENGTH: 19
<212> TYPE: RNA
<213> ORGANISM: Artificial Sequence
<220> FEATURE:
<223> OTHER INFORMATION: Human Pan MAGE-A3/A6 siRNA

<400> SEQUENCE: 25
gaacuacccu cucuggagc                                               19

<210> SEQ ID NO 26
<211> LENGTH: 19
<212> TYPE: RNA
<213> ORGANISM: Artificial Sequence
<220> FEATURE:
<223> OTHER INFORMATION: Human Pan MAGE-A3/A6 siRNA

<400> SEQUENCE: 26
ggagugucgu cggaaauug                                               19

<210> SEQ ID NO 27
<211> LENGTH: 19
<212> TYPE: RNA
<213> ORGANISM: Artificial Sequence
<220> FEATURE:
<223> OTHER INFORMATION: Human Pan MAGE-A3/A6 siRNA

<400> SEQUENCE: 27
ggagugucgu cggaaauug                                               19

<210> SEQ ID NO 28
<211> LENGTH: 19
<212> TYPE: RNA
<213> ORGANISM: Artificial Sequence
<220> FEATURE:
<223> OTHER INFORMATION: Human Pan MAGE-A3/A6 siRNA

<400> SEQUENCE: 28
ccucacagca gccuuuaac                                               19

<210> SEQ ID NO 29
<211> LENGTH: 19
<212> TYPE: RNA
<213> ORGANISM: Artificial Sequence
<220> FEATURE:
<223> OTHER INFORMATION: Human Pan MAGE-A3/A6 siRNA
```

```
<400> SEQUENCE: 29
ucagcaaagc uuccgauuc                                                    19

<210> SEQ ID NO 30
<211> LENGTH: 19
<212> TYPE: RNA
<213> ORGANISM: Artificial Sequence
<220> FEATURE:
<223> OTHER INFORMATION: Human Pan MAGE-A3/A6 siRNA

<400> SEQUENCE: 30
agucguuucg aaggcuaag                                                    19

<210> SEQ ID NO 31
<211> LENGTH: 19
<212> TYPE: RNA
<213> ORGANISM: Artificial Sequence
<220> FEATURE:
<223> OTHER INFORMATION: Human Pan MAGE-A3/A6 siRNA

<400> SEQUENCE: 31
gguaaagauc aguggagga                                                    19

<210> SEQ ID NO 32
<211> LENGTH: 19
<212> TYPE: RNA
<213> ORGANISM: Artificial Sequence
<220> FEATURE:
<223> OTHER INFORMATION: Human Pan MAGE-A3/A6 siRNA

<400> SEQUENCE: 32
ccauuucuag ucaccuccu                                                    19

<210> SEQ ID NO 33
<211> LENGTH: 19
<212> TYPE: RNA
<213> ORGANISM: Artificial Sequence
<220> FEATURE:
<223> OTHER INFORMATION: Human Pan MAGE-A5 siRNA

<400> SEQUENCE: 33
ccauuaaggg cuccagcaa                                                    19

<210> SEQ ID NO 34
<211> LENGTH: 19
<212> TYPE: RNA
<213> ORGANISM: Artificial Sequence
<220> FEATURE:
<223> OTHER INFORMATION: Human Pan MAGE-A3/A6 siRNA

<400> SEQUENCE: 34
uugcuggagc ccuuaaugg                                                    19

<210> SEQ ID NO 35
<211> LENGTH: 19
<212> TYPE: RNA
<213> ORGANISM: Artificial Sequence
<220> FEATURE:
<223> OTHER INFORMATION: Human Pan MAGE-A3/A6 siRNA

<400> SEQUENCE: 35
cgagcagcac ucaguaaga                                                    19

<210> SEQ ID NO 36
<211> LENGTH: 19
```

```
<212> TYPE: RNA
<213> ORGANISM: Artificial Sequence
<220> FEATURE:
<223> OTHER INFORMATION: Human Pan MAGE-A5 siRNA

<400> SEQUENCE: 36
ucuuacugag ugcugcucg                                                    19

<210> SEQ ID NO 37
<211> LENGTH: 19
<212> TYPE: RNA
<213> ORGANISM: Artificial Sequence
<220> FEATURE:
<223> OTHER INFORMATION: Human Pan MAGE-A5 siRNA

<400> SEQUENCE: 37
gagcagcacu caguaagaa                                                    19

<210> SEQ ID NO 38
<211> LENGTH: 19
<212> TYPE: RNA
<213> ORGANISM: Artificial Sequence
<220> FEATURE:
<223> OTHER INFORMATION: Human Pan MAGE-A5 siRNA

<400> SEQUENCE: 38
uucuuacuga gugcugcuc                                                    19

<210> SEQ ID NO 39
<211> LENGTH: 19
<212> TYPE: RNA
<213> ORGANISM: Artificial Sequence
<220> FEATURE:
<223> OTHER INFORMATION: Human Pan MAGE-A5 siRNA

<400> SEQUENCE: 39
gaagguggcu gacuugauu                                                    19

<210> SEQ ID NO 40
<211> LENGTH: 19
<212> TYPE: RNA
<213> ORGANISM: Artificial Sequence
<220> FEATURE:
<223> OTHER INFORMATION: Human Pan MAGE-A5 siRNA

<400> SEQUENCE: 40
aaucaaguca gccaccuuc                                                    19

<210> SEQ ID NO 41
<211> LENGTH: 19
<212> TYPE: RNA
<213> ORGANISM: Artificial Sequence
<220> FEATURE:
<223> OTHER INFORMATION: Human Pan MAGE-A12 siRNA

<400> SEQUENCE: 41
ggacaguguc uuugcgcau                                                    19

<210> SEQ ID NO 42
<211> LENGTH: 19
<212> TYPE: RNA
<213> ORGANISM: Artificial Sequence
<220> FEATURE:
<223> OTHER INFORMATION: Human Pan MAGE-A12 siRNA

<400> SEQUENCE: 42
```
augcgcaaag acacugucc                                                    19

<210> SEQ ID NO 43
<211> LENGTH: 19
<212> TYPE: RNA
<213> ORGANISM: Artificial Sequence
<220> FEATURE:
<223> OTHER INFORMATION: Human Pan MAGE-A12 siRNA

<400> SEQUENCE: 43
acuccagaga guauaguug                                                    19

<210> SEQ ID NO 44
<211> LENGTH: 19
<212> TYPE: RNA
<213> ORGANISM: Artificial Sequence
<220> FEATURE:
<223> OTHER INFORMATION: Human Pan MAGE-A12 siRNA

<400> SEQUENCE: 44
gagacgagcu uccaaguag                                                    19

<210> SEQ ID NO 45
<211> LENGTH: 19
<212> TYPE: RNA
<213> ORGANISM: Artificial Sequence
<220> FEATURE:
<223> OTHER INFORMATION: Human Pan MAGE-A12 siRNA

<400> SEQUENCE: 45
gagacgagcu uccaaguag                                                    19

<210> SEQ ID NO 46
<211> LENGTH: 19
<212> TYPE: RNA
<213> ORGANISM: Artificial Sequence
<220> FEATURE:
<223> OTHER INFORMATION: Human Pan MAGE-A12 siRNA

<400> SEQUENCE: 46
cuacuuggaa gcucgucuc                                                    19

<210> SEQ ID NO 47
<211> LENGTH: 19
<212> TYPE: RNA
<213> ORGANISM: Artificial Sequence
<220> FEATURE:
<223> OTHER INFORMATION: Human Pan MAGE-A12 siRNA

<400> SEQUENCE: 47
ccacuaccau caacuauac                                                    19

<210> SEQ ID NO 48
<211> LENGTH: 19
<212> TYPE: RNA
<213> ORGANISM: Artificial Sequence
<220> FEATURE:
<223> OTHER INFORMATION: Human Pan MAGE-A12 siRNA

<400> SEQUENCE: 48
guauaguuga ugguagugg                                                    19

<210> SEQ ID NO 49
<211> LENGTH: 19
<212> TYPE: RNA
<213> ORGANISM: Artificial Sequence

```
<220> FEATURE:
<223> OTHER INFORMATION: Human Pan MAGE-B2 siRNA

<400> SEQUENCE: 49
agagaaagcc ggagucuga                                              19

<210> SEQ ID NO 50
<211> LENGTH: 19
<212> TYPE: RNA
<213> ORGANISM: Artificial Sequence
<220> FEATURE:
<223> OTHER INFORMATION: Human Pan MAGE-B2 siRNA

<400> SEQUENCE: 50
ucagacuccg gcuucucu                                               19

<210> SEQ ID NO 51
<211> LENGTH: 19
<212> TYPE: RNA
<213> ORGANISM: Artificial Sequence
<220> FEATURE:
<223> OTHER INFORMATION: Human Pan MAGE-B2 siRNA

<400> SEQUENCE: 51
gaggagcacu cagucuuug                                              19

<210> SEQ ID NO 52
<211> LENGTH: 19
<212> TYPE: RNA
<213> ORGANISM: Artificial Sequence
<220> FEATURE:
<223> OTHER INFORMATION: Human Pan MAGE-B2 siRNA

<400> SEQUENCE: 52
caaagacuga gugcuccuc                                              19

<210> SEQ ID NO 53
<211> LENGTH: 19
<212> TYPE: RNA
<213> ORGANISM: Artificial Sequence
<220> FEATURE:
<223> OTHER INFORMATION: Human Pan MAGE-B2 siRNA

<400> SEQUENCE: 53
gccuugagcu gaauaaagu                                              19

<210> SEQ ID NO 54
<211> LENGTH: 19
<212> TYPE: RNA
<213> ORGANISM: Artificial Sequence
<220> FEATURE:
<223> OTHER INFORMATION: Human Pan MAGE-B2 siRNA

<400> SEQUENCE: 54
acuuuauuca gcucaaggc                                              19

<210> SEQ ID NO 55
<211> LENGTH: 19
<212> TYPE: RNA
<213> ORGANISM: Artificial Sequence
<220> FEATURE:
<223> OTHER INFORMATION: Human Pan MAGE-B2 siRNA

<400> SEQUENCE: 55
aggaaucccu gcucaguuc                                              19
```

<210> SEQ ID NO 56
<211> LENGTH: 19
<212> TYPE: RNA
<213> ORGANISM: Artificial Sequence
<220> FEATURE:
<223> OTHER INFORMATION: Human Pan MAGE-B2 siRNA

<400> SEQUENCE: 56
gaacugagca gggauuccu                                              19

<210> SEQ ID NO 57
<211> LENGTH: 19
<212> TYPE: RNA
<213> ORGANISM: Artificial Sequence
<220> FEATURE:
<223> OTHER INFORMATION: Human Pan MAGE-C2 siRNA

<400> SEQUENCE: 57
gagaacagcc uccugauua                                              19

<210> SEQ ID NO 58
<211> LENGTH: 19
<212> TYPE: RNA
<213> ORGANISM: Artificial Sequence
<220> FEATURE:
<223> OTHER INFORMATION: Human Pan MAGE-C2 siRNA

<400> SEQUENCE: 58
uaaucaggag gcuguucuc                                              19

<210> SEQ ID NO 59
<211> LENGTH: 19
<212> TYPE: RNA
<213> ORGANISM: Artificial Sequence
<220> FEATURE:
<223> OTHER INFORMATION: Human Pan MAGE-C2 siRNA

<400> SEQUENCE: 59
caagagagcc cgugaguuc                                              19

<210> SEQ ID NO 60
<211> LENGTH: 19
<212> TYPE: RNA
<213> ORGANISM: Artificial Sequence
<220> FEATURE:
<223> OTHER INFORMATION: Human Pan MAGE-C2 siRNA

<400> SEQUENCE: 60
gaacucacgg gcucucuug                                              19

<210> SEQ ID NO 61
<211> LENGTH: 19
<212> TYPE: RNA
<213> ORGANISM: Artificial Sequence
<220> FEATURE:
<223> OTHER INFORMATION: Human Pan MAGE-C2 siRNA

<400> SEQUENCE: 61
ggugugauac caaaucuua                                              19

<210> SEQ ID NO 62
<211> LENGTH: 19
<212> TYPE: RNA
<213> ORGANISM: Artificial Sequence
<220> FEATURE:
<223> OTHER INFORMATION: Human Pan MAGE-C2 siRNA

```
<400> SEQUENCE: 62
uaagauuugg uaucacacc                                                    19

<210> SEQ ID NO 63
<211> LENGTH: 19
<212> TYPE: RNA
<213> ORGANISM: Artificial Sequence
<220> FEATURE:
<223> OTHER INFORMATION: Human Pan MAGE-C2 siRNA

<400> SEQUENCE: 63
uaauauggag gagaacugu                                                    19

<210> SEQ ID NO 64
<211> LENGTH: 19
<212> TYPE: RNA
<213> ORGANISM: Artificial Sequence
<220> FEATURE:
<223> OTHER INFORMATION: Human Pan MAGE-C2 siRNA

<400> SEQUENCE: 64
uaauauggag gagaacugu                                                    19

<210> SEQ ID NO 65
<211> LENGTH: 19
<212> TYPE: RNA
<213> ORGANISM: Artificial Sequence
<220> FEATURE:
<223> OTHER INFORMATION: Mouse mMage-a Complex siRNA

<400> SEQUENCE: 65
ccaggaagcu caucucuga                                                    19

<210> SEQ ID NO 66
<211> LENGTH: 19
<212> TYPE: RNA
<213> ORGANISM: Artificial Sequence
<220> FEATURE:
<223> OTHER INFORMATION: Mouse mMage-a Complex siRNA

<400> SEQUENCE: 66
ucagagauga gcuuccugg                                                    19

<210> SEQ ID NO 67
<211> LENGTH: 19
<212> TYPE: RNA
<213> ORGANISM: Artificial Sequence
<220> FEATURE:
<223> OTHER INFORMATION: Mouse mMage-a Complex siRNA

<400> SEQUENCE: 67
gaagggaaac uaugucagu                                                    19

<210> SEQ ID NO 68
<211> LENGTH: 18
<212> TYPE: RNA
<213> ORGANISM: Artificial Sequence
<220> FEATURE:
<223> OTHER INFORMATION: siRNA

<400> SEQUENCE: 68
acugacauag uuucccuu                                                     18

<210> SEQ ID NO 69
```

```
<211> LENGTH: 19
<212> TYPE: RNA
<213> ORGANISM: Artificial Sequence
<220> FEATURE:
<223> OTHER INFORMATION: Mouse mMage-a Complex siRNA

<400> SEQUENCE: 69
uaccaaagca gaaauguug                                                      19

<210> SEQ ID NO 70
<211> LENGTH: 19
<212> TYPE: RNA
<213> ORGANISM: Artificial Sequence
<220> FEATURE:
<223> OTHER INFORMATION: Mouse mMage-a Complex siRNA

<400> SEQUENCE: 70
caacauuucu gcuuggua                                                       19

<210> SEQ ID NO 71
<211> LENGTH: 19
<212> TYPE: RNA
<213> ORGANISM: Artificial Sequence
<220> FEATURE:
<223> OTHER INFORMATION: Mouse mMage-a Complex siRNA

<400> SEQUENCE: 71
guagagagua ugaggagua                                                      19

<210> SEQ ID NO 72
<211> LENGTH: 19
<212> TYPE: RNA
<213> ORGANISM: Artificial Sequence
<220> FEATURE:
<223> OTHER INFORMATION: siRNA

<400> SEQUENCE: 72
uacuccucau acucucuac                                                      19

<210> SEQ ID NO 73
<211> LENGTH: 19
<212> TYPE: RNA
<213> ORGANISM: Artificial Sequence
<220> FEATURE:
<223> OTHER INFORMATION: Mouse mMage-b Complex siRNA

<400> SEQUENCE: 73
uggcaguagu uaacaagaa                                                      19

<210> SEQ ID NO 74
<211> LENGTH: 19
<212> TYPE: RNA
<213> ORGANISM: Artificial Sequence
<220> FEATURE:
<223> OTHER INFORMATION: Mouse mMage-b Complex siRNA

<400> SEQUENCE: 74
uucuuguuaa cuacugcca                                                      19

<210> SEQ ID NO 75
<211> LENGTH: 19
<212> TYPE: RNA
<213> ORGANISM: Artificial Sequence
<220> FEATURE:
<223> OTHER INFORMATION: Mouse mMage-b Complex siRNA

<400> SEQUENCE: 75
```
cagcacucau uccuauuug                    19

<210> SEQ ID NO 76
<211> LENGTH: 19
<212> TYPE: RNA
<213> ORGANISM: Artificial Sequence
<220> FEATURE:
<223> OTHER INFORMATION: Mouse mMage-b Complex siRNA

<400> SEQUENCE: 76
caaauaggaa ugagugcug                    19

<210> SEQ ID NO 77
<211> LENGTH: 19
<212> TYPE: RNA
<213> ORGANISM: Artificial Sequence
<220> FEATURE:
<223> OTHER INFORMATION: Mouse mMage-b Complex siRNA

<400> SEQUENCE: 77
caagaggucu ggcaauuuc                    19

<210> SEQ ID NO 78
<211> LENGTH: 19
<212> TYPE: RNA
<213> ORGANISM: Artificial Sequence
<220> FEATURE:
<223> OTHER INFORMATION: Mouse mMage-b Complex siRNA

<400> SEQUENCE: 78
gaaauugcca gaccucuug                    19

<210> SEQ ID NO 79
<211> LENGTH: 19
<212> TYPE: RNA
<213> ORGANISM: Artificial Sequence
<220> FEATURE:
<223> OTHER INFORMATION: Mouse mMage-b Complex siRNA

<400> SEQUENCE: 79
gcaagggugu ucauuccaa                    19

<210> SEQ ID NO 80
<211> LENGTH: 19
<212> TYPE: RNA
<213> ORGANISM: Artificial Sequence
<220> FEATURE:
<223> OTHER INFORMATION: Mouse mMage-b Complex siRNA

<400> SEQUENCE: 80
uuggaaugaa cacccuugc                    19

<210> SEQ ID NO 81
<211> LENGTH: 21
<212> TYPE: RNA
<213> ORGANISM: Artificial Sequence
<220> FEATURE:
<223> OTHER INFORMATION: siRNA

<400> SEQUENCE: 81
gcaagggugu ucauuccaau u                 21

```
<210> SEQ ID NO 82
<211> LENGTH: 20
<212> TYPE: RNA
<213> ORGANISM: Artificial Sequence
<220> FEATURE:
<223> OTHER INFORMATION: siRNA

<400> SEQUENCE: 82
uuggaaugaa cacccuugcu                                              20
```

METHOD AND COMPOSITIONS FOR INHIBITING MAGE PROTEIN INTERACTION WITH KAP-1

CROSS REFERENCE TO A RELATED APPLICATION

This application claims priority to U.S. Provisional Application No. 60/870,043 filed Dec. 14, 2006, the content of which is incorporated herein by reference in its entirety.

FEDERAL GOVERNMENT INTEREST

This invention was made with United States government support under a grant from the National Institutes of Health (NIH), Grant Number NIH AR043356. The United States has certain rights to this invention.

BACKGROUND OF THE INVENTION

The cancer testes (CT) antigens are a group of proteins originally defined by their normal expression in testes and their aberrant expression in melanomas and other cancers. The first CT antigens discovered were members of the MAGE family of proteins, including the MAGE-A, -B, and -C sub-families which are encoded on the X-chromosome and which are now called Class I MAGE antigens (1, 2). Because many Class I MAGE genes are highly homologous and are co-regulated in gametogenesis and in tumors, it has been suggested that many MAGE proteins have similar or complimentary functions (3). Due to these factors and the difficulty in obtaining antibodies that differentiate between nearly identical sub-family members, most studies of MAGE gene expression rely on the use of antibodies recognizing common determinants or on the detection of mRNA, usually by reverse transcription followed by the polymerase chain reaction (RT-PCR) (3, 4). MAGE gene expression can be caused by promoter region demethylation and is widespread in malignancies, being found in 50% or more of melanomas, synovial sarcomas, and primary carcinomas of the lung, head and neck, urinary bladder, and ovaries, as in well as lesser percentages of primary breast carcinomas and myelomas (5-8).

The functions of most Class I MAGE molecules have not been determined, and it is not known whether their expression in tumors is a functionally irrelevant by-product of cellular transformation or could actually contribute to the development of malignancies (2).

KAP1, also known as TRIM28, Tif1β, or Krip1, is an ~106 kD protein with a RING-B-box coiled-coil (RBCC) domain near its amino terminal end (9-11). Complete loss of KAP1 function in the homozygous KAP1 knockout mouse is lethal in utero in the presence of functional p53, and KAP1 is increasingly being recognized as a central molecule in gene regulation (12). Binding to the RBCC motif of KAP1 is required for function of all KRAB domain containing zinc finger transcription factors (13, 14). KAP1 appears to function as a molecular scaffold that coordinates at least four activities necessary for gene specific silencing including: 1. targeting of specific promoters through the KRAB protein zinc finger motifs; 2. promotion of histone deacetylation via the NuRD/histone deacetylase complex; 3. histone 3-K9 methylation via SETDB1; and 4. recruitment of HP1 protein (14).

Of particular interest in tumor biology is the fact that KAP1 acts as a co-repressor of p53 by binding to MDM2, RING domain ubiquitin E3 ligase and a major repressor of the p53 tumor suppressor protein, thereby suppressing p53 expression, p53 acetylation and p53 function (15). Kap1 acts as a p53 co-repressor with MDM2 by several mechanisms including 1) increasing binding of MDM2 to p53; 2) contributing to MDM2 inactivation of p53 transcription functions; 3) increasing MDM2 inhibition of p53 acetylation) and 4) promoting MDM2 mediated ubiquitination and degradation of P53 (15).

The present inventors recently reported that multiple MAGE proteins promote the viability of malignant mast cell lines, mostly by suppressing apoptosis, and other workers have shown that one MAGE molecule, MAGE-A2, binds to p53 (16, 17). U.S. Pat. Publication No. 2005/0265997 discloses a surprising discovery that inhibiting MAGE gene expression or function will inhibit tumor cell formation or tumor cell growth. In addition, sperm cell apoptosis is also induced by inhibition of MAGE gene expression or function. Preferable MAGE antagonists disclosed therein include an anti-MAGE antibody, an antisense molecule, an siRNA molecule, a molecule for forming a triplex nucleic acid molecule with a MAGE encoding polynucleotide, or a small molecule inhibitor of MAGE function.

However, there remains a need for methods and compositions that inhibit the function of MAGE proteins by targeting specific downstream effectors on which MAGE proteins act.

SUMMARY OF THE INVENTION

It has now been discovered that MAGE protein, especially Class I MAGE protein, expression suppresses apoptosis by suppressing p53 and actively contributes to the development of malignancies and promoting tumor survival, and inhibition of MAGE expression or function represents a novel and specific treatment for melanoma and diverse malignancies.

While not willing to be bound by any theory, it is believed that MAGE proteins act as co-repressors of p53 by binding to KAP1 and enhancing its suppression of p53, and or the DNA damage response. MAGE proteins may contribute to the development of malignancies by providing a survival advantage and interfering with MAGE expression or function may prove to be a novel avenue for therapeutic intervention in a wide variety of other malignancies.

As discussed above, the MAGE-A, B, and C protein families comprise the Class-I MAGE/Cancer Testes Antigens, a group of highly homologous proteins whose expression is suppressed in all normal tissues except developing germ cells. Aberrant expression of Class I MAGE proteins occurs in melanomas and many other malignancies, and MAGE proteins have long been recognized as tumor specific targets, but their functions have largely been unknown. It has been surprisingly discovered that suppression of Class I MAGE proteins induces apoptosis in the HS-294T, A375, and S91 MAGE positive melanoma cell lines and that members of all three families of MAGE Class I proteins form complexes with KAP1, a scaffolding protein that is known as a co-repressor of p53 expression and function, and that is known to be central to the DNA damage response. In addition to inducing apoptosis, MAGE suppression decreases KAP1 complexing with p53, increases immunoreactive p53 and acetylated p53, and activates a p53 responsive reporter gene. Suppression of Class I MAGE proteins also induces apoptosis in MAGE-A positive, p53$^{wt/wt}$ parental HCT 116 colon cancer cells but not in a MAGE-A positive HCT 116 p53$^{-/-}$ variant, indicating that p53 is involved in MAGE suppression of apoptosis. Furthermore, treatment with MAGE specific siRNA suppresses S91 melanoma growth in vivo, specifically in syngenic DBA2 mice.

Accordingly, the present invention provides a method for inhibiting the growth or proliferation, or inducing apoptosis, of a mammalian cell that expresses a MAGE gene, the method comprising inhibiting the binding of KAP-1 to a polypeptide encoded by the MAGE gene in the cell. Preferably, the method comprising administering to the cell a substance that inhibits the formation of a complex between KAP-1 and a MAGE protein, or the function of the complex. The substance may preferably be an antibody against a complex formed between KAP-1 and a polypeptide encoded by a MAGE gene. Such antibody may preferably be a monoclonal antibody, or an active fragment thereof, in particular a humanized or human antibody in the treatment of human cells, especially a cancerous or malignant or neoplastic cell.

In one embodiment, the method of the present invention comprises inhibiting MAGE function or expression in combination with one or more chemotherapeutic agent.

The present invention further provides a method for regulating male fertility in a mammal, the method comprising inhibiting MAGE/KAP-1 formation in a male testis cell according to the method described herein.

The present invention also provides a pharmaceutical composition for treating tumor cell formation, tumor cell growth, or induction of apoptosis of a testis cell comprising a compound that inhibits the binding of KAP-1 and a polypeptide encoded by a MAGE gene and a pharmaceutically acceptable excipient.

In a further embodiment, the present invention provides a method for screening for a substance that inhibits MAGE/KAP-1 complex formation, the method comprising: (1) providing a candidate substance to be tested; (2) applying said candidate substance to a cell or protein array expressing a MAGE gene or MAGE gene construct, (3) detecting the level of MAGE/KAP-1 complex in the presence of the candidate substance, and (4) determining a level of MAGE/KAP-1 complex in the absence of the candidate substance, wherein a substance that decreases the level of MAGE/KAP-1 complex is selected to be an antagonist of MAGE/KAP-1 formation.

BRIEF DESCRIPTION OF THE DRAWINGS

FIG. 15 shows the siRNA sequences used herein.

DETAILED DESCRIPTION OF THE INVENTION

Figure 1:
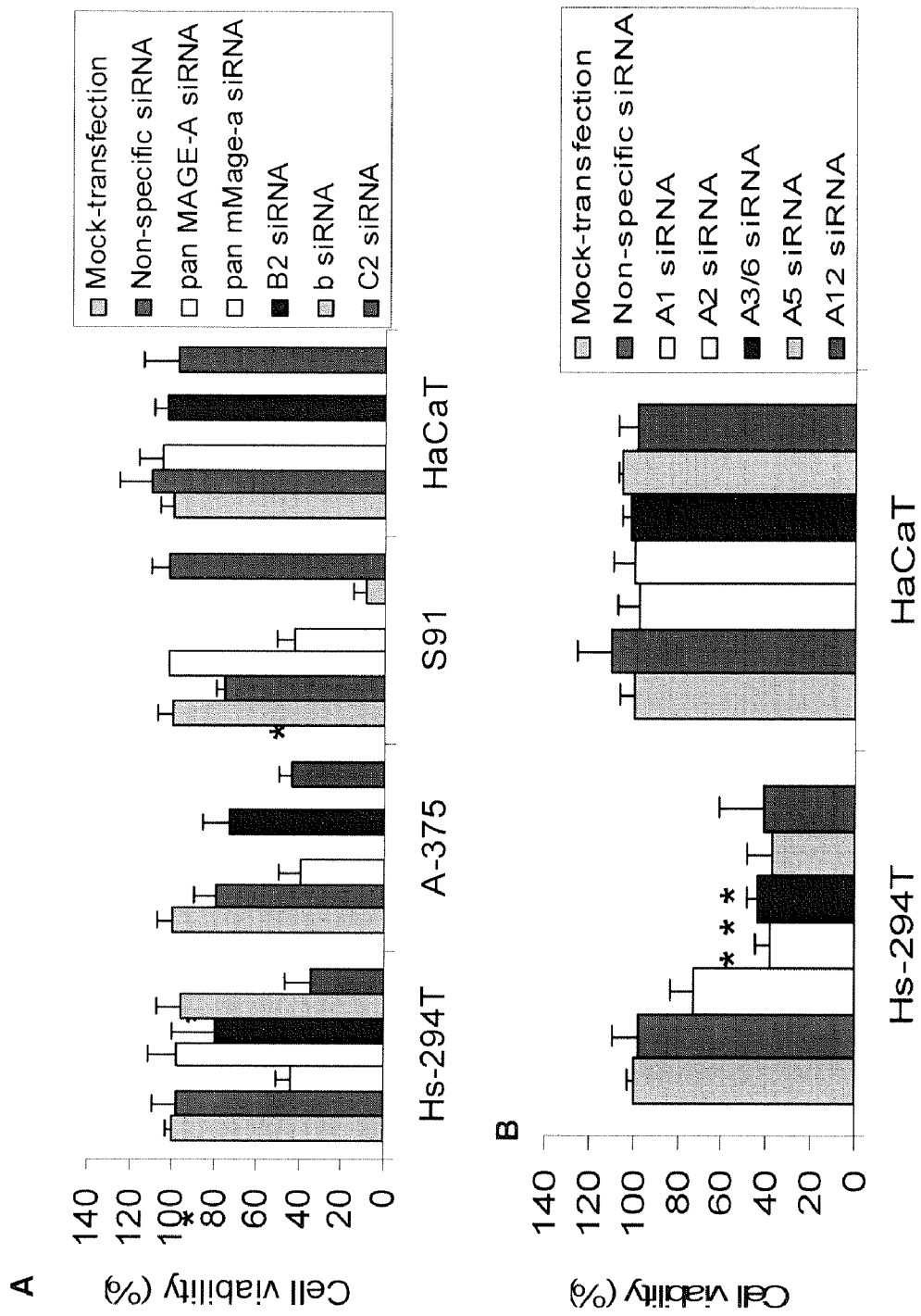
FIG. 1 shows that MAGE siRNAs inhibit melanoma growth in vitro. A. MAGE siRNA inhibits the growth of human (Hs-294T, A375) and murine (S91) melanoma cell lines but not the MAGE (−) HaCaT human keratinocyte line. Trypan blue viability was determined 72 hours post transfection with 100 nM siRNA. The blue bar represents the growth of mock-transfected cells (no siRNA) and is considered as 100% viability. Pan-MAGE-A siRNA targets all human MAGE-A sub-family members except MAGE-A1, which has significant sequence variation which makes the use of a small common set of siRNAs impossible. Pan-mMage-a and mMage-b siRNAs target all murine mMage-a and mMage-b family members, respectively. The human melanoma cell lines do not express MAGE-B and there is no murine mMage-c. * Indicates a significant difference from non-specific siRNA ($p<0.05$, T-Test). Error bars indicate s.d. Analyses were performed from at least 3 individual experiments with triplicates for each group. B. The effect of siRNAs targeting individual MAGE-A family members. C. Individual siRNA duplexes targeting different sequences in mMage-b have variable results, indicating sequence specificity. NS=non-specific control siRNA. D. MAGE siRNAs decrease expression of target proteins. For protein target validation, cells were harvest 48 hours post transfection 100 nM of indicated siRNAs. Equal amount protein of whole cell lysates was loaded. * indicates protein targeted by siRNA. NS=non-specific control siRNA; (−)=no siRNA.
Figure 1:
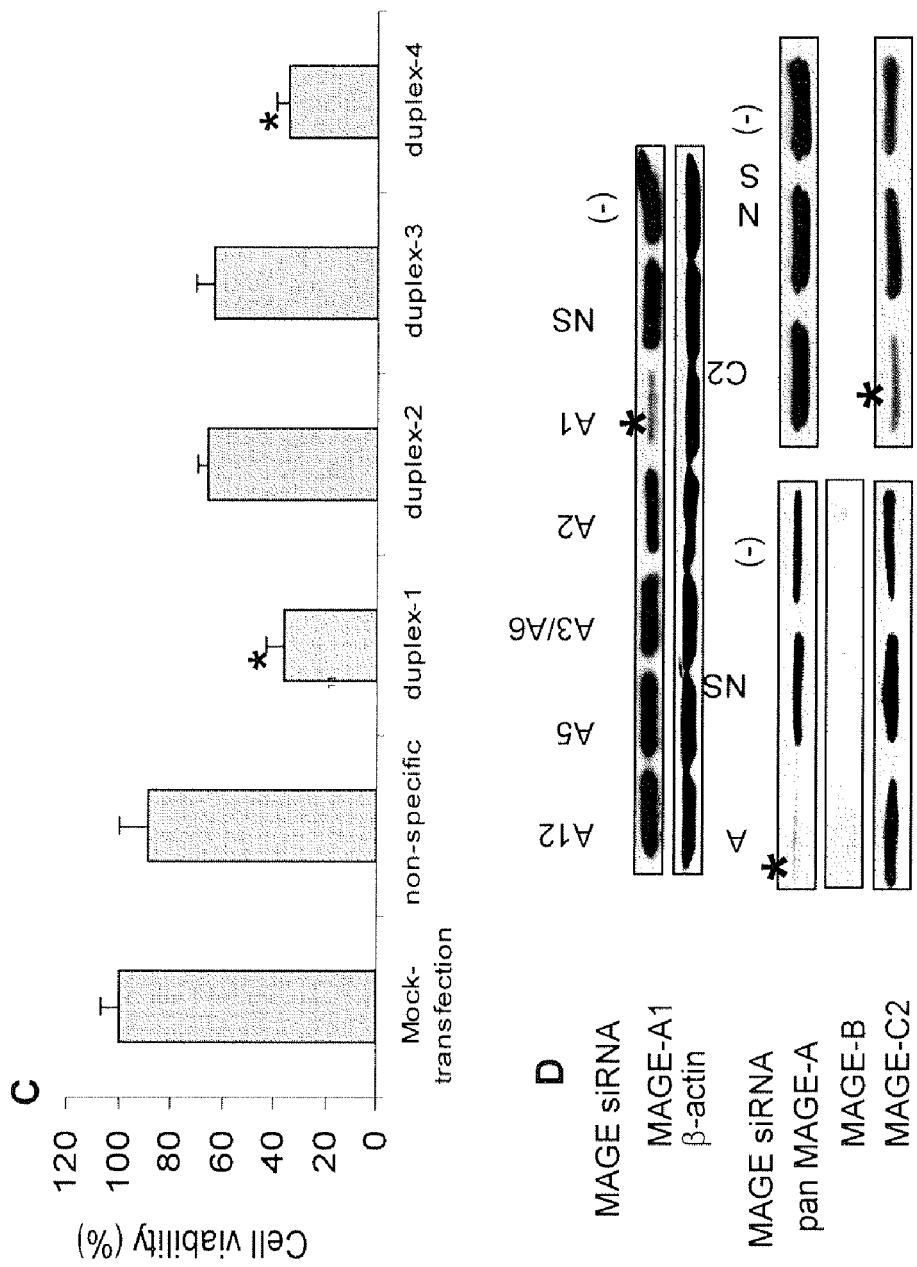

The present invention provides in one embodiment a method for screening for a substance that inhibits MAGE/KAP-1 complex formation. To identify an inhibitor in accordance with the present invention, one generally will determine the ability of a candidate substance to inhibit MAGE protein-KAP-1 complex formation. The method may generally comprise (a) providing a MAGE protein or a relevant or functional fragment or subunit thereof a and KAP-1 under conditions permitting the formation of a complex, in the presence or absence of a candidate substance, and (b) assessing the formation of the complex, wherein a decrease in complex formation in the presence of a candidate substance, as compared to complex formation in the absence of the first substance, indicates that the candidate substance is an inhibitor of the MAGE protein and KAP-1 complex formation. Such assays can be performed in cell free environments, but also may be conducted in isolated cells, organs, or in living organisms, and may comprise random screening of large libraries of candidate substances.

Candidate Substances As used herein the term "candidate substance" refers to any molecule that inhibits under suitable conditions the formation of MAGE protein and KAP-1 complexes. Candidate compounds may be screened from large libraries of synthetic or naturally-occurring compounds, or fragments or parts thereof, which are readily available to those skilled in the art. It is proposed that compounds isolated from natural sources, such as animals, bacteria, fungi, plant sources, including leaves and bark, and marine samples may be assayed as candidates for the presence of potentially useful pharmaceutical agents. The candidate substance may be a macromolecule such as a protein or fragment thereof (e.g. an antibody) or a nucleic acid molecule, and may be a small molecule.

Initially identified compounds may serve as lead compounds to help develop improved compounds via "rational drug design," via comparisons with known inhibitors, and modifications based on structural and other knowledge of the lead compound and further testing. The goal of rational drug design is to produce structural analogs or derivatives of biologically active compounds. By creating such analogs, it is possible to generate drugs which are more active or stable or otherwise more pharmaceutically desirable.

A quick, inexpensive and easy assay to run is an in vitro assay. Such assays generally use isolated molecules, can be run quickly and in large numbers, thereby increasing the amount of information obtainable in a short period of time. In a straightforward embodiment, isolated MAGE protein or a suitable functional fragment thereof, are combined with isolated KAP-1 protein, and complex formation is assayed in the presence and absence of a candidate substance, under suitable conditions. The lack or reduction of complex formation in the presence of the candidate compound, as compared to in the absence of the candidate or another suitable control, indicates that the candidate substance is an inhibitor of MAGE/KAP-1 interaction or binding.

The present invention may also utilize a variety of specific assay formats. Inhibition of protein-protein interactions may be studied by using biochemical and immunologic techniques, such as fluorescence energy transfer where different molecules are both labeled with appropriate fluorescent donor-acceptor pairs, co-immunoprecipitation, double-determinant Western blot and ELISAs (e.g., sandwich ELISA), which are well known to those skilled in the art.

Fluorescence resonance energy transfer (FRET) is a common technique when observing the interactions of two different proteins. Change in fluorescence intensity or spectrum is an indication of the binding of the two proteins, and can be used to assay the ability of a candidate substance to inhibit the complex formation.

Label transfer can be used for screening or confirmation of protein interactions and can provide information about the interface where the interaction takes place. Label transfer can also detect weak or transient interactions that are difficult to capture using other in vitro detection strategies. In a label transfer reaction, a known protein is tagged with a detectable label. The label is then passed to an interacting protein, which can then be identified by the presence of the label.

Tandem affinity purification (TAP) detects interactions within the correct cellular environment (e.g. in the cytosol of a mammalian cell) (Rigaut et al., 1999, Nat. Biotechnol. 17:1030-2). This is a big advantage compared to the yeast two-hybrid approach. However, the TAP tag method requires two successive steps of protein purification. Thus, it can not readily detect transient protein-protein interactions.

Chemical crosslinking is often used to "fix" protein interactions in place before trying to isolate/identify interacting proteins. Common crosslinkers for this application include the non-cleavable NHS-ester crosslinker, [[bis-sulfosuccinimidyl suberate]] (BS3); a cleavable version of BS3, dithiobis (sulfosuccinimidyl propionate) (DTSSP); and the imidoester crosslinker dimethyl dithiobispropionimidate (DTBP) that is popular for fixing interactions in ChIP assays.

Quantitative immunoprecipitation combined with knockdown (QUICK) relies on co-immunoprecipitation, quantitative mass spectrometry (SILAC) and RNA interference (RNAi). This method detects interactions among endogenous non-tagged proteins (Selbach et al., 2006, Nat. Methods. 3:981-983). Thus, it has the same high confidence as co-immunoprecipitation. However, this method also depends on the availability of suitable antibodies.

Dual Polarisation Interferometry (DPI) can be used to measure protein-protein interactions. DPI provides real-time, high-resolution measurements of molecular size, density and mass. While tagging is not necessary, one of the protein species must be immobilized on the surface of a waveguide.

Static Light Scattering (SLS) measures changes in the Raleigh scattering of protein complexes in solution and can non-destructively characterize both weak and strong interactions without tagging or immobilization of the protein. The measurement consists of mixing a series of aliquots of different concentrations or compositions with the anylate, measuring the effect changes in light scattering as a result of the interaction, and fitting to a model. Weak, non-specific interactions are typically characterized via the second virial coefficient. This type of analysis can determine the equilibrium association constant for associated complexes (Attri et al., 2005, Analyt. Biochem. 346(1):132-138).

The present invention also contemplates the screening of compounds for their ability to inhibit MAGE protein/KAP-1 complexes formation in cells. Various cell lines can be utilized for such screening assays, including cells specifically engineered for this purpose. In addition, genetic constructs for use in transforming cells for such assays may also be used.

In vivo assays involve the use of various animal models of cancers with active or enhanced MAGE expression. Treatment of animals with test compounds will involve the administration of the compound, in an appropriate form, to the animal. Administration will be by any route that could be utilized for clinical purposes. Determining the effectiveness of a compound in vivo may involve a variety of different criteria. Also, measuring toxicity and dose response can be performed in animals in a more meaningful fashion than in vitro or in cyto assays.

Preferably, a yeast or mammalian two-hybrid screen (See: for example, U.S. Pat. No. 5,283,173) system may be adopted. The system uses a native MAGE protein or a variant thereof, and KAP-1 or a variant thereof, fusion proteins, where MAGE is fused to the DNA binding domain and KAP-1 is fused to the activation domain. However, the assay could also be configured with MAGE fused to the activation domain and KAP-1 fused to the DNA binding domain. Compounds are preferably selected based on their ability to block (or inhibit) yeast growth or reporter gene expression in yeast or mammalian cells. Preferred reporter gene includes those encoding β-galactosidase synthesis (blue color), chloramphenicol acetyltransferase (CAT), luciferase, or other fluorescent proteins (e.g. GFP). Preferably, the yeast cell is permeabilized (Gaber, et al., Mol. Cell. Biol. 9: 3447-3456 (1989)). It is appreciated that certain modification to the basic dihybrid screen may be desirable, such as, substituting other DNA binding and activation domains for those contributed by GAL-4 (e.g., lexA DNA binding domain is also contemplated for use in this invention. In addition inducible promoters can be used to drive expression in the two hybrid screens of this invention.

Two-hybrid based screening method of the present invention for MAGE/KAP-1 binding inhibitors may be devised using a high-throughput, microtiter-formatted, robotics-amenable system. Candidate compounds may be seeded individually at a suitable concentration (e.g. 25 µg/ml) with 2% galactose to induce yeast protein expression and hybrid formation. Yeast or mammalian cells pre-grown in selective media containing the neutral carbon source raffinose are added, and the increase in candidate gene expression such as beta-gal activity (yeast two hybrid method) or chloramphenicol acetyl transferase (CAT) or Luciferase (mammalian two hybrid methods) are measured following incubation. Percent inhibition may be calculated, and a differential value determined with respect to a parallel control two-hybrid strain. The control strain should be the same parent yeast strain or cell line containing plasmids encoding the two proteins without any addition of the candidate compounds, or two other proteins that are known to interact.

Modification to the above may include, but are not limited to, different yeast strains or transfectants with different transcriptional reporters (i.e. auxotrophic markers like URA3), a different two-hybrid system (Fields, et al., (1989) Nature 340:245-247), and different promoters on the plasmids.

In an alternative embodiment, a non-transfected cell based assay may be used for screening for antagonists of KAP-1/MAGE binding. This would allow the identification of antagonists that would function inside the cell. Specifically, a MAGE positive cell line is cultivated in the presence and absence of a candidate compound, and the viability of the cells are measured. Compounds that cause the cells to lose viability are identified, and their ability to inhibit MAGE/KAP-1 binding confirmed by assaying the cells cultured in the presence of these compounds for the absence of MAGE/KAP-1 complex, e.g. by immuno-precipitation assays.

Alternatively, instead of measuring cell viability/growth rate, p53 level and/or ubiquitination and degradation by immunoblotting, p53 acetylation, over even p53 transcription, p53 function, and recruitment of histone deacetylases may be assayed as an indication that KAP-1/MAGEbinding has been inhibited, followed by confirmation of the lack of KAP-1/MAGE complex by e.g. immuno-precipitation assays.

Inhibitors can be discovered directly in vitro with purified MAGE and KAP-1. If in the presence of a candidate compound a MAGE/KAP-1 complex fails to form in vitro, while in the absence of the candidate the complex forms under otherwise identical conditions, then the candidate compound would be considered an inhibitor of MAGE and KAP-1 binding.

There are many ways to configure an assay. For example, a 96-well plate in which one of the binding partners, preferably purified recombinant proteins, is initially added to the wells of an ELISA plate, followed by an additional incubation with a non-specific protein such as BSA (bovine serum albumin) to block free binding sites on the plastic. Subsequently a solution containing the putative inhibitor or control buffer is added mixed with a solution containing the other binding partner and incubated so as to allow complete binding of MAGE to KAP-1 in the control buffer well. The complex so formed in each well is then measured. This may be accomplished e.g. by either labeling one of the binding partners and then detect the complex directly, e.g. by electrophoresis, or detect the complex using an antibody specific for the complex.

The present invention provides a method for inhibiting the growth or proliferation, or inducing apoptosis, of a cell that expresses a MAGE gene, the method comprising inhibiting the formation MAGE gene product with KAP-1, thereby inhibiting the function the MAGE gene in the cell.

Suitable MAGE genes for the present invention may be a Type I MAGE gene, such a MAGE-A, MAGE-B, or MAGE-C, specifically, MAGE, A3, A5, A6, A8, A9, A10, A11 or A12, or MAGE-B1, B2, B3 or B4, or MAGE-C1, or C2. The MAGE gene may also be a Type II MAGE gene, such as Necdin, MAGE-D, MAGE-E (E1), MAGE-F, MAGE-G, or MAGE-H.

In preferred embodiments, the method inhibits MAGE gene function in a cell A which is a cancerous or malignant or neoplastic cell. Preferably, wherein the cancer, tumor, or cellular proliferation is selected from the group consisting of melanomas, Multiple Myeloma and other plasma cell dyscrasias, lymphoma, T-cell leukemia, non-small cell lung carcinoma, hepatic carcinoma, gastric cancer, esophagus carcinomas, colorectal carcinomas, pancreatic endocrine neoplasms, ovarian neoplasms, cervical cancer, salivary glands carcinoma, head and neck squamous cell carcinomas, proliferating testes cells, spermatocytic seminoma, sporadic medullary thyroid carcinoma, osteosarcomas, childhood astrocytomas, bladder cancer, cells from inflamed joints in juvenile rheumatoid arthritis or other harmful inflammatory condition, glioma, neuroblastoma tumors, and cancers related to malignant mast cells.

The present invention provides antagonist compositions and methods that inhibit MAGE protein from binding to KAP-1.

As the function or development of male germ cells also depends on the proper function of MAGE gene products, inhibition of MAGE protein binding to KAP-1 in these cells will prevent them from developing or functioning normally. Accordingly, an embodiment of the present invention provides contraceptive methods and compositions for male mammals, especially in man. Preferably, the contraceptive methods comprise administering to the mammal in need thereof a composition comprising one or more antagonists of MAGE protein/KAP-1 binding, such as a small molecule antagonist, siRNA, an antibody against a MAGE gene product, or an antisense nucleic acid molecule.

The antagonists of the invention (neutralizing and others) are preferably used as a treatment for cancer formation or growth. By the term "neutralizing" it shall be understood that the antagonist has the ability to inhibit or block the binding of MAGE to KAP-1.

An anti-MAGE antibody suitable for the present invention may be a polyclonal antibody. Preferably, the antibody is a monoclonal antibody. The antibody may also be isoform-specific. The monoclonal antibody or binding fragment thereof of the invention may be Fab fragments, F(ab)$_2$ fragments, Fab' fragments, F(ab')$_2$ fragments, Fd fragments, Fd' fragments or Fv fragments. Domain antibodies (dAbs) (for review, see Holt et al., 2003, Trends in Biotechnology 21:484-490) are also suitable for the methods of the present invention.

Various methods of producing antibodies with a known antigen are well-known to those ordinarily skilled in the art (see for example, Harlow and Lane, 1988, Antibodies: A Laboratory Manual. Cold Spring Harbor Laboratory Press, Cold Spring Harbor, N.Y.; see also WO 01/25437). In particular, suitable antibodies may be produced by chemical synthesis, by intracellular immunization (i.e., intrabody technology), or preferably, by recombinant expression techniques. Methods of producing antibodies may further include the hybridoma technology well-known in the art.

In accordance with the present invention, the antibodies or binding fragments thereof may be characterized as those which are capable of specific binding to a MAGE protein/KAP-1 complex or an antigenic fragment thereof, preferably an epitope that is recognized by an antibody when the antibody is administered in vivo. Antibodies can be elicited in an animal host by immunization with a MAGE/KAP-1 complex-derived immunogenic component, or can be formed by in vitro immunization (sensitization) of immune cells. The antibodies can also be produced in recombinant systems in which the appropriate cell lines are transformed, transfected, infected or transduced with appropriate antibody-encoding DNA. Alternatively, the antibodies can be constructed by biochemical reconstitution of purified heavy and light chains.

The antibodies may be from humans, or from animals other than humans, preferably mammals, such as rat, mouse, guinea pig, rabbit, goat, sheep, and pig. Preferred are mouse monoclonal antibodies and antigen-binding fragments or portions thereof. In addition, chimeric antibodies and hybrid antibodies are embraced by the present invention. Techniques for the production of chimeric antibodies are described in e.g. Morrison et al., 1984, Proc. Natl. Acad. Sci. USA, 81:6851-6855; Neuberger et al., 1984, Nature, 312:604-608; and Takeda et al., 1985, Nature, 314:452-454.

Further, single chain antibodies are also suitable for the present invention (e.g., U.S. Pat. Nos. 5,476,786 and 5,132,405 to Huston; Huston et al., 1988, Proc. Natl. Acad. Sci. USA, 85:5879-5883; U.S. Pat. No. 4,946,778 to Ladner et al.; Bird, 1988, Science, 242:423-426 and Ward et al., 1989, Nature, 334:544-546). Single chain antibodies are formed by linking the heavy and light immunoglobulin chain fragments of the Fv region via an amino acid bridge, resulting in a single chain polypeptide. Univalent antibodies are also embraced by the present invention.

Many routes of delivery are known to the skilled artisan for delivery of anti-MAGE antibodies. For example, direct injection may be suitable for delivering the antibody to the site of interest. It is also possible to utilize liposomes with antibodies in their membranes to specifically deliver the liposome to the area of the tumor where MAGE expression or function is to be inhibited. These liposomes can be produced such that they contain, in addition to monoclonal antibody, other therapeutic agents, such as those described above, which would then be released at the tumor site (e.g., Wolff et al., 1984, Biochem. Biophys. Acta, 802:259).

The following examples are intended to illustrate preferred embodiments of the invention and should not be interpreted to limit the scope of the invention as defined in the claims.

EXAMPLES

Materials and Methods

Cell lines: The Hs-294T, A375 and S91 melanoma cell lines were purchased from ATCC (Manassas, Va.). p53RE-bla HCT-116 cell was purchased from Invitrogen (Invitrogen, Carlsbad, Calif.), and HCT 116 $p53^{wt/wt}$ or $p53^{-/-}$ cell lines were kindly provided by Bert Vogelstein (The Johns Hopkins University School of Medicine, Baltimore, Md.). The HMC1 malignant mast cell line was kindly provided by Dr. J. H. Butterfield, The Mayo Clinic, Rochester, Minn. (18).

siRNA: All siRNA preparations were siStable or siS-TABLE-Plus (conjugated to cholesterol at the 5' end of the sense strand) siRNA purchased from Dharmacon Inc., Boulder, Colo. In some in vivo studies we used PEI complexed siRNA (JET-PEI, PolyPlus Transfection, Illkirch, France). The specific targets for each individual siRNAs were described in Yang et al (17). Sequences of siRNA sequences are given in FIG. 14.

Antibodies: For human target validation studies and immunoprecipitation we used: pan-MAGE-A monoclonal (Zymed laboratories Inc, South San Francisco, Calif.), anti-MAGE-A1 monoclonal (Santa Cruz, Santa Cruz, Calif.), anti-MAGE-B2 (polyclonal, Santa Cruz, Santa Cruz, Calif.) or anti-human MAGE-C2 monoclonal (Ludwig Institute for Cancer Research, New York, N.Y.), anti-human KAP1 (polyclonal, Novus, Biologicals, Littleton, Colo., recognizing the N-terminal region 1-50 amino acids of KAP1), anti-human KAP1 (polyclonal, supplied by Dr. Frank J. Rauscher III, recognizing the C-terminal PHD-Bromo domains of KAP1), anti-human p53 (Biosource, Camarillo, Calif.), anti-human Lamin B1 (Santa Cruz, Santa Cruz, Calif.). Anti-FLAG (Monoclonal, Sigma, St Louis, Mo.) and anti-V5 (Invitrogen, Carlsbad, Calif.) were used to detect expression of recombinant proteins. Non-specific mouse or rabbit IgG (Monoclonal, Sigma, St Louis, Mo.) was used as a control for immunoprecipitation. Antibodies specific for mouse Mage proteins expressed by the cells in these experiments were not available.

Expression Vectors: V5-Tagged mMage-b was expressed using pcDNA3.1/V5-TOPO vector from Invitrogen (19). V5-Tagged MAGE-A3 was expressed using the T-Rex viral power lentivirus system (Invitrogen). FLAG-Tagged MAGE-C2 was expressed using pFLAG-CMV-2 (Sigma). FLAG-Tagged KAP1 cDNAs with various deletions were made in the Rauscher lab and expressed using pcDNA3.1.

siRNA Transfection and Cell Viability: In vitro studies used Lipofectamine™ 2000 (Invitrogen, Carlsbad, Calif.) as a transfection reagent and all transfections were performed under a Rnase-free condition. The final siRNA concentrations were 50, 100 or 150 nM. Cell viability was determined 72 hours after transfection by counting cells that excluded trypan blue. In selected experiments, cell viability was also determined by MTT [3-(4,5-dimethylthiazol-2-yl)-2,5-diphenyltetrazolium bromide assay (Sigma, St. Louis, Mo.) which showed similar results to the Trypan Blue assay (data not shown).

Target Validation and Specificity: Confirmation of cleavage of mRNA induced by siRNA was previously documented (17). Target protein suppression was validated by immunoblotting forty-eight hours post transfection (FIG. 1D).

Apoptosis Assays: Apoptosis was determined by morphologic analysis following staining with acridine orange and ethidium bromide (17), or by APO-BrdU™ TUNEL assay (Molecular Probes, Eugene, Oreg.). Both assays were performed approximately one half doubling time after transfection with a final siRNA concentration of 100 nM.

Identification of MAGE Binding Partners: The human MAGE-C2 (NM_016249, previously called MAGE-E1) was used as a bait protein and the Clontech YEASTMAKER kit was used to construct a cDNA library from mRNA of the HMC1.1 malignant mast cell line. $1.2 \times 10^6$ independent transformants were obtained, yielding 86 colonies, of which 51 showed β-galactosidase activity and were sequenced. KAP1 (Trim 28) was identified as a potential partner of MAGE-C2. The endogenous binding between KAP1 and MAGE proteins was confirmed in human melanoma cells by immunoprecipitation (IP) with anti-KAP1 or anti-MAGE antibody followed by immunoblotted with anti-MAGE or anti-KAP1 antibodies. Since there is neither mouse mMage-b nor individual human MAGE-A3 antibody available, we expressed V5-Tagged mMage-b from an expression plasmid and induced V5-Tagged MAGE-A3 expression by transducing lentivirus into mammalian cells. Cell lysates were then immunoprecipitated with anti-KAP1 antibody and MAGE proteins were detected with anti-V5 antibody.

To identify the KAP1 binding domain for MAGE-C2 and mMage-b, COS-7 cells were co-transfected with MAGE-C2 or V-5-mMage-b expression plasmids and with plasmids expressing full or partial length KAP1. Lysates were immunoprecipitated with anti MAGE-C2 or V5 antibody and blotted with antibodies recognizing either the N- or the C-terminal region of KAP1.

P53 and acetylated p53 Cytoblots: To determine the amount of acetylated p53 and total p53 levels in cells treated with siRNA we used the cytoblot technique (20). Cells are plated at 20,000 cells per well using a uFill reagent dispenser (Biotek Instruments, Inc.), allowed to attach overnight, and treated with siRNA. Following treatment, the cells are fixed by addition of 100 ul of 3.7% formaldehyde using a Biomek FX liquid handler (Beckman Coulter, Inc.). The plates are incubated for 20 minutes at 4 degrees and cells are washed 5× in 100 ul of PBS pH 7.4 containing 0.1% Triton X-100 using a Biomek FX liquid handler to permeabilize cell membranes. Following permeabilization, cells are incubated in 100 uL/well of Odyssey Blocking Buffer (Licor, Inc.) for 1 hour at room temperature with gentle rotation. Each well is incubated with 100 uL per well anti-p53 antibodies (Cell Signaling Technologies) at a 1:1000 dilution in Odyssey Blocking Buffer for one hour, followed by incubation with anti-p53 or anti-acetylated p53 antibodies (Cell Signaling Technologies) at a 1:1000 dilution in Odyssey Blocking Buffer for one hour. Secondary antibody incubations are carried out simultaneously by addition of 100 uL per well containing 1:5000 dilution of 680 nM dye conjugated anti mouse secondary antibody (Licor, Inc.) and 1:5000 dilution of 800 nM dye conjugated anti-rabbit secondary antibody (Licor, Inc.) for 1 hour. Following incubation, plates are washed 6× using a Biotek Instruments microplate washer. All liquid is removed and plates are imaged on a Licor Odyssey microplate imager at the 700 and 800 nM channels. All raw data is quantified using the Licor In-Cell Western Analysis Software (Licor, Inc.). To normalize the raw antibody values to cell number, the fixed cells are incubated with Sytox Green dye (Invitrogen) at a dilution of 1:10,000 in PBS for 15 minutes at 37 degrees. Sytox green is quantified by reading the plate on a Safire II plate reader (Tecan, Inc.) for green fluorescence (Ex 485 nM/Em 535 nm). All raw antibody data is normalized to the Sytox green signal. Fold differences are calculated by dividing control cells that were treated with solvent only by the normalized antibody data.

P53 activation assay: To determine if MAGE gene knockdown affects the activity of p53, we utilized Invitrogen's GeneBLAzer® cell signaling pathway specific CellSensor® cell line, HCT-116 p53-BLA containing the GeneBLAzer® betalactamase (bla) Reporter Technology. When the p53 pathway is activated or inhibited, beta-lactamase reporter activity is modulated and can be measured quantitatively and selectively with the LiveBLAzer™-FRET B/G Loading Substrate (InVitrogen). 12,000 cells per well are plated in each well of 384 well microplates using a uFill Reagent Dispenser (BioTek Instruments, Inc.). Cells are treated with siRNA and loaded with 8 uL FRET B/G Loading Substrate (InVitrogen) engineered fluorescent substrate containing two fluorophores, coumarin and fluorescein. In the absence of bla expression, the substrate molecule remains intact. In this state, excitation of the coumarin results in fluorescence resonance energy transfer to the fluorescein moiety and emission of green light. However, when bla is expressed, the substrate is cleaved, separating the fluorophores, and disrupting energy transfer. Excitation of the coumarin in the presence of enzyme bla activity results in a blue fluorescence signal. The resulting coumarin:fluorescein ratio provides a normalized reporter response which can minimize experimental noise that can mask the underlying biological response of interest. Beta lactamase assays were read in a Safire II microplate reader (Tecan, Inc.) at excitation 409 and emissions 460 nM and 535 nM.

In vivo Studies: S91 murine melanoma cells were injected subcutaneously into the flanks of syngenic DBA/2 mice. In one protocol, cells were transfected with 100 nM siSTABLE-PLUS mMage-b siRNA or 100 nM control siSTABLE-PLUS siRNA in Lipofectamine™ 2000 prior to inoculation. After 8 hours, equal numbers of viable cells were injected subcutaneously into the flanks of DBA/2 mice and tumor growth was followed as described (17). In additional protocols, untreated S91 cells were injected subcutaneously on day "0" and then the mice were treated with multiple intra-tumoral or intraperitoneal injections of stabilized siRNA complexed with PEI or conjugated to cholesterol.

Tumor growth was followed as previously described (17). Briefly, mice were palpated for tumors by two blinded independent investigators beginning on day 5. When tumors reached measurable size, a digital venires caliper was used to take two measurements at 90° to each other and the square root of the product was calculated to give an estimate of the mean tumor diameter, and each mouse was followed either until tumor reached the target diameter or for 45 days, when animals were sacrificed as required by protocol. All procedures were approved by the Institutional Review Board and performed in accordance with the guidelines of the Animal Care Committee.

Statistical Analyses: Student's T-test was used for cell viability. The data show mean±s.d. from triplicates of each experiment, and each experiment was done at least three times independently, except as indicated for some specificity studies which were done twice. For the in vivo experiments, the time for a tumor to reach the target mean tumor diameter of 13 mm was defined as the elapsed time from the date of cell implantation to the date when a 13 mm target diameter was reached, or when the mouse was sacrificed which is considered censored. Kaplan-Meier survival analysis with the corresponding Log-Rank analysis was performed using S-plus Software (Insightful; Seattle, Wash.). Linear Regression analysis was used to measure the rate of mean tumor diameter growth as a function of time using S-plus Software (Insightful; Seattle, Wash.).

Example 1

Suppression of MAGE Genes Inhibits Tumor Cell Viability

Figure 7:
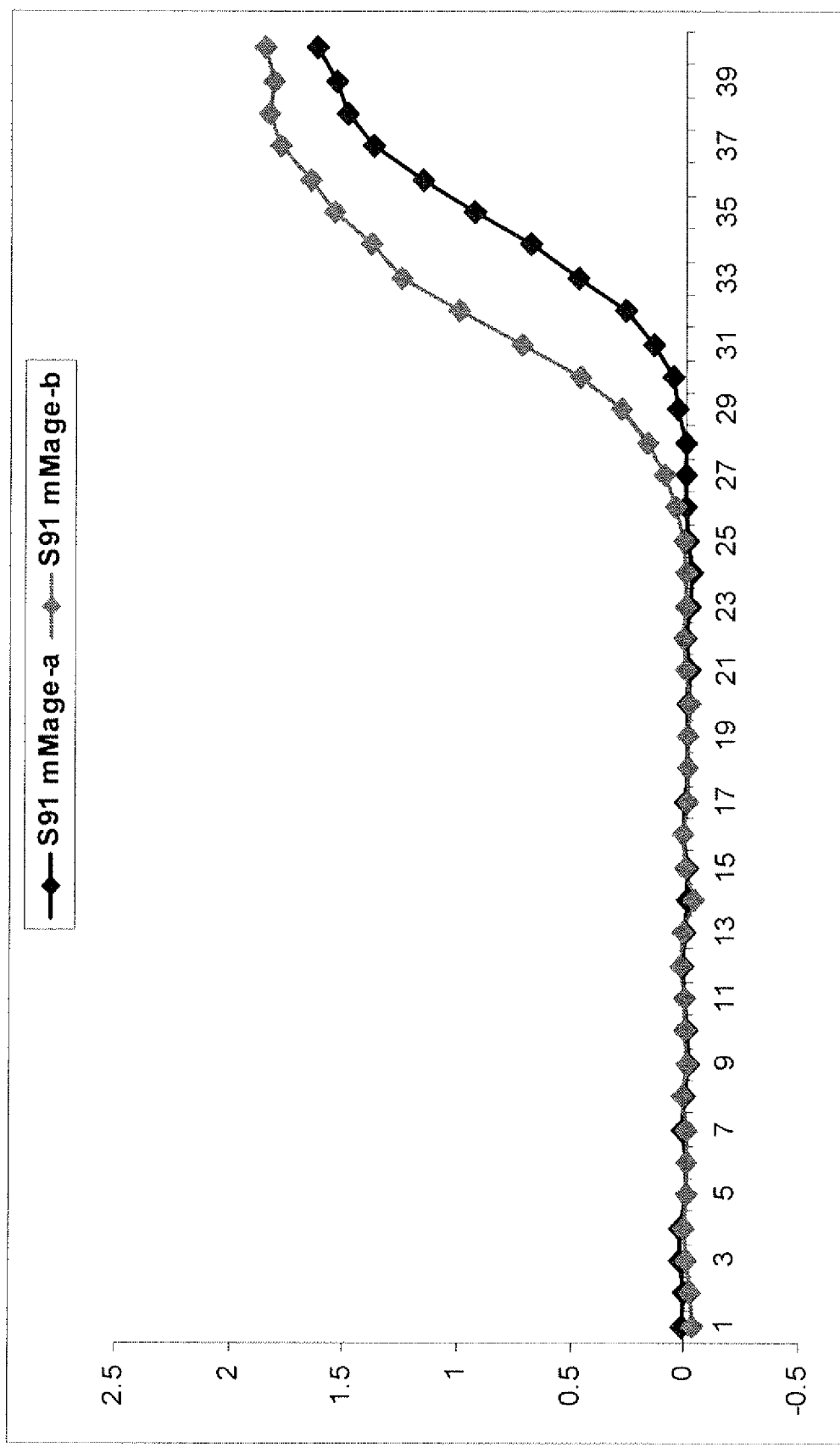
FIG. 7 shows real time RT-PCR quantification of murine mMage-a and mMage-b mRNA, indicating that mMage-b has higher expression than mMage-a at mRNA level in S91 cells.

Working with human melanoma cell lines that express MAGE-A and MAGE-C2 proteins, and with a murine melanoma cell line that expresses mMage-b, we found that transfection with siRNAs targeting several MAGE genes decreased cell viability compared to the same cells transfected with control siRNA (FIG. 1). Because of the high degree of homology of many MAGE family members and the lack of antibodies recognizing specific MAGE family members, we used siRNAs that target whole sub-families as well as siRNAs that target individual MAGE genes. FIG. 1A shows significant growth inhibition of human melanoma cells by siRNAs targeting common regions of the human MAGE-A gene family or targeting the human MAGE-C2 gene, but no significant effect with siRNA targeting the MAGE-B family members, which are not significantly expressed by these cells (FIG. 1D). In contrast, mMage-b siRNA inhibits the viability of the murine S91 cell line, which expresses significantly more mMage-b than mMage-a (FIG. 7). FIG. 1B shows siRNAs targeting unique sequences in several individual MAGE-A family members also effectively inhibit cell viability, except for MAGE-A1, which differs significantly from the other MAGE-A family members. FIG. 1C shows individual siRNA duplexes targeting different sequences in mMage-b have variable effects, indicating sequence specificity. Note that these siRNA reagents are species specific and have been previously shown to specifically destroy their target mRNAs (17). FIG. 1D shows that the siRNAs specifically suppress the targeted MAGE proteins.

Example 2

Suppression of MAGE Genes Induces Apoptosis

Figure 2:
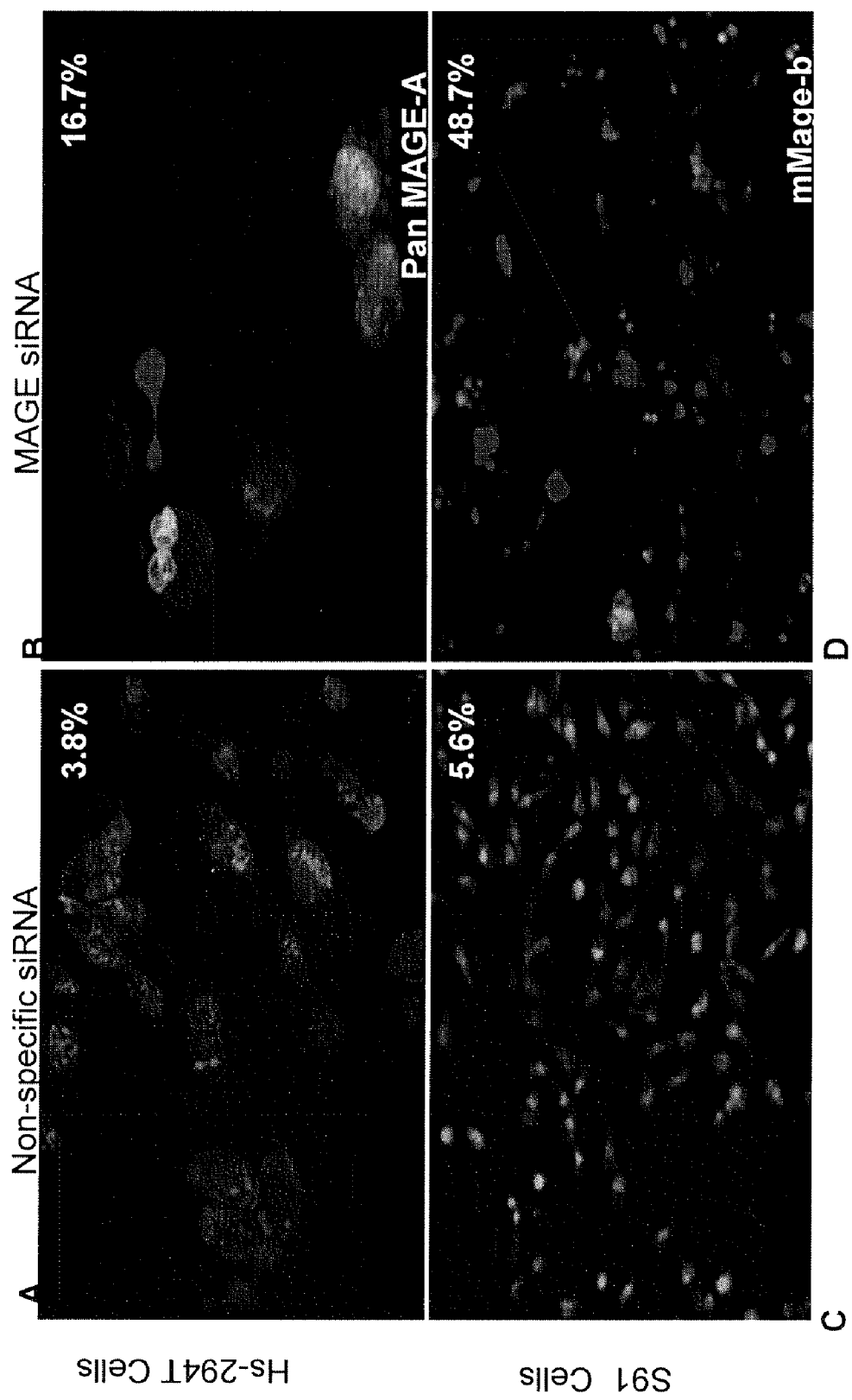
FIG. 2 shows that Class I MAGE gene knockdown induces apoptosis in melanoma cells. Fluorescence microscopy of acridine orange-ethidium bromide stained cells shows green fluorescence of live cells and red fluorescence of dead cells. Apoptotic cells show condensed or fragmented nuclei. 2A, 2B: Hs-294T cells; 2C, 2D: S91 cells. Original magnification 200× (2A, 2B) or 100× (2C, 2D). Differences between numbers of apoptotic cells in MAGE siRNA treated cells vs. non-specific siRNA treated cells were significant ($p<0.05$, T-Test for both Hs-294T and S91), n=3.
Figure 8:
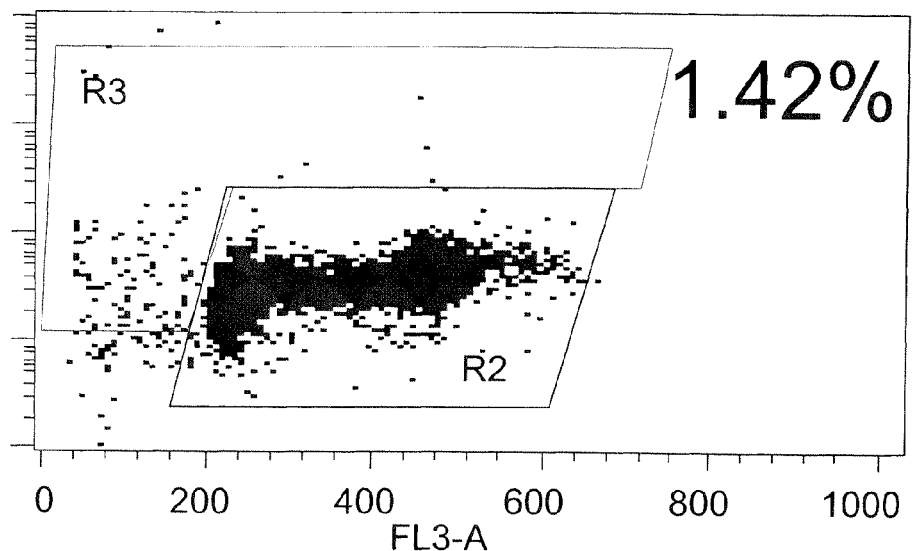
FIG. 8 shows the results of Tunnel Analysis, showing that MAGE siRNAs induced caspase-independent apoptosis in melanoma cells (TUNEL Analysis). Flow cytometry shows that apoptosis induced by MAGE siRNA in human Hs-294T (A) and murine S91 cells (B) is not inhibited by the general caspase inhibitor zVAD-FMK. Apoptotic cells are in upper, L-shaped window. The percentage of apoptotic cells is shown for each condition in the upper right corner of the individual panels.
Figure 8:
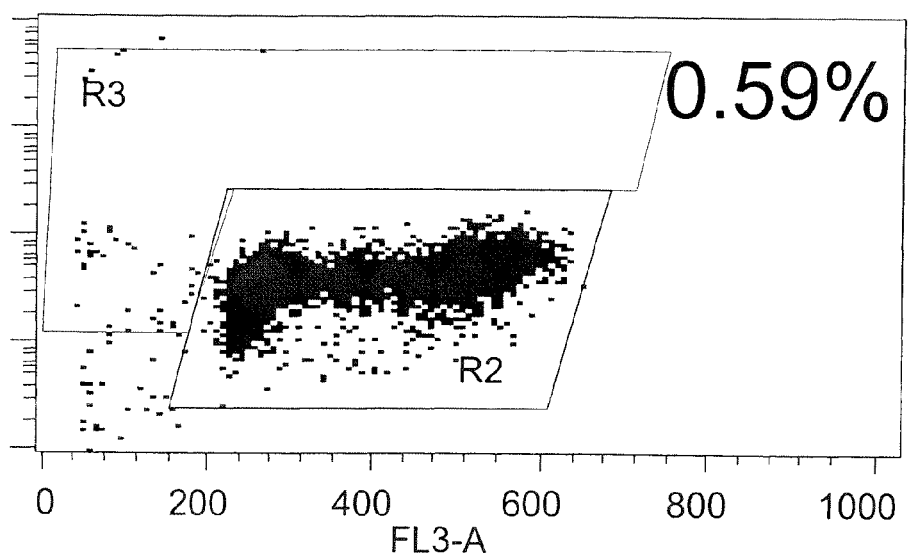
Figure 8:
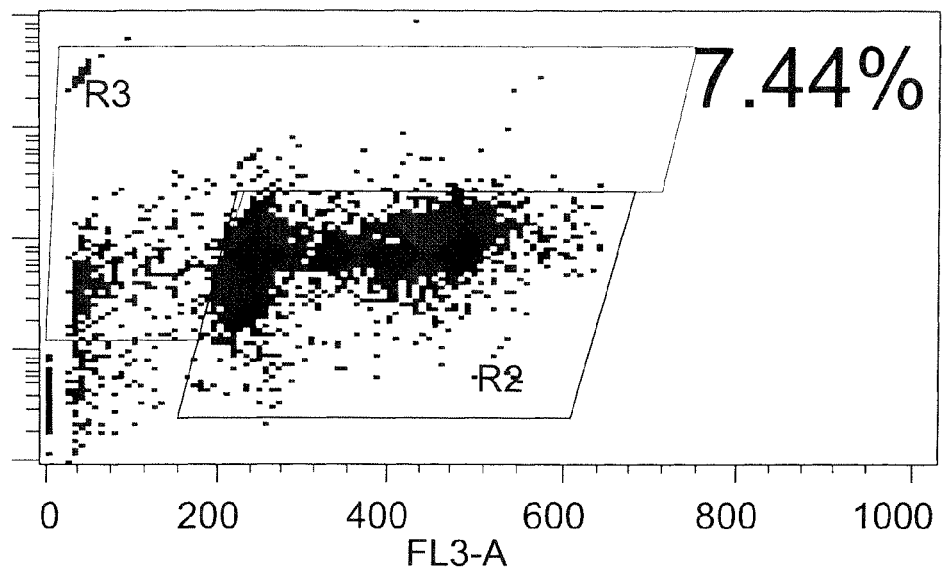
Figure 8:
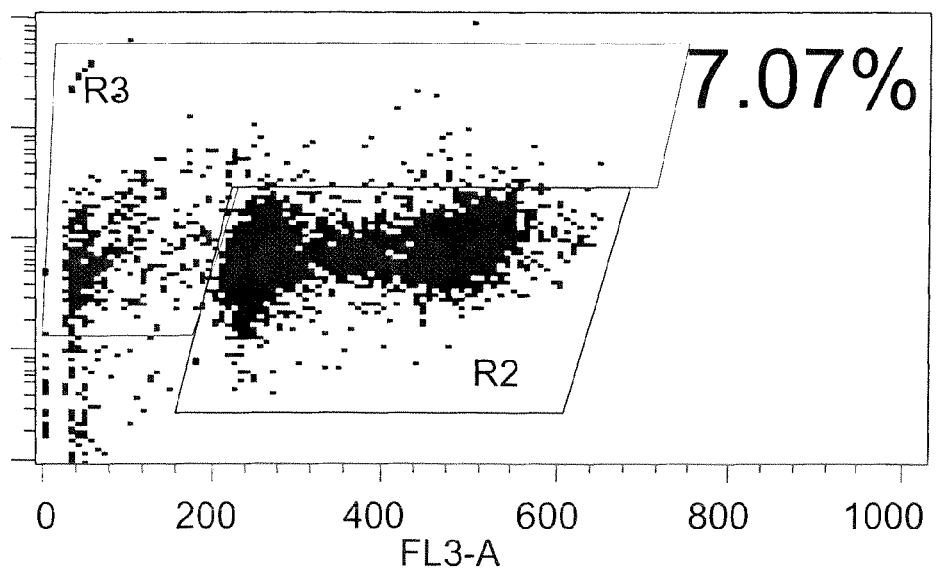
Figure 8:
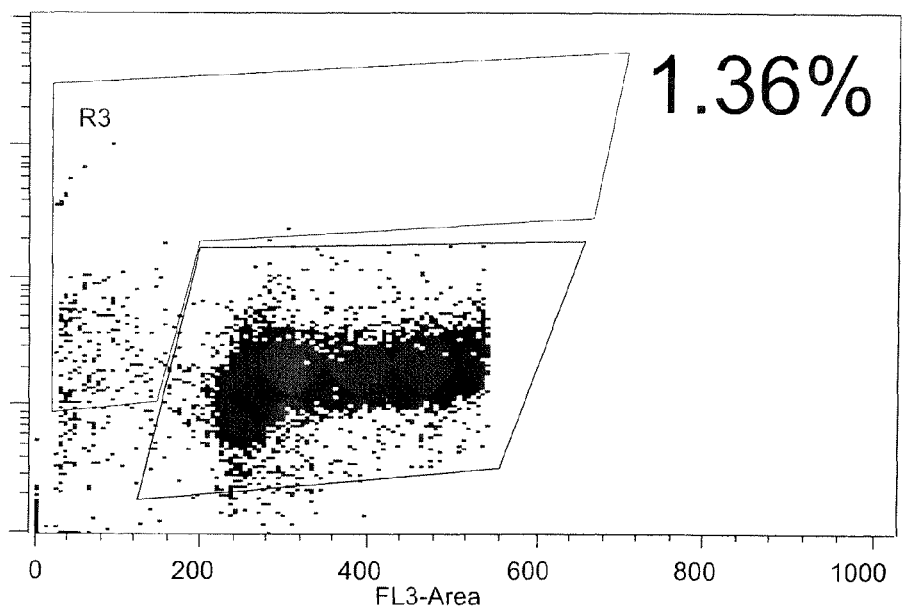
Figure 8:
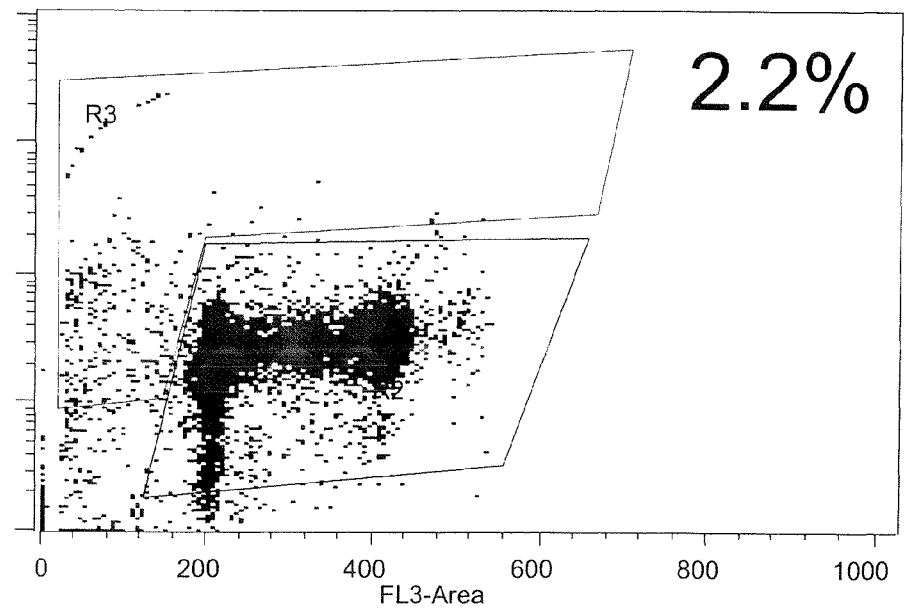
Figure 8:
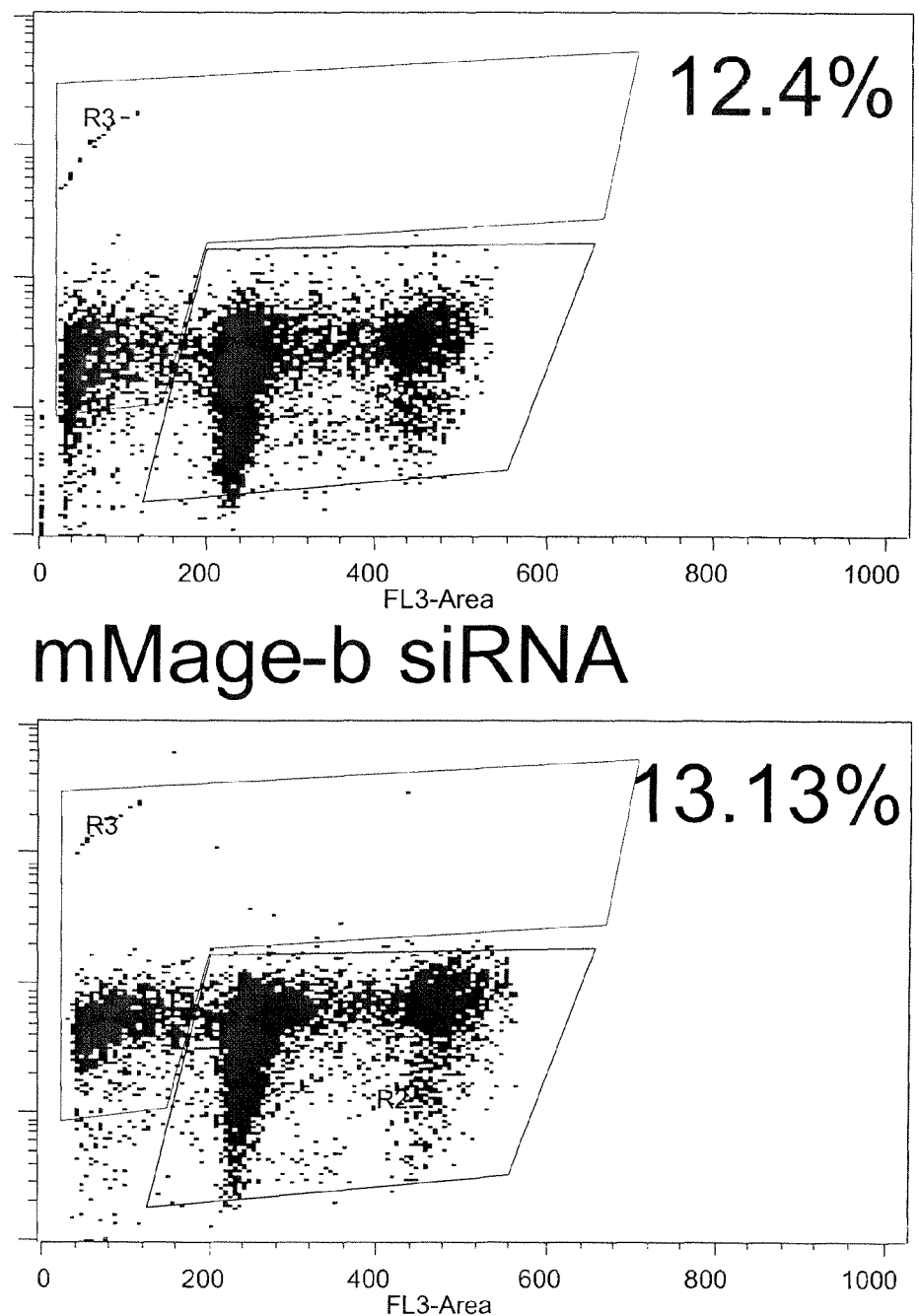

We have previously shown that suppression of MAGE genes has only modest effects on cell cycle progression in malignant mast cells (17) and preliminary studies showed similar results with melanoma cell lines (data not shown). Therefore, we focused on suppression of apoptosis as the most likely mechanism by which MAGE expression promotes survival in melanomas. We first used acridine orange/ethidium bromide staining with morphologic analysis and found that MAGE siRNA induced significant apoptosis in both human and murine melanoma cell lines (FIG. 2). TUNEL analysis with flow cytometry confirmed that MAGE siRNAs caused apoptosis (FIG. 8). Interestingly, the apoptosis was not decreased by caspase inhibitors.

Example 3

KAP1 is a Binding Partner of Multiple MAGE Proteins

Figure 9:
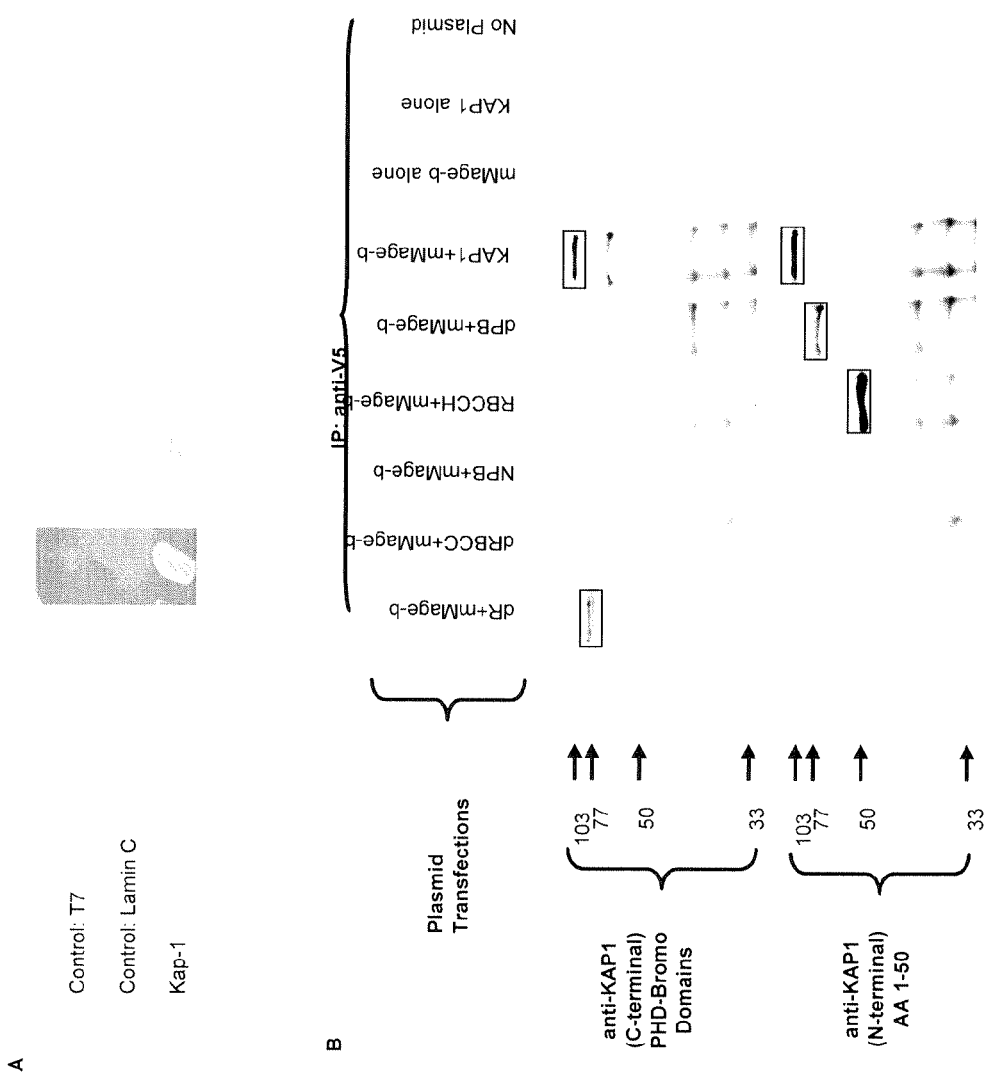
FIG. 9A shows that the yeast two hybrid assay, identifies MAGE-C2 as a Kap-1 binding partner. Yeast were co-transformed with KAP1 or control protein expression plasmids and grown on selection medium (left panel). Colonies were transferred and assayed for β-galactosidase activity (blue-green color, right panel). T7=yeast co-transformed with irrelevant bait, pGBK-T7; LaminC=yeast co-transformed with irrelevant bait, pGBKT7-LaminC; KAP1=yeast co-transformed with pGBKT7-KAP1. Note that β-galactosidase activity was only seen in the presence of Kap-1, confirming Kap-1 MAGE-C2 binding.
FIG. 9B shows that Kap-1 and mMage-b protein Co-immunoprecipitate. V5-Tagged mMage-b and KAP1 deletion expression plasmids were co-transfected into COS7 cells and lysates were immunoprecipitated with anti-V5 antibody and immunoblotted with anti-KAP1 antibodies recognizing either N-terminal or C-terminal Kap-1 peptides. The pattern is identical to that seen with MAGE-C2 (FIG. 3c) indicating that mMage-b also binds to the Kap-1 BB-Coiled coil region.

To identify the mechanism by which MAGE gene expression could suppress apoptosis, we looked for potential MAGE binding partners using a yeast two hybrid assay with MAGE-C2 as bait. KAP1 bound to MAGE-C2 in the yeast assay (FIG. 9) and was confirmed as an endogenous MAGE-C2 binding partner by co-immunoprecipitation from human melanoma cells (FIG. 3A), and in human malignant mast cells (data not shown). We next sought to determine whether other MAGE molecules could bind to KAP1 by immunoprecipitation of endogenous and expression-tagged MAGE proteins. We found we could bring down KAP1 with endogenous MAGE-A using a pan-anti-MAGE-A antibody and that we could also bring down V5-tagged human MAGE-A3 and V5-tagged murine mMage-b with KAP1 (also FIG. 3A).

Figure 3:
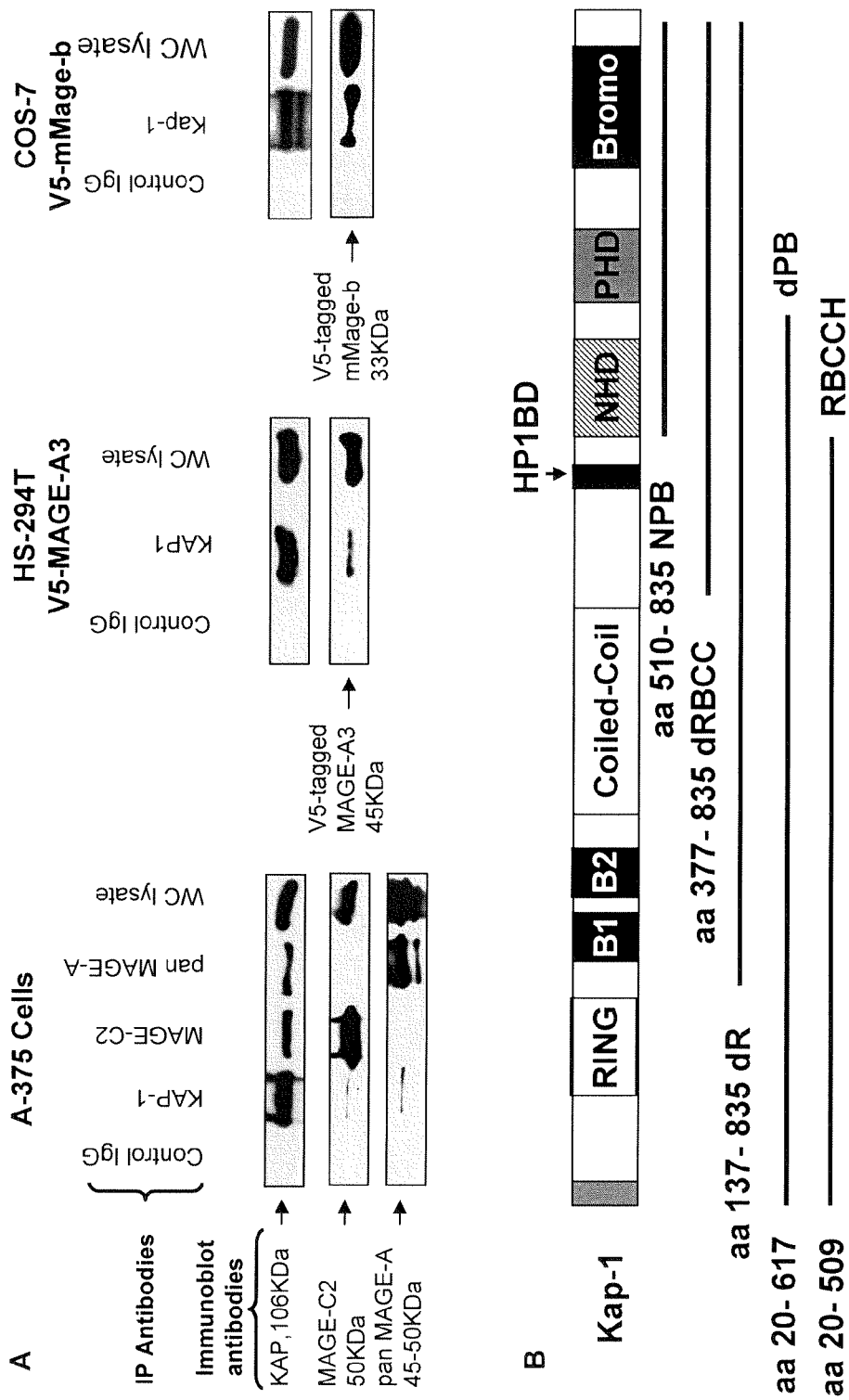
FIG. 3 shows that MAGE-A, mMage-b, and MAGE-C proteins form complexes with KAP1. A. Immunoprecipitations show that KAP1 co-precipitates with endogenous MAGE-A and MAGE-C2 proteins, and with expressed MAGE-A3 and mMage-b proteins. B. Map of deletion mutants and KAP1 functional domains. C. MAGE-C2 and KAP1 deletion mutant expression plasmids were co-transfected into COS7 cells and lysates were immunoprecipitated with anti-MAGE-C2 antibody. Top blot: immunoblotting with antibody against the C-terminal region of KAP1 shows that immunoprecipitation of MAGE-C2 only pulls down proteins containing the BB and Coiled-Coil regions (boxed bands indicate the full length KAP1 and the dR construct). Bottom blot: Immunoblotting with antibody recognizing the N-terminal region of KAP1 shows that MAGE-C2 pulls down proteins lacking the C-terminal NHD, PHD and Bromo regions, (boxed bands indicate full length, dPB and RBCCH constructs).
Figure 3:
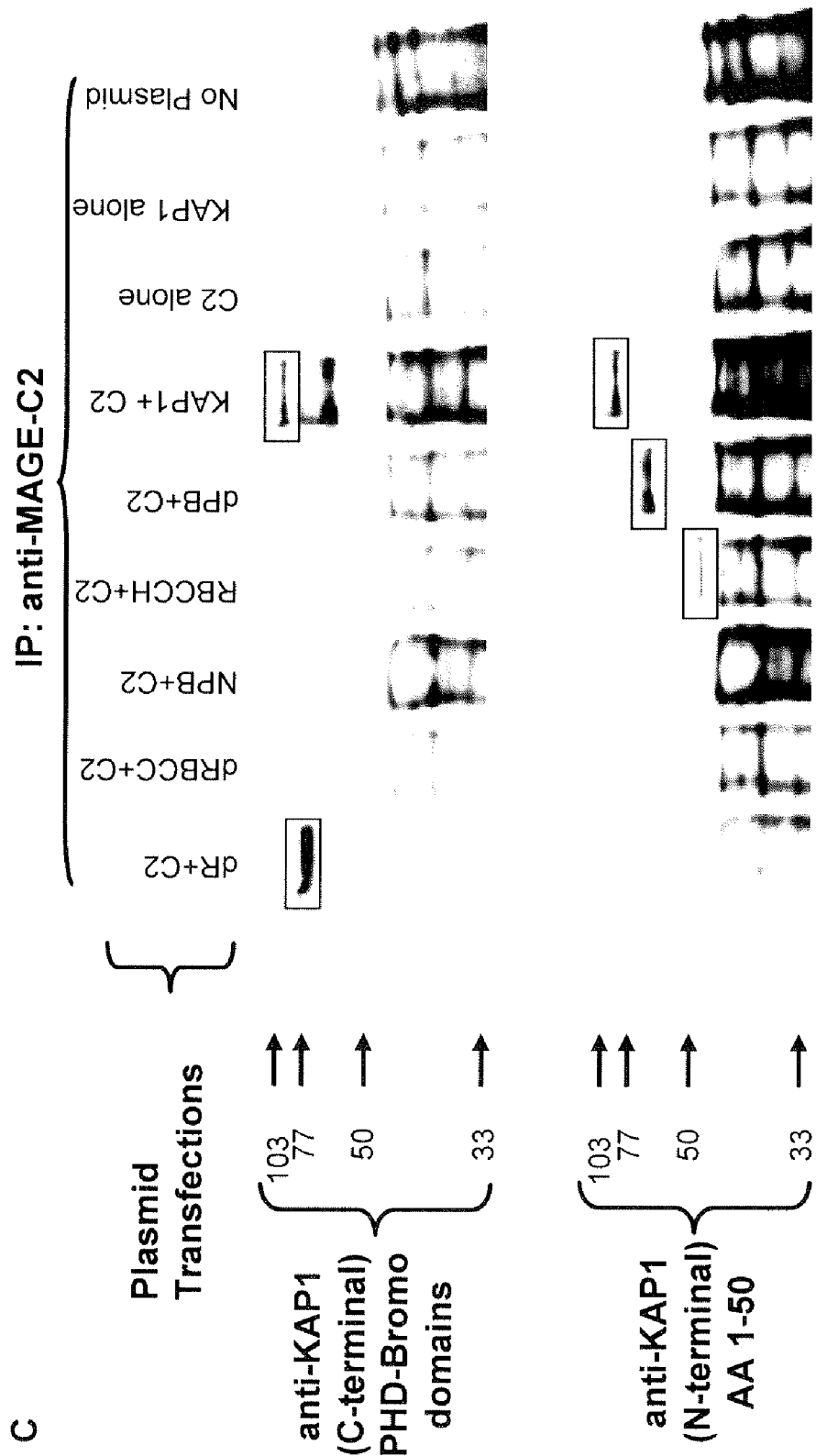

To determine which portions of KAP1 are necessary for MAGE binding, we co-transfected COS-7 cells with plasmids encoding MAGE-C2 and plasmids encoding various truncated KAP1 proteins. Immunoprecipitation of MAGE-C2 followed by immunoblotting with KAP1 antibodies recognizing either the N or C-terminal regions of KAP1 showed that the KAP1 BB-Coiled-coil region was necessary and sufficient for MAGE binding (FIG. 3B, C). Similar studies showed mMage-b binds to the BB-Coiled coil region of KAP1 (FIG. 9B), indicating that multiple MAGE proteins are capable of binding to the same region of KAP1. Overall, our data allow us to conclude that multiple different MAGE proteins, including members each of the three Class I MAGE families, can bind to KAP1, and that the ability of MAGE proteins to suppress apoptosis may involve interactions with KAP1. Our data also suggest that binding to KAP1 may be a common function of Class I MAGE molecules.

Example 4

MAGE Proteins Facilitate KAP1/p53 Complex Formation and p53 Suppression

Figure 4:
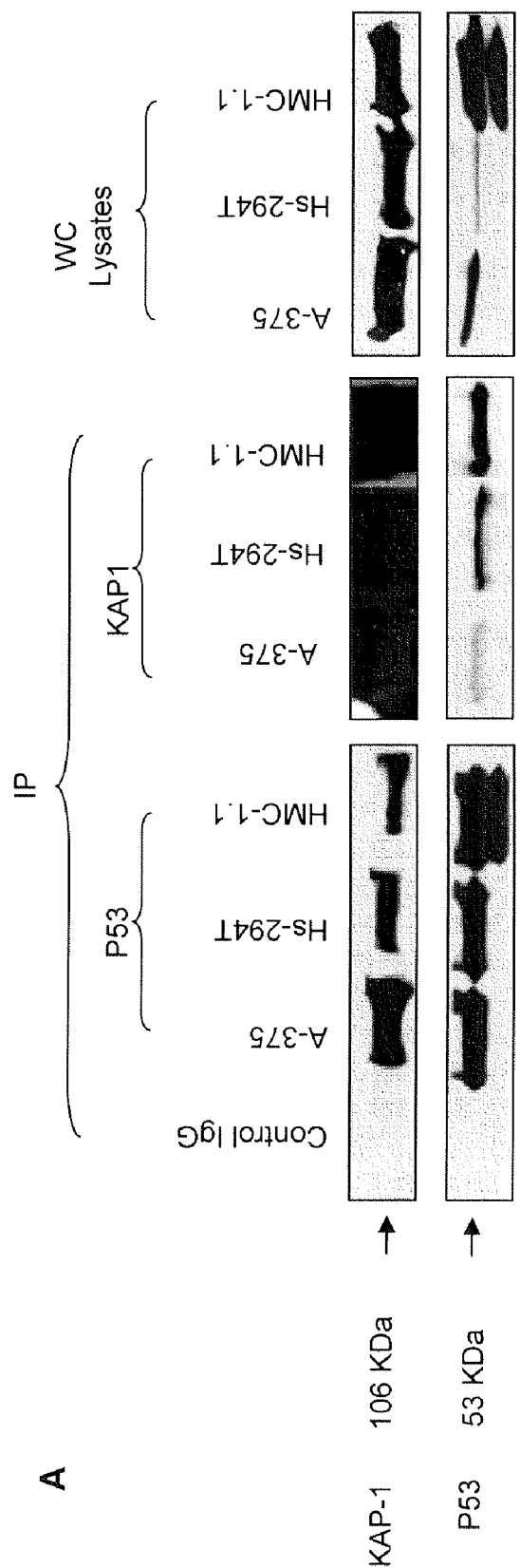
FIG. 4 shows that MAGE protein expression augments KAP1/p53 complex formation and suppression of p53. A. Co-immunoprecipitation of endogenous KAP1 and p53. B. The columns indicated with * show decreases in co-immunoprecipitated KAP1 and p53, and decreased MAGE protein in whole cell lysates after treatment with MAGE siRNA. C. The histograms show the relative densities of the bands of co-immunoprecipitated p53 and Kap-1 shown in 4B. D. MAGE knockdown increases levels of total p53 and acetylated p53 determined by the cytoblot technique. *=Significantly different from MAGE-siRNA transfected and control siRNA transfected cells, $p<0.05$ by T-Test, n=6.
Figure 4:
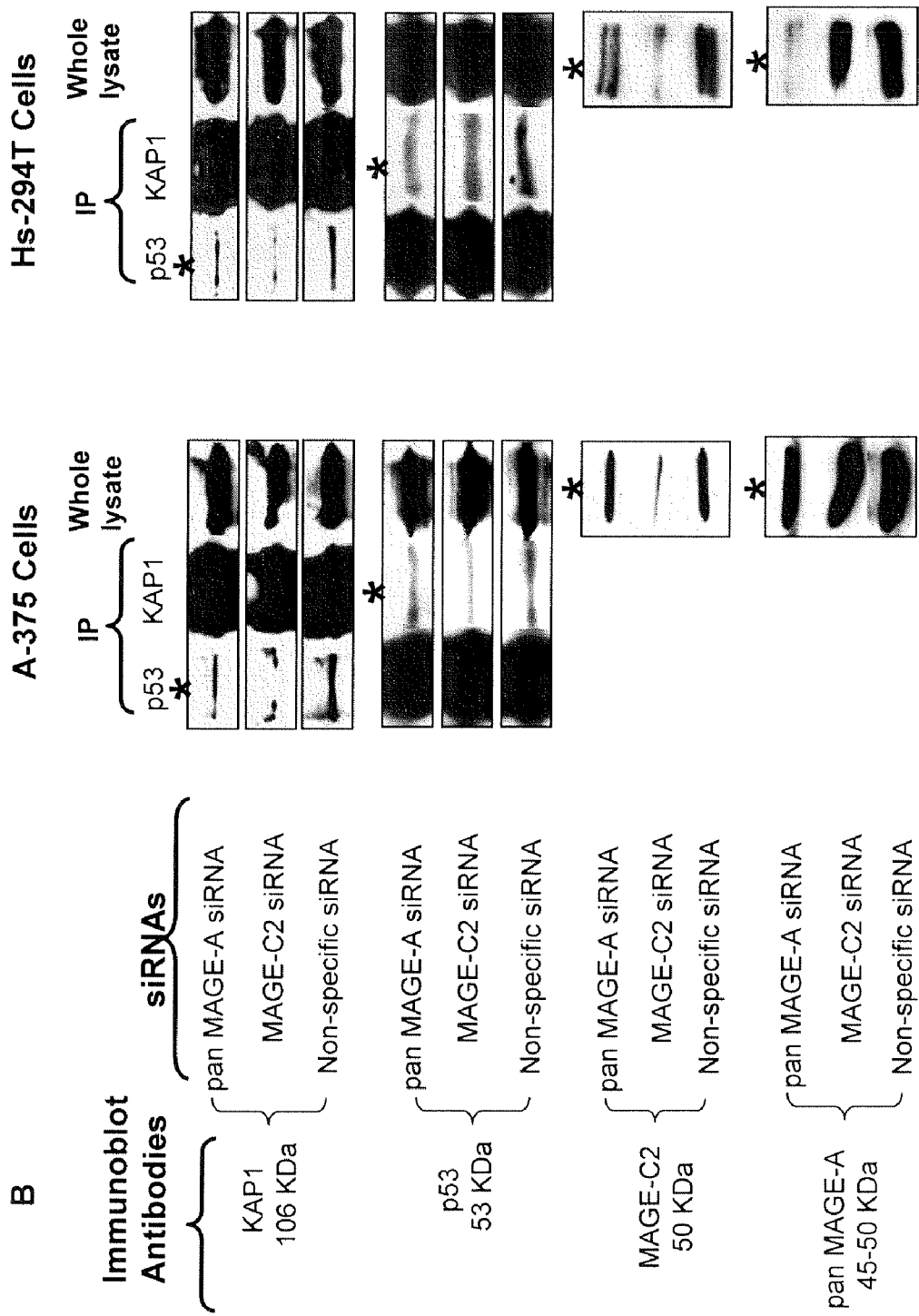
Figure 4:
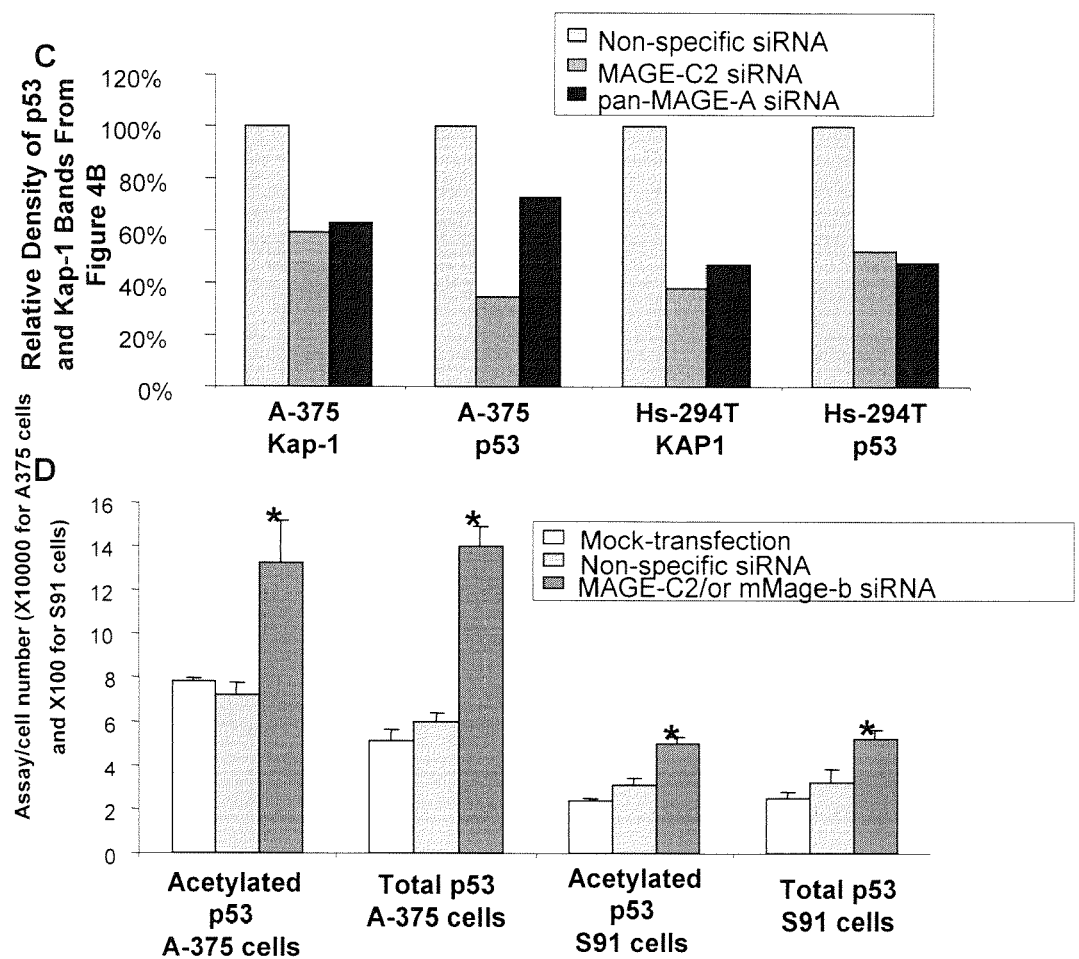
Figure 5:
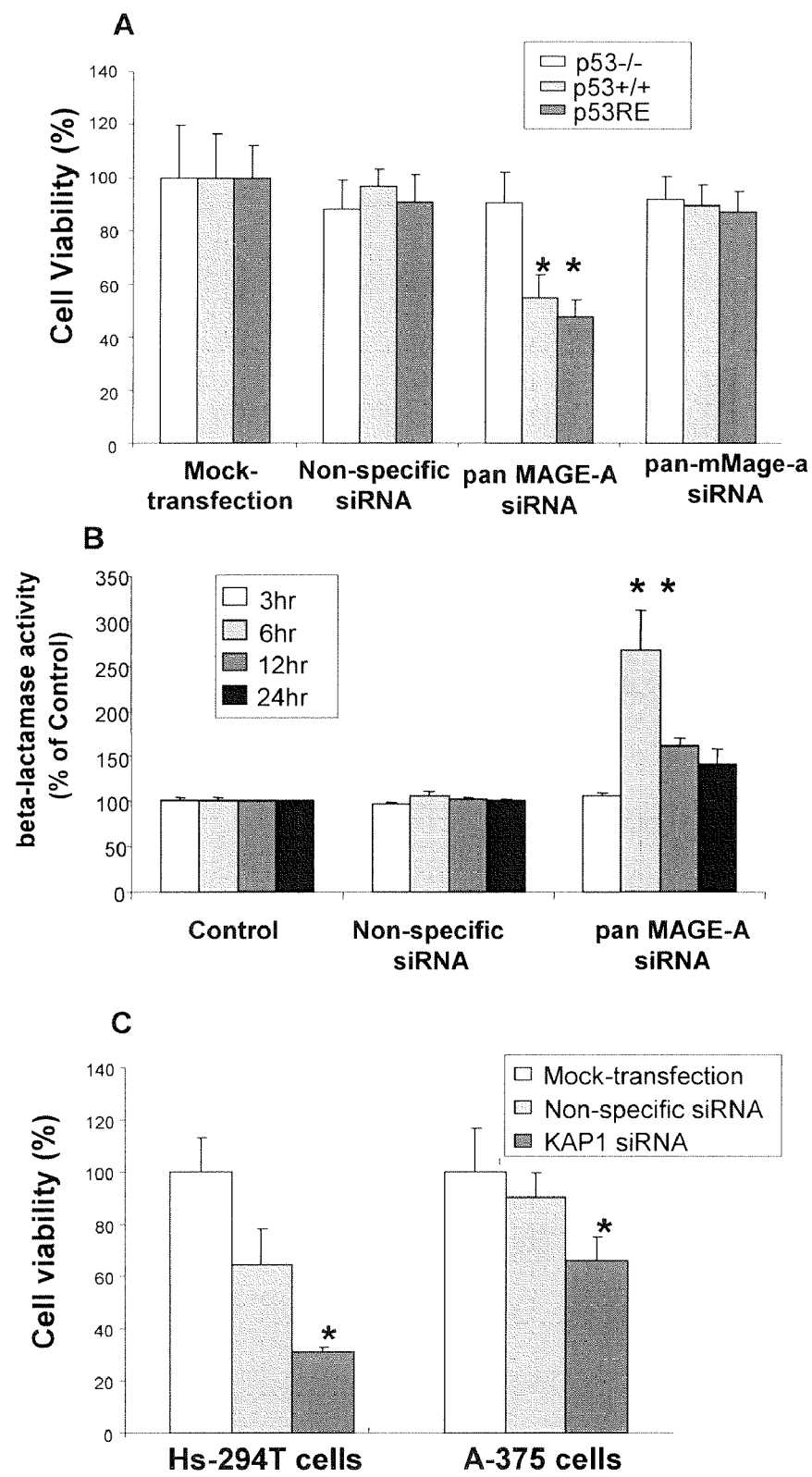
FIG. 5 A: MAGE siRNA suppresses the viability of the parental and p53RE-BLA HCT116 cell lines, but not in the p53−/− variant of HCT116. B. MAGE-A knockdown activates a beta-lactamase reporter gene driven by a p53 consensus sequence promoter in the p53RE-BLA HCT116 cell line. Activation of the reporter gene indicates transcriptional activity of endogenous p53. The assays were performed at different time points post transfection as shown above, and p53 activity reached to peak 6 hours after MAGE gene was knockdown. C. KAP1 siRNA inhibits growth of human melanoma cells. *$p<0.05$, T-Test compared with non-specific siRNA treatment, this analysis was obtained from two individual experiments with triplicates for each group.
Figure 10:
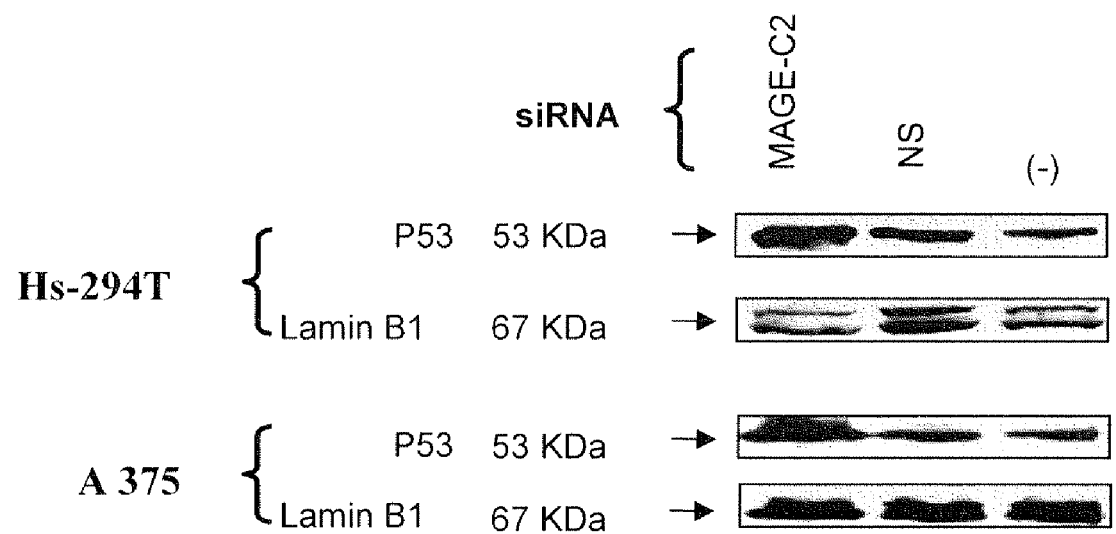
FIG. 10 depicts the result of immunoblotting which shows an increase in immunoreactive p53 in the nuclear fractions of the Hs-294T and A375 human melanoma cell lines 24 h after knockdown of MAGE-C2 compared to non-specific siRNA and no siRNA controls. Immunoblot of the nuclear protein Lamin B1 shows the purity of fractionation and serves as a protein loading control.
Figure 11:
FIG. 11 shows that MAGE-A protein is expressed in all three HCT 116 cell variants.

KAP1 is known to co-repress p53 by several mechanisms including decreasing p53 expression by facilitating its degradation and by blocking p53 acetylation and DNA binding (transcriptional activating) function (15). Therefore, we next looked for interactions between p53, MAGE, and KAP1. Unlike Monte et al, we did not detect direct binding of MAGE proteins to p53 (data not shown). However, we did find that KAP1 formed complexes with p53 and that MAGE knockdown decreased KAP1/p53 binding (FIG. 4A, B, C). MAGE knockdown also resulted in increased immunoreactive p53 and acetylated p53 (FIG. 4D and FIG. 10), suggesting that MAGE binding facilitates KAP1 repression of p53 expression and function. To test the hypothesis that MAGE proteins suppress apoptosis by suppression of p53, we used variants of the HCT116 colon cancer cell line which express moderate levels of total MAGE-A protein (FIG. 11). As we have shown for malignant melanoma and mast cell lines, MAGE siRNA suppressed the viability and apoptosis of the parental HCT116 cell line (viability data FIG. 5A, apoptosis data not shown). However, MAGE knockdown could not induce apoptosis in the absence of p53, since it has no significant effect on viability or apoptosis of HCT116 cells that are $p53^{-/-}$. Furthermore, MAGE knockdown activated an integrated beta lactamase reporter gene controlled by a consensus p53 responsive element in the p53RE-BLA variant of the HCT116 cell line (FIG. 5B). Finally, if MAGE suppression of apoptosis is dependent on the function of KAP1, knockdown of KAP1 should also decrease cell viability. KAP1 knockdown did indeed suppress cell viability (FIG. 5C). Thus, our data allow us to conclude that expression of select Class I MAGE proteins promotes cell viability by preventing apoptosis and that a likely mechanism of action is that MAGE proteins function as co-factors supporting KAP1 dependent suppression of p53.

Example 5

MAGE Suppression Inhibits Tumor Growth In Vivo

Figure 6:
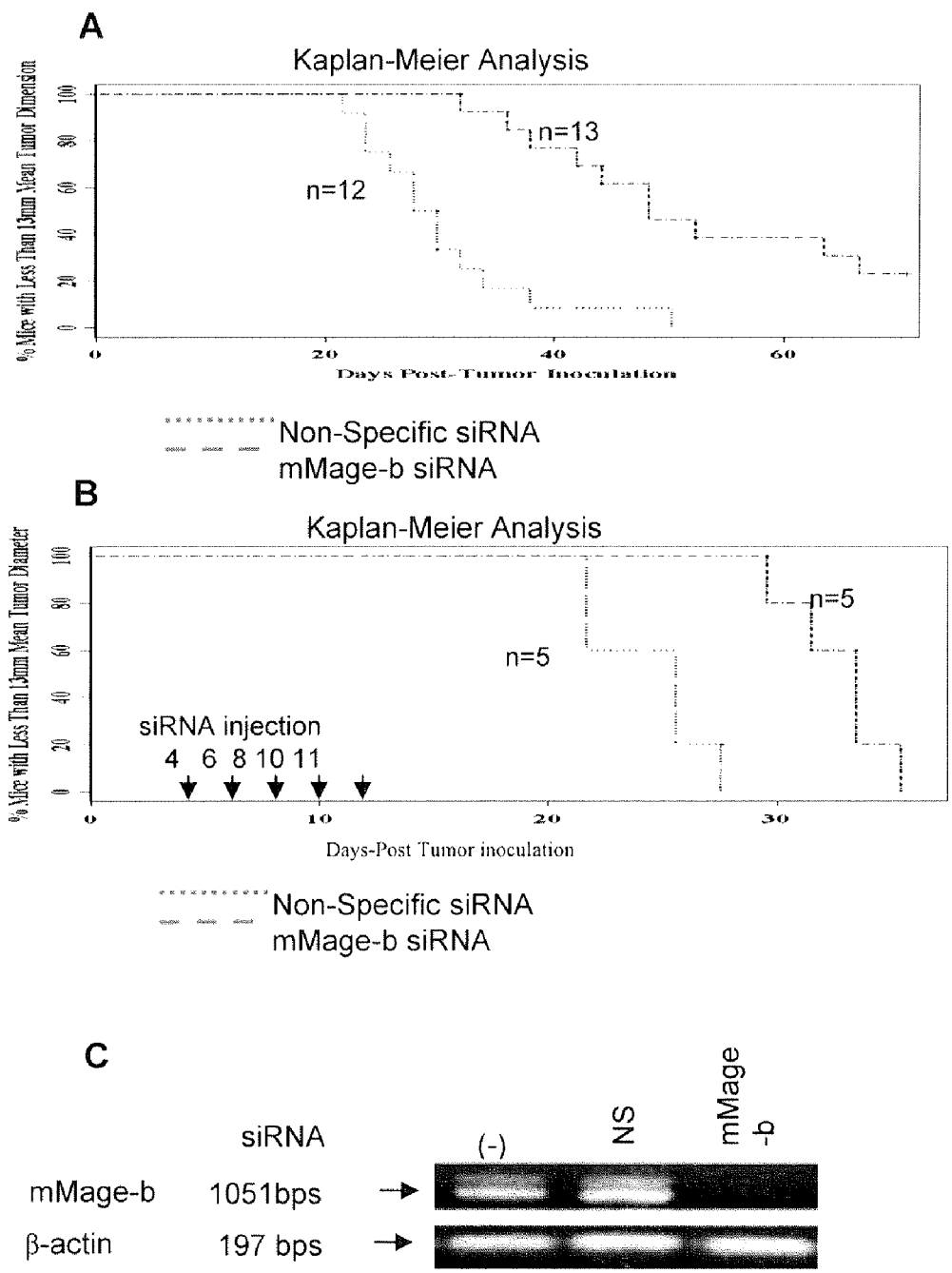
FIG. 6 shows that MAGE siRNAs suppress the growth of melanoma in vivo. A. Kaplan-Meier plot for mice injected with S91 cells transfected pre-inoculation with 100 nM control or mMage-b siSTABLE-PLUS siRNA. B. Kaplan-Meier plot for mice inoculated with S91 cells then given intraperitoneal injections of mMage-b siSTABLE-PLUS siRNA, directly conjugated to cholesterol, on days 4, 6, 8, 10, and 11 after tumor inoculation. C. Validation study shows loss of mMage-b target mRNA in tumor cells 48 hours after mMage-b siRNA treatment.
Figure 12:
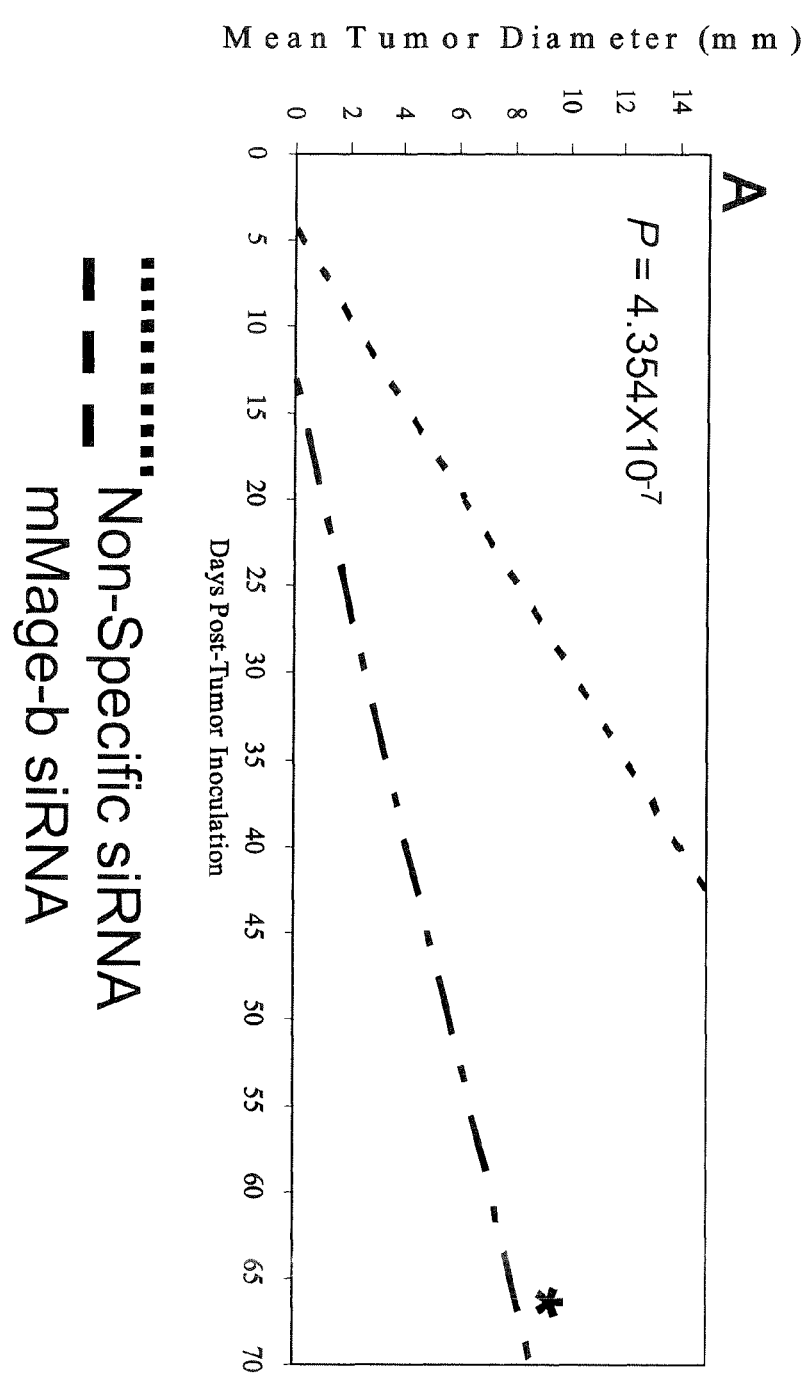
FIG. 12 shows the result of an analysis of growth of mMage-b siRNA transfected S91 Cells in syngenic mice. (Compare with FIG. 6a) A. Linear regression analysis with tumor growth averaging 0.38 mm/d for nonspecific siRNA and 0.15 mm/d for mMage-b siRNA ($p<0.001$). B, C. Log-Rank analysis in Kaplan-Meier mean and median survival between non-specific and mMage-b siRNA. ($p<0.001$).
Figure 12:
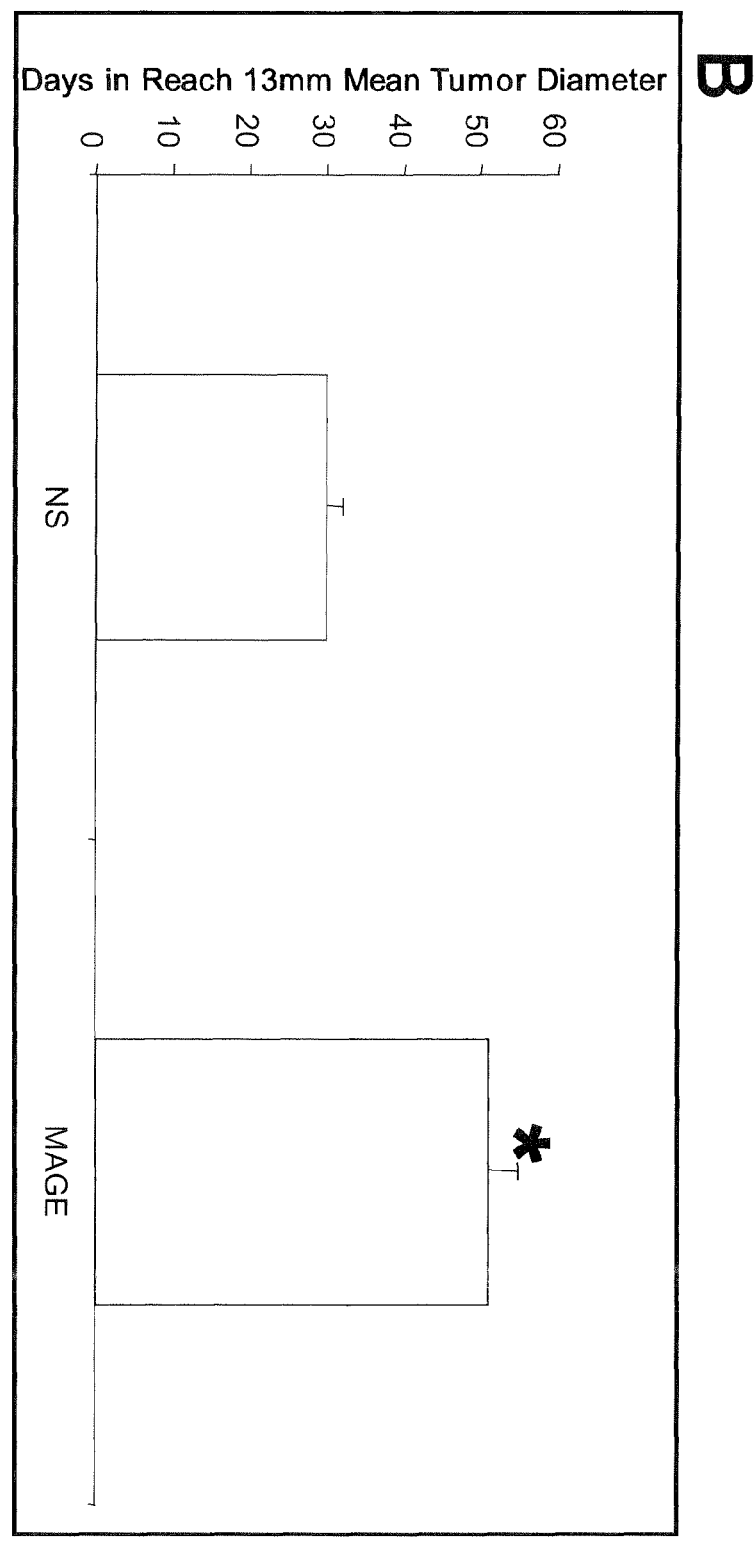
Figure 12:
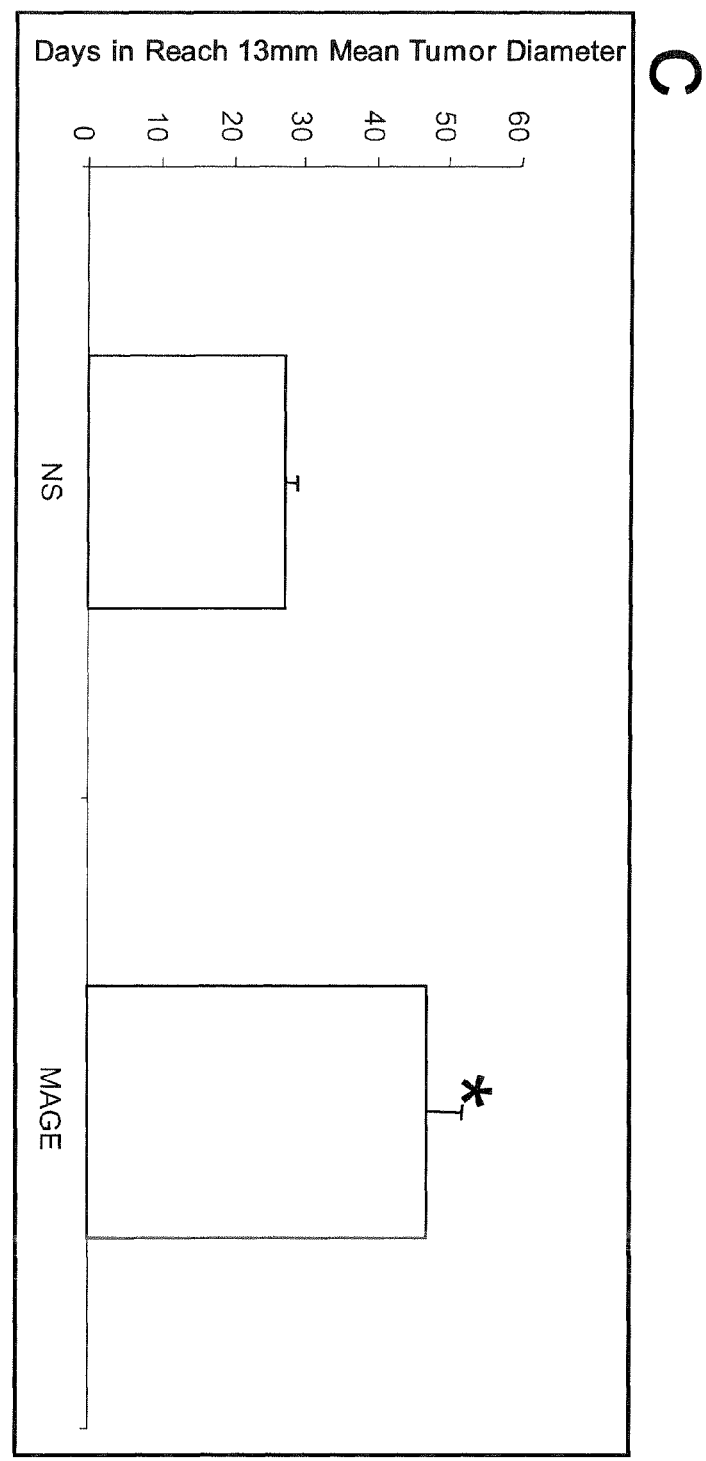

To establish whether suppressing MAGE genes can interfere with melanoma growth in vivo, we inoculated DBA mice with syngenic S91 melanoma cells that had been transfected with mMage-b siRNA. FIG. 6A shows by Kaplan-Meier plot that pre-treatment with mMage-b siRNA significantly suppresses tumor growth and improves survival. (Please see FIG. 12 for additional analysis). Furthermore, although all control siRNA treated mice developed tumors, three of the mice receiving mMage-b siRNA treated cells never developed tumors.

Figure 13:
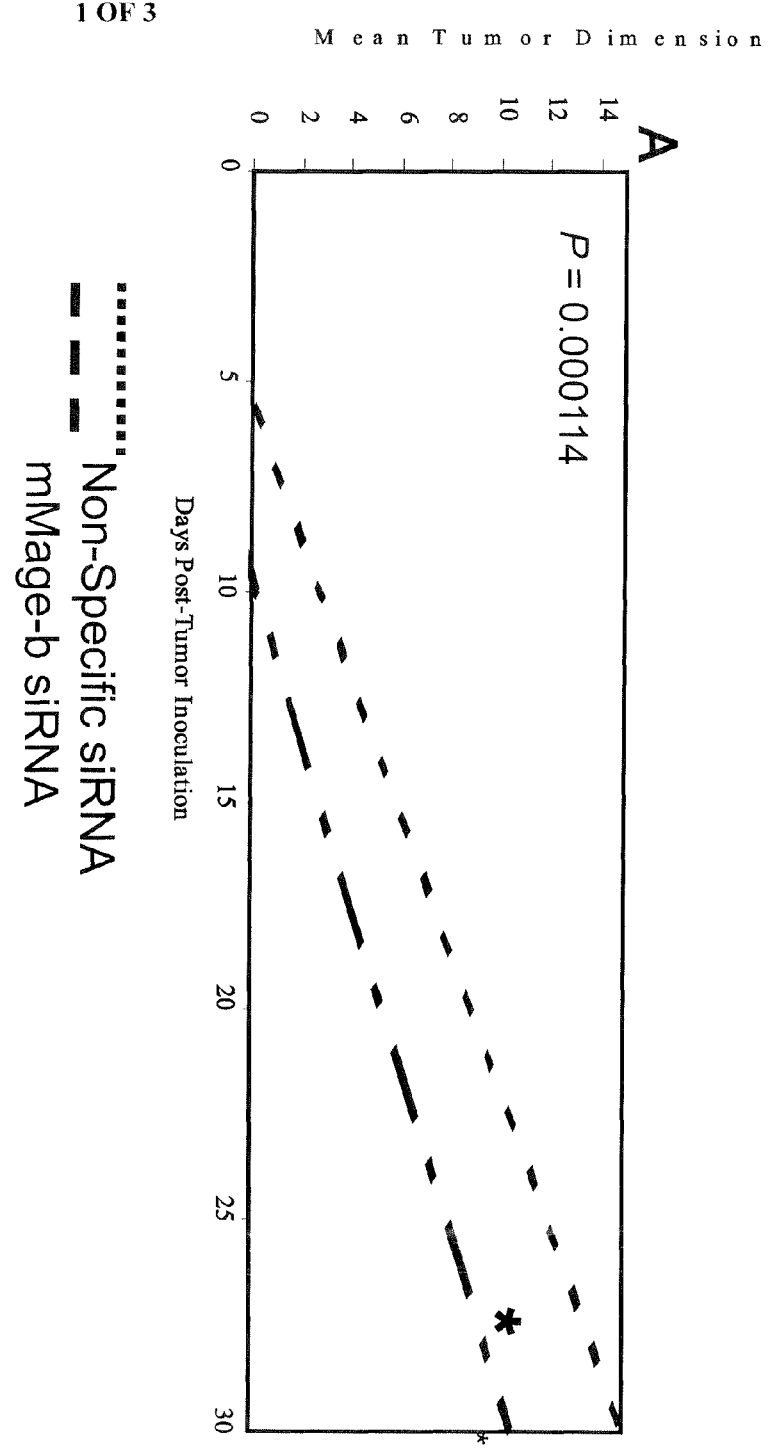
FIG. 13 depicts the result of an analysis of growth of S91 cells in syngenic mice treated with intraperitoneal injections of cholesterol conjugated siRNA. (Compare with FIG. 6b) A. Linear Regression analysis, tumor diameter increases averaged 0.61 mm/d with nonspecific siRNA and 0.51 mm/d with mMage-b siRNA. ($p<0.01$, n=5 for both mMage-b and control siRNA groups). B, C. Log-Rank analysis, significant difference in Kaplan-Meier mean and median survival between non-specific and mMage-b siRNA ($p<0.002$). *=statistically significant difference from control siRNA.

Early human melanomas and other solid tissue malignancies can be cured by complete excision, and it is usually only when the tumor has already metastasized that systemic treatment is required. To simulate this clinical situation we administered siRNA parenterally when the tumors were not yet palpable, four days after subcutaneous inoculation. In one experiment we gave a series of five intraperitoneal injections of 12 nmol mMage-b siRNA in polyethylenimine (PEI), and found that it prolonged the time to reach the target tumor size by an average of five days compared to mice treated with similar doses of non-specific siRNA ($p<0.01$ by log-Rank, $p=7.587\times10^{-6}$ by regression analysis, n=11 for treatment group and n=8 for control group). In a second experiment, intraperitoneal injections of mMage-b siRNA directly conjugated to cholesterol prolonged the time for tumors to grow to the target diameter by eight days compared to injections of similar preparations of non-specific siRNA (FIG. 6B, and FIG. 13, $p<0.01$ by regression analysis and $p<0.002$ by log-Rank analysis, n=5 for both mMage-b and control siRNA groups). In separate experiments, RT-PCR target analysis showed loss of amplifiable mMage-b mRNA in established tumors removed from mice 48 hours after treatment with intraperitoneal mMage-b siRNA, but not in tumors removed from mice treated with non-specific siRNA (FIG. 6C).

The biological result disclosed above, showing suppression of melanoma cell growth in vitro and in vivo, is significant. Combined with the previous work by some of the inventors (17), the knockdown studies disclosed herein fulfill criteria for demonstrating a "classical" RNAi response including showing specificity of reagents and reduction of gene expression at the mRNA and protein levels (20). The studies of individual siRNAs targeted to different mMage-b mRNA sequences serve as multiplicity controls by demonstrating similar biologic effects with two or more siRNAs, and together with the irrelevant control siRNAs and cross species studies indicate the sequence specificity of induction of apoptosis.

While not willing to be bound by any theory, the present inventors believe that the basic mechanism of the inhibition is the induction of apoptosis by suppression of MAGE gene expression. The inventors have further shown that this phenomenon is mediated by MAGE binding to KAP1 and suppression of p53. The data above clearly show that members of all three Class I MAGE protein families can promote cell viability and therefore can provide a growth advantage to melanomas and other malignancies.

The anti-MAGE-A antibody used for immunoprecipitation recognizes a common antigen present on all MAGE-A proteins except MAGE-A1. Although it is not clear whether all of the individual MAGE-A proteins interact with KAP1 in the cell lines used, the data on cell viability using siRNAs specific for individual MAGE-A family members suggest that suppression of apoptosis is a common function of multiple MAGE molecules, and that this may be a function of binding between the MAGE common homology domain and the KAP1 BB-CC region. The above data also support a previous proposal that the existence of multiple nearly identical MAGE family members enables a single critical function to be expressed under different transcriptional controls (1). It may be expected that the highly related MAGE family members that are not down-regulated by specific siRNA targets would still bind to KAP1 and still be able to inhibit p53 activity. However, close examination of the reciprocal immunoprecipitations in FIGS. 3A and 4B show that only a percentage of KAP1 is bound to particular MAGE molecules at any one time and that only a percentage of individual MAGE molecules are bound to KAP1. The fact that apoptosis occurs in this context suggests that the total amount of MAGE protein available affects the level of suppression and that MAGE/KAP1 binding may be in a dynamic equilibrium. Precedent for such a system exists in the regulation of p53 by KAP1 and MDM2 in which p53 expression is tightly controlled with a feedback loop in which p53 stimulates transcription of MDM2 and MDM2 binds directly to p53, blocking its transcription related functions and increasing degradation of p53 by polyubiquitination (15). Alternatively, the formation of complexes between different classes of MAGE proteins might explain this phenomenon but there is no experimental support for such a model since neither our own yeast two hybrid screen nor those reported by others have implicated MAGE-MAGE binding or the formation of MAGE homo- or hetero-dimers (22-24).

MAGE-A1 appears to be an exception since suppression of MAGE-A1 does not significantly reduce cell viability. MAGE-A1 has the least common homology among the MAGE-A proteins and unlike other Class I MAGE proteins has been shown to bind to and inhibit the activity of the intracellular portion of Notch1, a SKIP-interacting transactivator (23). Thus, our data are in agreement with previous studies showing MAGE-A1 has a different binding partner and a different specific function than those we find for other Class I MAGE molecules.

Our results differ somewhat from those of Monte et al who recently reported that MAGE-A2 binds to p53 and suppresses p53 function (16). Using immunoprecipitation of endogenous MAGE and immunoblotting we were unable to confirm their finding of direct binding of MAGE-A molecules to p53, but our reagents and cell lines differ significantly from theirs and our overall findings agree with theirs in that we also find: 1. MAGE proteins bind to complexes that include p53 and 2. MAGE proteins promote cell viability via suppression of p53. Our studies, however, show that Class I MAGE proteins of all three sub-families may function to suppress apoptosis in tumor cells. Furthermore, we find anti-apoptotic function in specific MAGE proteins including MAGE-A2, A3, A5, and A6, mMage-b, and MAGE-C2. Although Monte et al did not see increased survival with transfection mediated expression of MAGE proteins in select cell lines, our results are not incompatible with theirs since there is no a priori reason to believe that those cell lines need p53 suppression by MAGE proteins for survival. Our findings also fit nicely with those of White et al (23) who found that KAP1 rapidly localizes to sites of DNA strand breakage, establishing a link between KAP1, chromatin mediated transcriptional repression, and recognition/repair of DNA damage. Combined with our discoveries of MAGE suppression of apoptosis and MAGE binding to KAP1, these data fit well with the hypothesis that select MAGE proteins can interfere with p53 dependent DNA damage responses and thus offer a survival advantage to tumor cells.

Interestingly, apoptosis suppressed by MAGE proteins is not affected by caspase inhibitors (FIG. 8). This result is unusual but not unheard of since p53 dependent, caspase independent apoptosis has been reported in several systems including neurons (26, 27) and other cell types (28-30). Perhaps of greater interest are the implications these studies have for the role of MAGE proteins in normal biology. Normal spermatogenesis requires p53-dependent cellular proofreading since $p53^{-/-}$ male mice have decreased germ cell apoptosis, an increased percentage of morphologically abnormal sperm, and reduced fertility (31). It is known that both the KIT tyrosine kinase and multiple MAGE proteins are expressed in developing sperm during meiosis and we recently reported that activation of the KIT receptor tyrosine kinase promotes expression of MAGE genes by maintaining their promoter regions in a hypomethylated state, the first report of epigenetic regulation of specific genes by a tyrosine kinase (7, 17, 32, 33). A clue to the normal function of MAGE proteins comes from the observation that the males but not the females of $kit^{W-v/W-v}$ partial loss of function mutant mice are infertile and exhibit increased germ cell apoptosis and decreased germ cell viability (33-35). Surprisingly, this defect is rescued in double-mutant $p53^{-/-}$ $kit^{W-v/W-v}$ mice, indicating that KIT normally regulates a p53-dependent apoptotic pathway in developing male germ cells by (35). We believe that KIT suppression of p53 in the testes is mediated through regulation of MAGE expression and MAGE binding to KAP1. We also note that KIT appears to be relevant to human fertility since decreased KIT expression is seen in testes of subfertile adult humans, and is associated with increased apoptosis in spermatocytes (36).

MAGE proteins were the first CT antigens discovered, and their limited tissue distribution has long been recognized as a potential key to tumor specific treatment of many different malignancies (2). The fact that MAGE genes are normally expressed in cells of the spermatogenic series during meiosis suggests that they may be members of the family of germ line anti-apoptotic genes which are involved in the maintenance of genomic stability and fertility in mammalian germ cells, and may protect cells from triggering an apoptotic response during meiosis (37, 38). The hypothesis that developing neoplastic cells can co-opt these functions and use them to gain a growth advantage and resistance to apoptosis would help explain the increasing amount of correlative data which suggest that expression of Class I MAGE proteins and other CT antigens may actually contribute to the development of malignancies (4, 6). However, work published thus far has not shown whether MAGE gene expression is a functionally irrelevant by-product of cellular transformation or actually contributes to the development of melanoma and other malignancies. In answer to this question, our studies show unequivocally that inhibition of selected MAGE proteins can decrease the viability of melanoma cells in vitro and in vivo. The findings above therefore establish that interference with the expression or function of select Class I MAGE antigens is itself sufficient for the suppression of growth of melanomas and other malignancies.

Example 5

Figure 14:
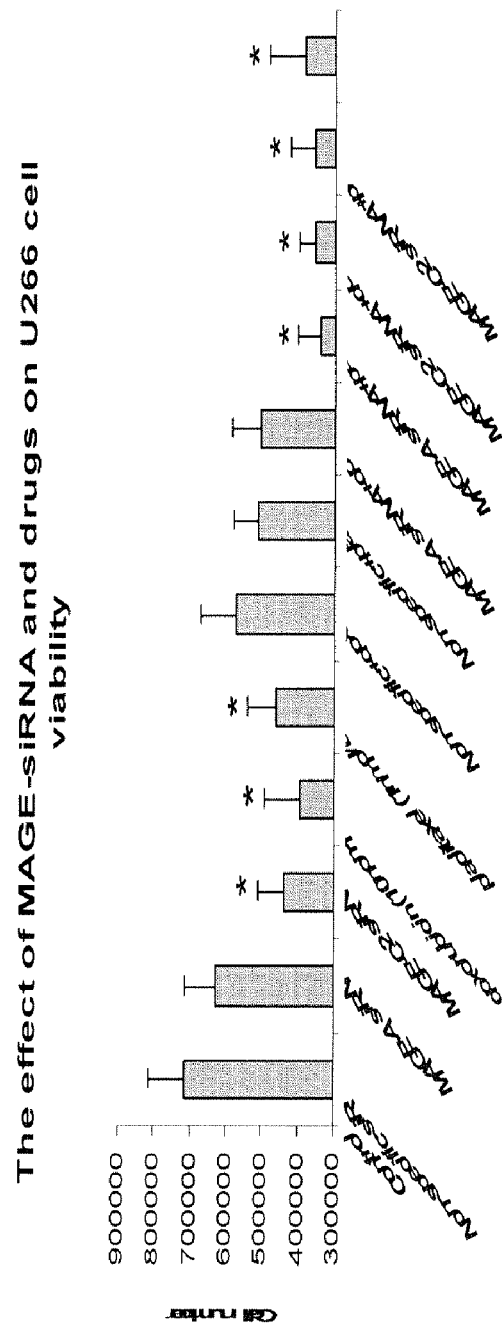
FIG. 14 shows that MAGE-A and MAGE-C2 siRNAs sensitize U226 Myeloma cells to the DNA damaging agents doxorubicin and paxlitaxol.

MAGE-A and MAGE-C2 siRNAs Sensitize U226 Myeloma Cells to the DNA Damaging Agents Doxorubicin and Paxlitaxol MAGE siRNA decreases U226 Myeloma cell growth and synergizes with doxorubicin and paxlitaxol to decrease viability as determined by Trypan Blue exclusion at 72 h. U226 Myeloma cell cultures were started with 400,000 cells per well, were treated with MAGE-A3 and MAGE-C2 siRNA, with or without doxorubicin (10 nmol/L) or placlitaxel (1 nmol/L). The results are shown in FIG. 14. These data show that treatment with MAGE-A3 and MAGE-C2 siRNA decreases the viability of the U226 Myeloma cells and results in increased cell death when combined with doxorubicin and paxlitaxol. In wells treated with MAGE siRNA and doxorubicin or paxlitaxol, cell numbers actually decreased. In the figure, * denotes values that are significantly different from comparable drug and culture conditions with control siRNA by T-test.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. All references cited hereinabove and/or listed below are hereby expressly incorporated by reference.

REFERENCES

1. De Plaen, E., Arden, K., Traversari, C., Gaforio, J. J., Szikora, J. P., De Smet, C., Brasseur, F., van der Bruggen, P., Lethe, B., Lurquin, C., and et al. Structure, chromosomal localization, and expression of 12 genes of the MAGE family. Immunogenetics, 40: 360-369, 1994.
2. Simpson, A. J. G., Caballero, O. L., Jungbluth, A., Chen, Y.-T., and Old, L. J. Cancer/testis antigens, gametogenesis and cancer. Nature Reviews Cancer, 5: 615, 2005.
3. Lurquin, C., De Smet, C., Brasseur, F., Muscatelli, F., Martelange, V., De Plaen, E., Brasseur, R., Monaco, A. P., and Boon, T. Two members of the human MAGEB gene family located in Xp21.3 are expressed in tumors of various histological origins. Genomics, 46: 397-408, 1997.
4. Jungbluth, A. A., Ely, S., Diliberto, M., Niesvizky, R., Williamson, B., Frosina, D., Chen, Y. T., Bhardwaj, N., Chen-Kiang, S., Old, L. J., and Cho, H. J. The cancer-testis antigens CT7 (MAGE-C1) and MAGE-A3/6 are commonly expressed in multiple myeloma and correlate with plasma-cell proliferation. Blood, 106: 167-174, 2005.
5. De Smet, C., Lurquin, C., Lethe, B., Martelange, V., and Boon, T. DNA methylation is the primary silencing mechanism for a set of germ line- and tumor-specific genes with a CpG-rich promoter. Mol Cell Biol, 19: 7327-7335, 1999.
6. Dhodapkar, M. V., Osman, K., Teruya-Feldstein, J., Filippa, D., Hedvat, C. V., Iversen, K., Kolb, D., Geller, M. D., Hassoun, H., Kewalramani, T., Comenzo, R. L., Coplan, K., Chen, Y. T., and Jungbluth, A. A. Expression of cancer/testis (CT) antigens MAGE-A1, MAGE-A3, MAGE-A4, CT-7, and NY-ESO-1 in malignant gammopathies is heterogeneous and correlates with site, stage and risk status of disease. Cancer Immun, 3: 9, 2003.
7. Jungbluth, A. A., Busam, K. J., Kolb, D., Iversen, K., Coplan, K., Chen, Y. T., Spagnoli, G. C., and Old, L. J. Expression of MAGE-antigens in normal tissues and cancer. Int J Cancer, 85: 460-465, 2000.
8. Sigalotti, L., Fratta, E., Coral, S., Tanzarella, S., Danielli, R., Colizzi, F., Fonsatti, E., Traversari, C., Altomonte, M., and Maio, M. Intratumor heterogeneity of cancer/testis antigens expression in human cutaneous melanoma is methylation-regulated and functionally reverted by 5-aza-2'-deoxycytidine. Cancer Res, 64: 9167-9171, 2004.
9. Friedman J R, F. W., Jensen D E, Speicher D W, Huang X P, Neilson E G, Rauscher F J 3rd. KAP1, a novel corepressor for the highly conserved KRAB repression domain. Genes Dev., 10: 2067-2078, 1996.
10. Kim, S.-S., Chen, Y.-M., O'Leary, E., Witzgall, R., Vidal, M., and Bonventre, J. V. A novel member of the RING finger family, KRIP-1, associates with the KRAB-A transcriptional repressor domain of zinc finger proteins. PNAS, 93: 15299-15304, 1996.
11. Moosmann, P., Georgiev, O., Le Douarin, B., Bourquin, J. P., and Schaffner, W. Transcriptional repression by RING finger protein TIF1 beta that interacts with the KRAB repressor domain of KOX1. Nucl. Acids Res., 24: 4859-4867, 1996.
12. Cammas, F., Mark, M., Dolle, P., Dierich, A., Chambon, P., and Losson, R. Mice lacking the transcriptional corepressor TIF1beta are defective in early postimplantation development. Development, 127: 2955-2963, 2000.
13. Looman, C., Abrink, M., Mark, C., and Hellman, L. KRAB Zinc Finger Proteins: An Analysis of the Molecular Mechanisms Governing Their Increase in Numbers and Complexity During Evolution. Mol Biol Evol, 19: 2118-2130, 2002.
14. Schultz, D. C., Ayyanathan, K., Negorev, D., Maul, G. G., and Rauscher, F. J., III SETDB1: a novel KAP1-associated histone H3, lysine 9-specific methyltransferase that contributes to HP1-mediated silencing of euchromatic genes by KRAB zinc-finger proteins. Genes Dev., 16: 919-932, 2002.
15. Wang C, I. A., Chen L, Fredericks W J, Seto E, Rauscher F J 3rd, Chen J. MDM2 interaction with nuclear corepressor KAP1 contributes to p53 inactivation. EMBO J., 24: 3279-3290, 2005.
16. Monte, M., Simonatto, M., Peche, L. Y., Bublik, D. R., Gobessi, S., Pierotti, M. A., Rodolfo, M., and Schneider, C. MAGE-A tumor antigens target p53 transactivation function through histone deacetylase recruitment and confer resistance to chemotherapeutic agents. Proc Natl Acad Sci USA, 103: 11160-11165, 2006.
17. Yang, B., O'Herrin, S., Wu, J., Reagan-Shaw, S., Ma, Y., Nihal, M., and Longley, B. J. Select Cancer Testes Antigens of the MAGE-A, -B, and -C Families Are Expressed in Mast Cell Lines and Promote Cell Viability In Vitro and In Vivo. J Invest Dermatol, 127: 267-275, 2007.
18. Butterfield, J. H., Weiler, D., Dewald, G., and Gleich, G. J. Establishment of an immature mast cell line from a patient with mast cell leukemia. Leuk Res, 12: 345-355, 1988.
19. Sypniewska R K, H. L., Tarango M, Gauntt S, Leal B Z, Reddick R L, Gravekamp C Prevention of metastases with a Mage-b DNA vaccine in a mouse breast tumor model: potential for breast cancer therapy. Breast Cancer Res Treat, 91: 19-28, 2005.
20. Stockwell et al., Chem. Biol. 6:71 (1999)
21. Editorial Whither RNAi? Nature Cell Biology, 5: 489-490, 2003.
22. Cho, H. J. C., Otavia L.; Sacha Gnjatic; Andrade, Valéria C. C.; Colleoni, Gisele W.; Vettore, Andre L.; Outtz, Hasina H.; Fortunato, Sheila; Altorki, Nasser; Ferrera, Cathy A.;

Chua, Ramon; Jungbluth, Achim A.; Chen, Yao-Tseng; Old, Lloyd J.; Simpson, Andrew J. G. Physical interaction of two cancer-testis antigens, MAGE-C1 (CT7) and NY-ESO-1 (CT6). Cancer Immunity, 6, 2006.
23. Laduron, S., Deplus, R., Zhou, S., Kholmanskikh, O., Godelaine, D., De Smet, C., Hayward, S. D., Fuks, F., Boon, T., and De Plaen, E. MAGE-A1 interacts with adaptor SKIP and the deacetylase HDAC1 to repress transcription. Nucleic Acids Res, 32: 4340-4350, 2004.
24. Sakurai et al. J. Biol. Chem. 279:15505-14 (2004)
25. White, D. E., Negorev, D., Peng, H., Ivanov, A. V., Maul, G. G., and Rauscher, F. J., III KAP1, a Novel Substrate for PIKK Family Members, Colocalizes with Numerous Damage Response Factors at DNA Lesions. Cancer Res, 66: 11594-11599, 2006.
26. Cregan, S. P., Fortin, A., MacLaurin, J. G., Callaghan, S. M., Cecconi, F., Yu, S. W., Dawson, T. M., Dawson, V. L., Park, D. S., Kroemer, G., and Slack, R. S. Apoptosis-inducing factor is involved in the regulation of caspase-independent neuronal cell death. J Cell Biol, 158: 507-517, 2002.
27. Cregan, S. P., MacLaurin, J. G., Craig, C. G., Robertson, G. S., Nicholson, D. W., Park, D. S., and Slack, R. S. Bax-dependent caspase-3 activation is a key determinant in p53-induced apoptosis in neurons. J Neurosci, 19: 7860-7869, 1999.
28. Kook, S.-H. S., Young-Ok; Chung, Song-Woo; Lee, Seung-Ah; Kim, Jong-Ghee; Jeon, Young-Mi and Lee, Jeong-Chae Caspase-independent death of human osteosarcoma cells by flavonoids is driven by p53-mediated mitochondrial stress and nuclear translocation of AIF and endonuclease G. Apoptosis, 12: 1289-1298, 2007.
29. Martel, V., Filhol, O., Colas, P., and Cochet, C. p53-dependent inhibition of mammalian cell survival by a genetically selected peptide aptamer that targets the regulatory subunit of protein kinase CK2. Oncogene, 25: 7343, 2006.
30. Stambolsky, P., Weisz, L., Shats, I., Klein, Y., Goldfinger, N., Oren, M., and Rotter, V. Regulation of AIF expression by p53. Cell Death Differ, 13: 2140, 2006.
31. Yin, Y., Stahl, B. C., DeWolf, W. C., and Morgentaler, A. p53-mediated germ cell quality control in spermatogenesis. Dev Biol, 204: 165-171, 1998.
32. Jungbluth, A. A., Chen, Y. T., Busam, K. J., Coplan, K., Kolb, D., Iversen, K., Williamson, B., Van Landeghem, F. K., Stockert, E., and Old, L. J. CT7 (MAGE-C1) antigen expression in normal and neoplastic tissues. Int J Cancer, 99: 839-845, 2002.
33. Sandlow, J. I., Feng, H. L., and Sandra, A. Localization and expression of the c-kit receptor protein in human and rodent testis and sperm. Urology, 49: 494-500, 1997.
34. Blume-Jensen, P., Jiang, G., Hyman, R., Lee, K. F., O'Gorman, S., and Hunter, T. Kit/stem cell factor receptor-induced activation of phosphatidylinositol 3'-kinase is essential for male fertility. Nat Genet, 24: 157-162, 2000.
35. Jordan, S. A., Speed, R. M., Bernex, F., and Jackson, I. J. Deficiency of Trp53 rescues the male fertility defects of Kit(W-v) mice but has no effect on the survival of melanocytes and mast cells. Dev Biol, 215: 78-90, 1999.
36. Feng, H. L., Sandlow, J. I., Sparks, A. E., Sandra, A., and Zheng, L. J. Decreased expression of the c-kit receptor is associated with increased apoptosis in subfertile human testes. Fertil Steril, 71: 85-89, 1999.
37. Lettre, G., Kritikou, E. A., Jaeggi, M., Calixto, A., Fraser, A. G., Kamath, R. S., Ahringer, J., and Hengartner, M. O. Genome-wide RNAi identifies p53-dependent and -independent regulators of germ cell apoptosis in *C. elegans*. Cell Death Differ, 11: 1198-1203, 2004.
38. Takahashi K, S. S., Noguchi M, Hirohata M, Itoh K. Identification of MAGE-1 and MAGE-4 proteins in spermatogonia and primary spermatocytes of testis. Cancer Res., 55: 3478-3482, 1995.

What is claimed is:

1. A method for inhibiting the growth or proliferation, or inducing apoptosis, of a mammalian cell that expresses a MAGE gene selected from the group consisting of MAGE-A2, MAGE-A3, MAGE-A5, MAGE-A6, MAGE-A8, MAGE-A9, MAGE-A10, MAGE-A11, MAGE-A12, MAGE-B1, MAGE-B2, MAGE-B3, MAGE-B4, MAGE-C1, MAGE-C2, Necdin, MAGE-D, MAGE-E1, MAGE-F, MAGE-G, and MAGE-H, the method comprising inhibiting the binding of KAP-1 to a polypeptide encoded by the MAGE gene in the cell, by administering to the cell a substance that inhibits the formation of a complex between KAP-1 and a MAGE protein encoded by the MAGE gene, or the function of the complex, wherein the substance is a short interfering RNA molecule that specifically inhibits the expression of the MAGE gene.

2. The method according to claim 1, wherein the cell is human cell.

3. A method according to claim 1, wherein the MAGE gene is selected from the group consisting of MAGE-A2, MAGE-A3, MAGE-A5, MAGE-A6, MAGE-A8, MAGE-A9, MAGE-A10, MAGE-A11, MAGE-A12, MAGE-B1, MAGE-B2, MAGE-B3, MAGE-B4, MAGE-C1, MAGE-C2, MAGE-D, and MAGE-E1.

4. A method according to claim 3, wherein the Type I MAGE gene is MAGE A3, A5, A6, A8, A9, A10, A11 or A12, MAGE-B1, B2, B3 or B4, MAGE-C1 or C2.

5. A method according to claim 1, wherein the cell is a cancerous or malignant or neoplastic cell.

6. A method for treating melanoma in a mammal, wherein the cancer or tumor comprises a cell that expresses a MAGE gene selected from the group consisting of MAGE-A2, MAGE-A3, MAGE-A5, MAGE-A6, MAGE-A8, MAGE-A9, MAGE-A10, MAGE-A11, MAGE-A12, MAGE-B1, MAGE-B2, MAGE-B3, MAGE-B4, MAGE-C1, MAGE-C2, Necdin, MAGE-D, MAGE-E1, MAGE-F, MAGE-G, and MAGE-H, the method comprising inhibiting the binding of KAP-1 to a polypeptide encoded by the MAGE gene in the cell, by administering to the cell a substance that inhibits the formation of a complex between KAP-1 and a MAGE protein, or the function of the complex, wherein the substance is a short interfering RNA molecule that specifically inhibits the expression of the MAGE gene.

7. A method according to claim 1, wherein the cell is a cell in a testis.

8. A method according to claim 7, wherein the cell is a male germ cell.

9. A method according to claim 6, wherein the MAGE gene is a Type I MAGE gene selected from the group consisting of MAGE-A2, MAGE-A3, MAGE-A5, MAGE-A6, MAGE-A8, MAGE-A9, MAGE-A10, MAGE-A11, MAGE-A12, MAGE-B1, MAGE-B2, MAGE-B3, MAGE-B4, MAGE-C1, MAGE-C2, MAGE-D, and MAGE-E1.

10. A method according to claim 9, wherein the MAGE gene is selected from the group consisting of MAGE-A3, MAGE-A5, MAGE-A6, MAGE-A8, MAGE-A9, MAGE-A10, MAGE-A11, MAGE-A12, MAGE-B1, MAGE-B2, MAGE-B3, MAGE-B4, MAGE-C1, and MAGE-C2.

* * * * *